US009649400B2

(12) United States Patent
Furner et al.

(10) Patent No.: US 9,649,400 B2
(45) Date of Patent: May 16, 2017

(54) METHOD AND SYSTEM FOR DISPENSING A COMPOSITION

(71) Applicant: S.C. Johnson & Son, Inc., Racine, WI (US)

(72) Inventors: Paul E. Furner, Waterford, WI (US); Jeffrey L. Harwig, Franklin, WI (US); William G. Parsons, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 315 days.

(21) Appl. No.: 13/969,448

(22) Filed: Aug. 16, 2013

(65) Prior Publication Data

US 2014/0048617 A1     Feb. 20, 2014

Related U.S. Application Data

(63) Continuation-in-part of application No. 13/588,974, filed on Aug. 17, 2012, and a continuation-in-part of application No. 13/588,976, filed on Aug. 17, 2012, now Pat. No. 8,894,044.

(51) Int. Cl.
| | |
|---|---|
| A61L 9/12 | (2006.01) |
| A01M 1/20 | (2006.01) |
| A01M 7/00 | (2006.01) |
| A61L 9/14 | (2006.01) |
| B65D 83/28 | (2006.01) |
| B65D 83/30 | (2006.01) |
| B65D 83/38 | (2006.01) |

(Continued)

(52) U.S. Cl.
CPC ........... *A61L 9/127* (2013.01); *A01M 1/2038* (2013.01); *A01M 1/2044* (2013.01); *A01M 7/0003* (2013.01); *A61L 9/12* (2013.01); *A61L 9/14* (2013.01); *B65D 83/285* (2013.01); *B65D 83/30* (2013.01); *B65D 83/384* (2013.01); *A61L 2209/111* (2013.01); *A61L 2209/12* (2013.01); *B05B 1/14* (2013.01); *B05B 1/26* (2013.01)

(58) Field of Classification Search
CPC ........ A61L 9/12; A61L 9/127; A01M 1/2044; A01M 1/2055
See application file for complete search history.

(56) References Cited

U.S. PATENT DOCUMENTS

| | | |
|---|---|---|
| 3,236,458 A | 2/1966 | Ramis |
| 3,304,797 A | 2/1967 | Graveley |
| 3,369,756 A | 2/1968 | Ramis |

(Continued)

FOREIGN PATENT DOCUMENTS

| | | |
|---|---|---|
| DE | 2235541 | 1/1974 |
| DE | 2540075 | 3/1977 |

(Continued)

OTHER PUBLICATIONS

PCT/US2013/055566 International Search Report and Written Opinion dated Feb. 13, 2014.

(Continued)

*Primary Examiner* — Ryan Reis

(57) ABSTRACT

A dispensing system includes a substrate and a mechanism for discharging a flowable medium through the substrate. The discharge of the flowable medium through the substrate results in a visible plume of the flowable medium for at least 3 seconds.

16 Claims, 16 Drawing Sheets

(51) Int. Cl.
  *B05B 1/26* (2006.01)
  *B05B 1/14* (2006.01)

(56) References Cited

U.S. PATENT DOCUMENTS

| | | | |
|---|---|---|---|
| 3,550,857 A | 12/1970 | Ahlberg | |
| 3,972,473 A | 8/1976 | Harrison | |
| 4,165,835 A * | 8/1979 | Dearling | A61L 9/12 239/45 |
| 4,200,229 A | 4/1980 | Spector | |
| 4,235,373 A * | 11/1980 | Clark | A61L 9/14 239/120 |
| 4,341,348 A | 7/1982 | Dearling | |
| 4,346,059 A | 8/1982 | Spector | |
| 4,356,969 A | 11/1982 | Obermayer et al. | |
| D274,040 S | 5/1984 | Ridgley | |
| D285,842 S | 9/1986 | Tigert | |
| D285,843 S | 9/1986 | Tigert | |
| D285,844 S | 9/1986 | Tigert | |
| 4,726,519 A * | 2/1988 | Muoio | A61L 9/14 222/331 |
| 4,889,284 A * | 12/1989 | Spector | A61L 9/12 239/211 |
| D309,943 S | 8/1990 | Jones et al. | |
| D309,996 S | 8/1990 | Gearing | |
| D310,021 S | 8/1990 | Anderson | |
| D318,746 S | 7/1991 | Austin | |
| D326,816 S | 6/1992 | Abrams | |
| D355,712 S | 2/1995 | Barlics | |
| D366,803 S | 2/1996 | Hauser et al. | |
| D380,641 S | 7/1997 | Randle | |
| 5,704,259 A | 1/1998 | Riehle | |
| 5,765,751 A | 6/1998 | Joshi | |
| 5,802,933 A | 9/1998 | Hebert et al. | |
| 5,810,253 A | 9/1998 | Ohayon | |
| 5,849,264 A | 12/1998 | Bassam et al. | |
| 5,899,382 A | 5/1999 | Hayes et al. | |
| D414,060 S | 9/1999 | Talbot-Titley | |
| 6,131,488 A | 10/2000 | Coonrad | |
| D437,040 S | 1/2001 | Soller et al. | |
| 6,202,511 B1 | 3/2001 | Murray et al. | |
| 6,250,181 B1 | 6/2001 | Coonrad | |
| 6,283,337 B1 | 9/2001 | Nakamura et al. | |
| 6,338,424 B2 | 1/2002 | Nakamura et al. | |
| 6,360,477 B1 | 3/2002 | Flashinski et al. | |
| D456,663 S | 5/2002 | Chew | |
| 6,534,079 B1 | 3/2003 | Munagavalasa | |
| D474,109 S | 5/2003 | Owens | |
| 6,569,387 B1 | 5/2003 | Furner et al. | |
| 6,610,254 B1 | 8/2003 | Furner et al. | |
| 6,723,671 B2 | 4/2004 | Zolotarsky et al. | |
| D489,642 S | 5/2004 | Brumlow | |
| D492,600 S | 7/2004 | Moore | |
| D499,796 S | 12/2004 | Walker | |
| D501,248 S | 1/2005 | Chi-Hsiang et al. | |
| D502,365 S | 3/2005 | Dretzka | |
| D508,594 S | 8/2005 | Snell | |
| 6,923,432 B1 | 8/2005 | Martinez | |
| 6,957,779 B2 * | 10/2005 | Joshi | A01M 1/2038 239/37 |
| D515,682 S | 2/2006 | LaBlaine | |
| 7,066,052 B2 | 6/2006 | Chen | |
| 7,134,363 B2 | 11/2006 | Krallman | |
| 7,137,534 B2 | 11/2006 | Patel | |
| 7,149,417 B2 | 12/2006 | Joshi et al. | |
| D538,992 S | 3/2007 | Snell | |
| 7,234,648 B2 | 6/2007 | Tepper et al. | |
| D550,509 S | 9/2007 | Dretzka | |
| D557,073 S | 12/2007 | Snell | |
| D561,929 S | 2/2008 | Meeker et al. | |
| D565,239 S | 3/2008 | Meeker et al. | |
| D565,783 S | 4/2008 | Meeker et al. | |
| D573,917 S | 7/2008 | Bigoski | |
| D575,899 S | 8/2008 | Meeker et al. | |
| D576,759 S | 9/2008 | Meeker et al. | |
| D582,724 S | 12/2008 | Dretzka | |
| D588,852 S | 3/2009 | Stein | |
| 7,549,598 B2 | 6/2009 | Tepper et al. | |
| D596,074 S | 7/2009 | Bodum | |
| D600,547 S | 9/2009 | Cain | |
| 7,600,697 B2 | 10/2009 | Bankers et al. | |
| D604,824 S | 11/2009 | Paolazzi et al. | |
| D612,976 S | 3/2010 | Meeker et al. | |
| D616,139 S | 5/2010 | Meeker et al. | |
| D616,594 S | 5/2010 | Meeker et al. | |
| D620,569 S | 7/2010 | Hall et al. | |
| D625,460 S | 10/2010 | Boissevain | |
| 7,887,759 B2 | 2/2011 | Triplett | |
| D634,415 S | 3/2011 | Abbondanzio et al. | |
| D638,112 S | 5/2011 | Hisey et al. | |
| D639,704 S | 6/2011 | Harshman | |
| 8,047,099 B2 | 11/2011 | John et al. | |
| D651,518 S | 1/2012 | Padain et al. | |
| D652,500 S | 1/2012 | Abbondanzio et al. | |
| D652,661 S | 1/2012 | Lipfert et al. | |
| D659,886 S | 5/2012 | Wauters | |
| D660,940 S | 5/2012 | Flowers et al. | |
| D667,151 S | 9/2012 | Arslanian | |
| 8,261,634 B2 | 9/2012 | John et al. | |
| D672,858 S | 12/2012 | Abbondanzio et al. | |
| D673,252 S | 12/2012 | Abbondanzio et al. | |
| D680,858 S | 4/2013 | Clark et al. | |
| D681,299 S | 4/2013 | Lai | |
| 2005/0275118 A1 | 12/2005 | Chen | |
| 2006/0110297 A1 | 5/2006 | D'Amico et al. | |
| 2007/0057084 A1 | 3/2007 | Vieira | |
| 2007/0140924 A1 | 6/2007 | Hill | |
| 2007/0187524 A1 | 8/2007 | Sherwood | |
| 2007/0230189 A1 * | 10/2007 | Gruenbacher | A61L 9/03 362/311.06 |
| 2007/0295831 A1 * | 12/2007 | Ward | A01M 1/2044 239/47 |
| 2008/0311008 A1 | 12/2008 | Tranzeat | |
| 2009/0121041 A1 | 5/2009 | DeFlorian et al. | |
| 2010/0038609 A1 | 2/2010 | Chen | |
| 2010/0196195 A1 | 8/2010 | Moschel | |
| 2010/0322892 A1 | 12/2010 | Burke | |
| 2011/0120270 A1 | 5/2011 | Lombardi et al. | |
| 2012/0091409 A1 | 4/2012 | Hanlon | |
| 2012/0104027 A1 | 5/2012 | Hoppe et al. | |
| 2012/0108888 A1 | 5/2012 | Spector | |
| 2012/0111966 A1 | 5/2012 | Barlow et al. | |
| 2012/0187217 A1 | 7/2012 | Maget et al. | |

FOREIGN PATENT DOCUMENTS

| | | |
|---|---|---|
| DE | 2540075 A1 | 3/1977 |
| EM | 000025333-0001 | 5/2003 |
| EM | 000048137-0001 | 10/2003 |
| EM | 000147622-0001 | 1/2004 |
| EM | 000146824-0003 | 6/2004 |
| EM | 000232806-0001 | 9/2004 |
| EM | 000126453-0002 | 4/2005 |
| EM | 000364054-0001 | 6/2005 |
| EM | 000364054-0003 | 6/2005 |
| EM | 000364054-0004 | 6/2005 |
| EM | 000407143-0001 | 9/2005 |
| EM | 000457510-0003 | 1/2006 |
| EM | 000601562-0003 | 9/2006 |
| EM | 000834726-0001 | 11/2007 |
| EM | 000889043-0001 | 3/2008 |
| EM | 001596388-0002 | 9/2009 |
| EM | 001660846-0006 | 3/2010 |
| EM | 001693458-0001 | 4/2010 |
| EM | 001928466-0006 | 10/2011 |
| EM | 002051540-0003 | 6/2012 |
| EM | 002079103-0001 | 7/2012 |
| FR | 013047-019 | 9/2001 |
| FR | 013047-023 | 9/2001 |
| FR | 013047-024 | 9/2001 |
| FR | 015603-005 | 12/2001 |
| FR | 096251-002 | 6/2010 |
| GB | 1443314 | 7/1976 |
| GB | 1443314 A | 7/1976 |

(56) References Cited

FOREIGN PATENT DOCUMENTS

| | | |
|---|---|---|
| GB | 3001196 | 3/2002 |
| HU | R01936899 | 10/2011 |
| JP | 2000237643 | 9/2000 |
| JP | 2004091452 | 3/2004 |
| JP | 2004091452 A | 3/2004 |
| JP | 2014-058455 A | 4/2014 |
| PL | 806 | 11/2003 |
| PL | 6239 | 6/2005 |
| PL | 11394 | 11/2007 |
| PL | 14495 | 1/2010 |
| WO | DM/047591 | 3/1999 |
| WO | DM/048626 | 7/1999 |
| WO | DM/052724 | 7/2000 |
| WO | DM/058560 | 8/2001 |
| WO | DM/061226 | 7/2002 |
| WO | DM/062973 | 11/2002 |
| WO | 2004096588 | 11/2004 |
| WO | 2005044320 | 5/2005 |
| WO | 2006002395 | 1/2006 |
| WO | 2006105347 | 10/2006 |
| WO | 2006134353 | 12/2006 |
| WO | 2007062471 | 6/2007 |
| WO | 2008124957 | 10/2008 |
| WO | DM/073042 | 9/2009 |
| WO | DM/074638 | 9/2010 |
| WO | 02083043 | 10/2010 |
| WO | DM/075051 | 10/2010 |
| WO | DM/078953 | 11/2011 |
| WO | DM/077883 | 12/2011 |
| WO | DM/078938 | 2/2012 |
| WO | 2012059771 | 5/2012 |

OTHER PUBLICATIONS

Office Action issued in European Patent Application No. 13 760 147.2, dated Apr. 18, 2016, 12 pages.

* cited by examiner

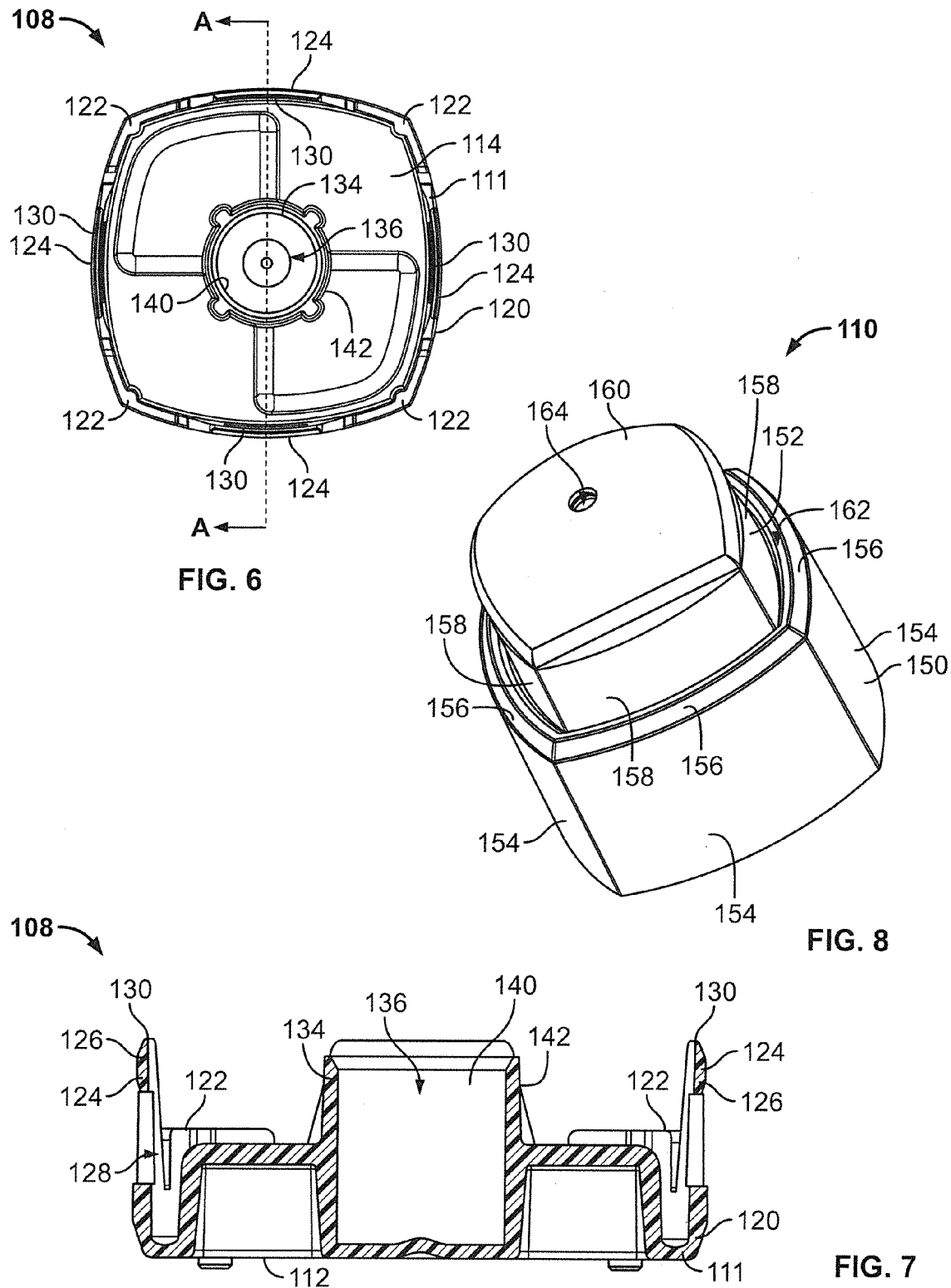

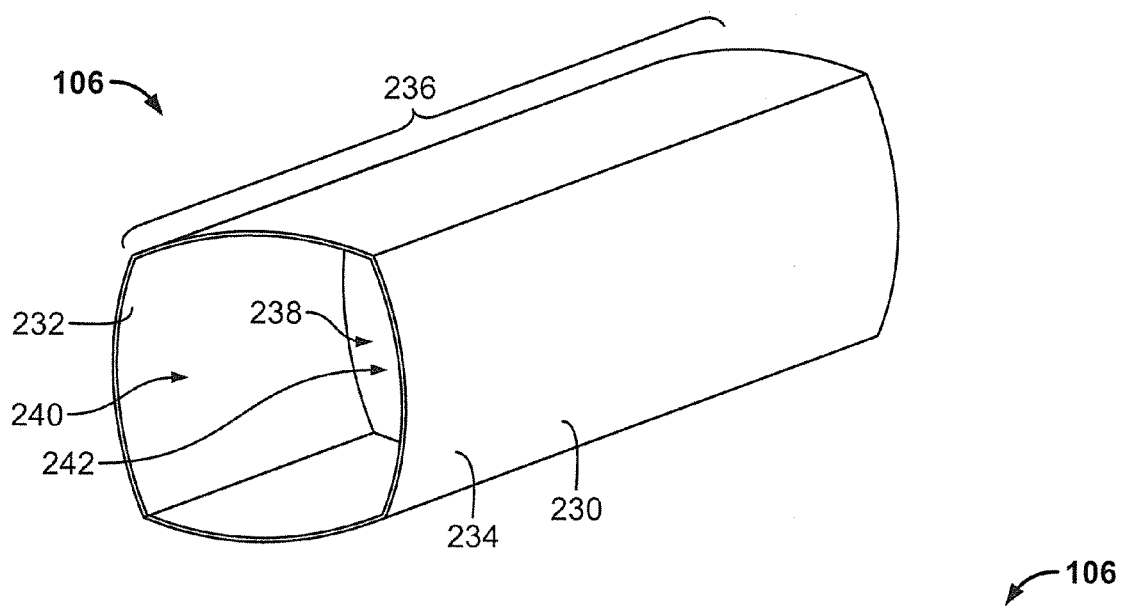
FIG. 17
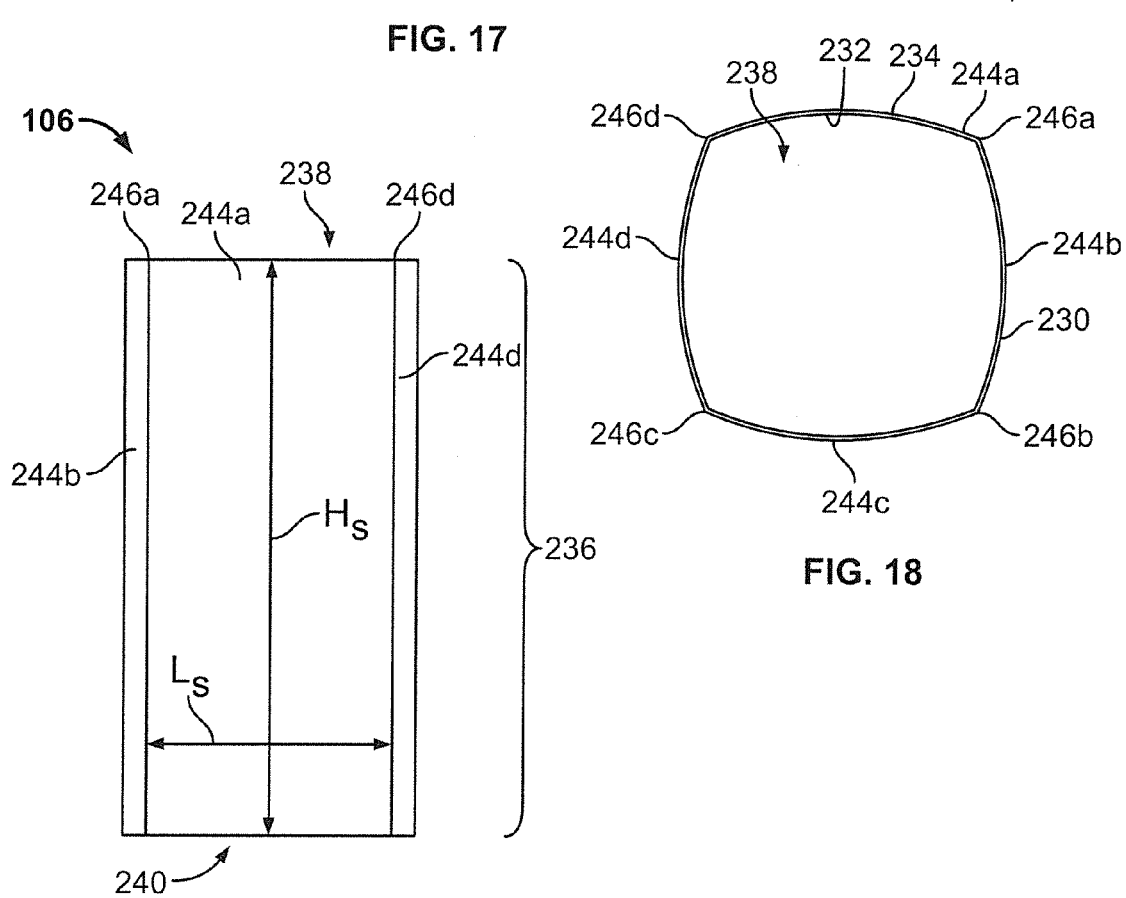
FIG. 18
FIG. 19

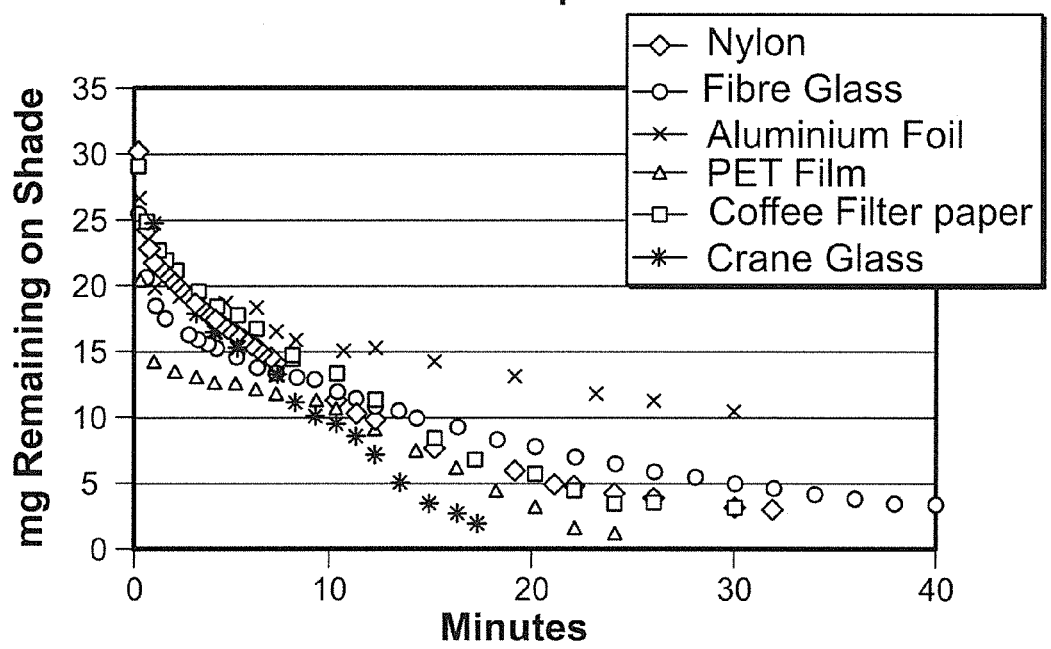
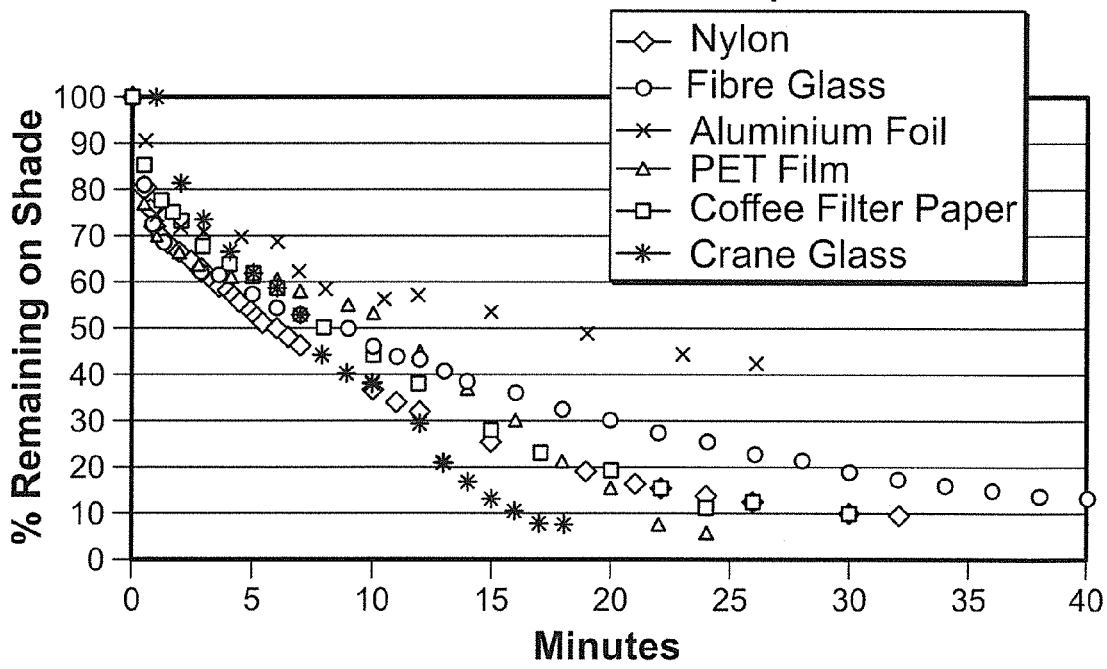
FIG. 24

METHOD AND SYSTEM FOR DISPENSING A COMPOSITION

CROSS REFERENCE TO RELATED APPLICATIONS

This application claims priority to, and is a continuation-in-part of, U.S. patent application Ser. No. 13/588,974 filed on Aug. 17, 2012, and U.S. patent application Ser. No. 13/588,976 filed on Aug. 17, 2012.

REFERENCE REGARDING FEDERALLY SPONSORED RESEARCH OR DEVELOPMENT

Not applicable.

SEQUENTIAL LISTING

Not applicable.

BACKGROUND OF THE INVENTION

1. Field of the Invention

The present disclosure relates generally to a method and system for dispensing a composition, and more particularly, to a dispenser that generates a plurality of use and efficacy indicators as a result of the composition's contact and interaction with the dispenser.

2. Description of the Background of the Invention

Users of consumer products typically purchase a composition to accomplish a specific household task. For example, a user may desire to spray a pest control agent within or outside of a home to control pests. Alternatively, a user may purchase an air freshening device to fragrance and/or deodorize a home. In some instances, it is desirable to dispense a composition instantly, e.g., dispensing a pest control composition onto a pest to exterminate the pest. In other instances, it is desirable to dispense a composition over a prolonged period of time to achieve a desired outcome, e.g., dispensing a fragranced composition in a room of a home to continually provide a pleasant smell therein. In yet other instances, it is desirable to dispense a composition that provides both an instantaneous result followed by an extended action of the same or another composition to accomplish a longer term result.

Unfortunately, many consumer compositions are only active, instant action compositions that are efficacious for a short period of time upon release from a reservoir or are passive, continuous action compositions that are efficacious for prolonged periods of time from a pre-charged substrate. Each system has advantages over the other. For example, active systems enable a user to quickly release a desired amount of an insecticide or a fragrance into the environment to repel/knockdown insects or overcome a strong odor. However, these spikes in composition intensity usually decay rapidly. On the other hand, passive systems typically have a relatively continuous emission of a composition with a more subtle decay in the intensity of the composition compared to active systems.

Some have sought to combine active and passive systems to take advantage of the controlled release of active systems and the sustained release of passive systems. For example, in U.S. Pat. No. 4,341,348, a dispensing device is disclosed that dispenses a spray directly into the air and into an absorbent member. The dispensing device includes an aerosol container and an overcap disposed on a top of the aerosol container. The overcap includes a vented cylindrical sidewall and a vented top portion. A plunger element engages a valve stem on the container and extends through the top portion of the overcap. The plunger includes two ports formed on opposing sides thereof. Two absorbent carrier members are disposed within an upper portion of the overcap around the plunger element. The carrier members are substantially semicircular in cross-section and are spaced around the plunger in such a way as to create two diametrically opposing passageways. Upon activation of the plunger element, fragrance is released out of the ports and through the opposing passageways into the atmosphere. The overcap may also be turned 90 degrees so that the ports and passageways do not align, such that when the plunger is activated spray is released out of the ports directly into the carrier elements. Additional ports may be provided in the plunger so that the spray can be released through the passageways and onto the carrier members simultaneously.

Another device disclosed in U.S. Pat. No. 4,726,519 simultaneously sprays an air-treating composition into the air for instant air treatment and for recharging an absorbent element for continuous air treatment. The device includes an overcap for an aerosol container that includes a cylindrical vented wall and an actuator button with a passageway in communication with a valve stem of the aerosol container. The absorbent member is disposed within the overcap. When the device is activated, the air-treating composition passes a plurality of outlets formed in the passageway before being discharged through a spray orifice and into the air. The plurality of outlets direct a portion of the air-treating composition onto the absorbent member for subsequent passive treatment of the air. A preferred embodiment includes four outlets spaced at 90 degree intervals around the passageway. Alternatively, the outlets could be formed in the valve stem of the aerosol container instead of in the passageway.

Similarly, an additional vapor dispensing device shown in U.S. Pat. No. 7,887,759 includes multiple delivery mechanisms for fragrance release. The dispensing device includes a continuous delivery mechanism with an emanator in communication with a reservoir, for delivering a first continuous passive release of fragrance. The dispensing device also includes an on-demand delivery mechanism for delivering an instantaneous burst of fragrance. Additionally, activation of the on-demand delivery mechanism produces a second continuous passive release of fragrance by depositing a portion of the fragrance burst onto the continuous delivery mechanism or a second surface. The combination of the first and second passive releases creates a release of fragrance that is of a higher intensity than the fragrance released by the continuous delivery mechanism alone.

Another system described in U.S. Pat. No. 6,610,254 includes an aerosol container that is designed to be used immediately (e.g., actively) and utilizes an additional component provided in the form of a separate gel cartridge to provide passive diffusion. This system requires the use of two separate components to accomplish passive and active diffusion, which results in the user having to purchase the separate components to meet their active and passive dispensing needs. The consumer is also required to monitor both components for depletion in order to make sure the system is operating in the correct manner.

One particular obstacle with respect to both passive and active dispensing systems is notification to the user that the composition has been actively released in conjunction with notification that the composition is continuing to provide the desired effect for a time period after the initial release (e.g., passive release). Some prior art systems provide an initial indicator that the composition is in use when the system is first turned on, set-up, or otherwise provided to the user at its initial use stage. In some instances, notification is provided to the user via an audible indicator. In other instances, notification is provided to the user via a visual indicator.

Difficulties arise through the use of some visual and audible indicators, however. For example, in some instances, the audible and visual indicators are transitory and generally do not provide the user any indication of continued efficacy. In other instances, the visual indicators are electronic and provided in the form of an LED or other light. In these systems, the LED is typically provided as a very small bulb that flashes quickly to indicate use. The bulbs may be difficult for some individuals to see due to size constraints on the bulb. Furthermore, bulbs are more expensive and add additional complication and expense to the manufacturing process of the systems.

In other systems, a spray may be generated during actuation. The spray may provide a visual indicator of the active emission status of the system. Unfortunately though, many systems spray into a housing that conceals the spray, and thus, the visual indicator is hidden.

Some prior art systems have attempted to overcome the aforementioned problems through the implementation of a use-up cue associated with the system. In these systems, the use-up cue is provided to indicate the use of a volatile through its life cycle. However, many use-up cues known in the prior art only monitor the passive aspects of the system and do not provide any indication or monitoring of an active aspect of the system.

In addition to the indicators provided by the system, one important aspect to a user's perception of the efficacy of the system is the appearance of and the type of substrate being utilized in the system. In particular, in systems that utilize a substrate having a non-absorbent appearance, users may perceive that a composition will not absorb into the substrate when applied, and will therefore not continually provide passive diffusion thereafter. Indeed, a user's perception of the absorption properties of solid substrates, whether correct or not, provides an indication that the substrate will not be effective in passively releasing the composition. Such systems may also result in ineffective or over-use because of the user's perceived need to overcome the deficiencies of the system by excessive instant spraying.

In contrast, a fabric, cloth, or paperboard-type substrate conjures a completely different perception to a user. For example, most users inherently understand that a composition sprayed onto a fabric-type substrate will first absorb into the substrate and provide an immediate active burst while also continuing to provide prolonged emission after the composition is initially sprayed onto the substrate. A common example familiar to many is when perfume is sprayed onto clothing. The perfume provides an aromatic burst at the time of spraying and the sprayed clothing continues to release aromatics throughout the day, or for a time period after the initial spray period.

Therefore, a need exists for a system that provides both active and passive diffusion from a single component and provides one or more indicators of the active and passive emission states. More preferably, such a system is non-electronic to simplify manufacturing and reduce costs. Further, such systems are also simpler to use and maintain by a user.

There is also a need to provide such a system that minimizes the need for multiple refills. More particularly, it is preferred that such a system only require a single refill that supplies a composition for both active and passive use.

There is a further need to provide a system that allows a user to easily actuate the system to provide both active and passive diffusion through one simple step. Further advantages can be realized when the user wants to refresh the passive diffusion aspect of the system after depletion. In particular, the user simply actuates the system additional times, which results in the system being refreshed and again providing both active diffusion and passive diffusion through one actuation step.

There is also a need to provide effective visual indicators to the user. More particularly, it is preferred that a system utilize portions thereof that effect passive and active diffusion to provide the visual indications of efficacy themselves. In such a system, parts are reduced and the communication of the operation and effectiveness of the system is simplified and intuitive to a user.

SUMMARY OF THE INVENTION

According to one aspect, a dispensing system includes a substrate and a mechanism for discharging a flowable medium through the substrate. The discharge of the flowable medium through the substrate results in a visible plume of the flowable medium for at least 3 seconds. It is also contemplated that the plume of flowable medium may be visible for at least 8 seconds or that the plume is visible beyond a boundary of the substrate for at least one second or for between one second and two seconds. It is further contemplated that the substrate may be absorbent or that the substrate may comprise a shade having a horizontal component and a vertical wall extending upwardly therefrom, wherein the flowable medium is visible as a plume for at least 3 seconds within a channel of the shade. It is also contemplated that the shade circumscribes the mechanism for discharging the flowable medium.

According to another aspect, a dispensing system includes a substrate having a channel and a mechanism for discharging a flowable medium into the channel. The channel comprises an uninterrupted volume of at least 300 cm$^3$, and the discharge of the flowable medium creates a visible plume within the channel. It is also contemplated that the plume is visible beyond a boundary of the substrate and that the substrate may be absorbent. It is further contemplated that the substrate comprises a plurality of non-woven fibers and has a medium pore diameter by volume of at least 50 μm. Still further, the substrate may be nylon.

According to a further aspect, a dispensing system includes a substrate having a channel and a mechanism for discharging a flowable medium into the channel. The discharged flowable medium comprises a particle size distribution that is less than or equal to 30 μm for a Dv(90) particle size distribution at an outlet of the channel.

According to a different aspect, a dispensing system comprises a substrate having a channel with an interior volume of between 300 cm$^3$ to 800 cm$^3$, in which a flowable medium is discharged therein. The flowable medium has a particle size distribution that is less than or equal to 30 μm for a Dv(90) particle size distribution at an outlet of the channel.

According to a further aspect, a dispensing system includes a substrate having a channel with an interior volume of between 300 cm$^3$ to 800 cm$^3$, in which a flowable medium is discharged therein. The flowable medium has a particle size distribution in which at least 15% of the particles are less than 10 μm in size. It is also contemplated that at least 25% of the particles are less than 10 μm in size or that at least 35% of the particles are less than 10 μm in size.

According to one aspect, a dispensing system includes a substrate having a channel and a mechanism for discharging a flowable medium into the channel. The discharged flowable medium comprises a particle size distribution that is less than or equal to 30 μm for a Dv (90) particle size distribution, and the flowable medium creates a plume that is visible for at least 3 seconds.

According to a different aspect, a dispensing system includes a substrate having a conduit with a lower end and an upper end and a mechanism for discharging a flowable medium through the conduit and out of the upper end thereof. The flowable medium forms a plume that exits the upper end of the conduit with a velocity of between about 4 m/s to about 10 m/s, and wherein portions of the plume extend at least 100 mm above the upper end of the conduit. It is also contemplated that the flowable medium may be discharged through at least 75% of a length of the conduit. It is further contemplated that the plume has a velocity of about 0.10 m/s at 100 mm above the upper end of the conduit. It is also contemplated that the flowable medium is dispensed at an angle between about 30 degrees to about 70 degrees relative to a longitudinal axis of the substrate. It is further contemplated that the flowable medium is dispensed from a nozzle actuator having at least four discharge orifices at an angle of about 60 degrees. It is also contemplated that the plume may have a particle size distribution that is less than or equal to 30 μm for a Dv(90) particle size distribution at the upper end of the conduit.

According to another aspect, a dispensing system comprises a substrate having a channel and a mechanism for discharging a flowable medium into the channel. The flowable medium creates a plume that comprises at least 100 mg of liquid particles, and the plume is visible for at least 3 seconds within the channel and at least 1 second outside of the channel.

According to a further aspect, a dispensing system includes a substrate having a channel and a mechanism for discharging a flowable medium into the channel. The substrate also includes a median pore diameter by volume of less than 80 μm.

According to a different aspect, a dispensing system includes a substrate having a channel and a mechanism for discharging a flowable medium into the channel. The channel comprises an uninterrupted volume of at least 400 $cm^3$. The substrate comprises a plurality of non-woven fibers, a median pore diameter by volume of less than 80 μm, and a porosity of at least 1.55 mL/g. It is also contemplated that the substrate may comprise a median pore diameter by volume of between 50 μm to 80 μm and a porosity of between 1.55 mL/g to 7.13 mL/g.

According to another aspect, a dispensing system comprises a substrate having a channel and a mechanism for discharging a flowable medium into the channel. The channel comprises an uninterrupted volume of at least 300 $cm^3$. The substrate comprises a plurality of non-woven fibers, a median pore diameter by volume of less than 80 μm, and a bulk density of less than 1.275 $g/cm^3$. It is also contemplated that the substrate may comprise a median pore diameter by volume of between 50 μm to 80 μm and a bulk density of between 1.142 $g/cm^3$ to 1.273 $g/cm^3$.

According to an additional aspect, a dispensing system includes a substrate having a channel and a mechanism for discharging a flowable medium into the channel. The substrate comprises a plurality of non-woven fibers and a median pore diameter by volume of less than 80 μm, and wherein the substrate has a strip tensile strength of at least 3 N/mm. It is also contemplated that the substrate may comprise a median pore diameter by volume of 75 μm and a strip tensile strength of 3.03 N/mm.

According to a different aspect, a dispensing system includes a substrate having a channel and a mechanism for discharging a flowable medium into the channel. The channel comprises an uninterrupted volume of at least 300 $cm^3$. The substrate comprises a plurality of non-woven fibers and an average mass absorption rate of at least 0.15 $mg/mm^3$. It is also contemplated that the substrate may comprise an average mass absorption rate of between 0.15 $mg/mm^3$ to 0.18 $mg/mm^3$.

According to a further aspect, a dispensing system comprises a substrate having a channel and a mechanism for discharging a flowable medium into the channel. The channel comprises an uninterrupted volume of at least 300 $cm^3$. The substrate comprises a plurality of non-woven fibers and an average wicking speed of at least 0.05 mm/s. It is also contemplated that the average wicking speed may be between 0.050 mm/s to 1 mm/s. It is further contemplated that the substrate may be capable of absorbing about 0.061 $mg/mm^2$ of the flowable medium. Still further, it is also contemplated that a discharge stream of the flowable medium may be discharged onto a surface defining the channel, and wherein an external surface of the substrate is imparted with at least one wet spot that is most visually pronounced about 2 minutes after the discharge of the flowable medium. Also, it is contemplated that at least one discharge stream of the flowable medium may be discharged onto a surface defining the channel, and wherein an external surface of the substrate is imparted with at least one wet spot having an average size of greater than or equal to 8 $cm^2$ ten seconds after the discharge of the flowable medium.

According to a different aspect, a dispensing system comprises a shade and a base for retaining the shade, wherein the discharge of a flowable medium into the shade results in a visible wet spot of the flowable medium on a surface of the shade for a time period $t_1$ and a visible plume of the flowable medium within the shade for a time period $t_2$, and wherein $t_2<t_1$. It is also contemplated that the visible plume of the flowable medium may be visible outside of the shade for a time period of $t_3$, wherein $t_3<t_2$. Further, it is also contemplated that the shade may comprise a nylon and that the visible wet spot is substantially not visible 6 minutes after the discharge of the flowable medium.

According to another aspect, a dispensing system includes an absorbent substrate having a channel and a mechanism for discharging a flowable medium into the channel. The flowable medium comprises a propellant, at least one active ingredient, and a solvent. At least 20 wt. % of the flowable medium discharged into the channel is deposited on the absorbent substrate for passive diffusion therethrough and a majority of the flowable medium is discharged through the channel and into the atmosphere. It is also contemplated that at least 50% of the flowable medium that is deposited on the absorbent structure may remain after 20 minutes.

According to a different aspect, a dispensing system includes an absorbent substrate having a channel and a mechanism for discharging a flowable medium into the channel, a single discharge including up to 200 g of the flowable medium. The flowable medium comprises a propellant, at least one active ingredient, and a solvent. The absorbent structure comprises a plurality of non-woven fibers, a median pore diameter by volume of at least 75 um, a porosity of at least 1.55 mL/g, and a thickness of at least 0.21 mm. The activation of the mechanism between 2-10 times results in a linear absorption and release profile of the flowable medium into and from, respectively, the absorbent substrate.

According to another aspect, a dispensing system comprises a nylon shade having an internal volume and a base in association with the shade, the base being articuable between first and second positions to effect the discharge of a flowable medium into the internal volume of the nylon shade.

According to a further aspect, a dispensing system comprises an absorbent substrate and a mechanism for discharging a flowable medium through the absorbent substrate. The discharging of the flowable medium creates an audible indicator that the flowable medium has been discharged, and wherein discharging of the flowable medium through the absorbent structure creates a first visual indicator in the form of a plume of suspended particles and a second visual indicator in the form of a wetted region of the absorbent structure, which are visible by a user during use of the dispensing system. It is also contemplated that the audible indicator may be at least one of an audible noise from the release of the flowable medium from a valve stem or valve assembly of an aerosol container and an audible noise from the release of the flowable medium from a discharge tube or valve assembly of a pump-type sprayer. It is further contemplated that the audible indicator may be at least one of an audible noise from the release of the flowable medium from a solenoid and an audible noise from a drive mechanism of an automated actuator. Also, it is contemplated that the first visual indicator may have a fog-like appearance and is visible for at least 3 seconds or that the first visual indicator may be visible for between 8 seconds and 16 seconds. It is still further contemplated that the second visual indicator may appear to contrast in color to a surface adjacent thereto or that the second visual indicator may appear darker in color than a surface adjacent thereto. It is contemplated as well that the second visual indicator may provide a visual indication of efficacy for a time period that is greater than that of the first visual indicator. Also, it is contemplated that the audible indicator may be provided prior to the first and second visual indicators.

According to another aspect, a dispensing system includes an absorbent substrate and a mechanism for discharging a flowable medium through the absorbent substrate. The discharging of the flowable medium creates an audible indicator that the flowable medium has been discharged. Further, discharging of the flowable medium through the absorbent structure creates a first visual indictor in the form of a plume of suspended particles and a second visual indicator in the form of a wetted region of the absorbent structure, which are visible by a user during use of the dispensing system.

In yet another aspect, a dispensing system includes a translucent shade having an interior volume and a mechanism for discharging a flowable medium. The discharging of the flowable medium onto the shade imparts a wet spot that is visible for a time period $t_1$, which is longer than a period of time $t_2$ that the flowable medium is visible when suspended in the atmosphere.

According to another aspect, a dispensing system includes a base containing an actuation mechanism for opening a valve of a container and a shade. The base and the shade each comprise one or more of a natural occurring substance, and/or a structure that gives the appearance of being natural looking, and/or a structure having a natural appearing pattern applied thereto. It is also contemplated that a lower end of the shade may be seated on the base and that the shade may comprise an absorbent structure. It is also contemplated that the shade may include a horizontal component and a vertical wall extending upwardly from the horizontal component, the horizontal component and the vertical wall defining an interior volume of the shade.

According to a different aspect, a dispensing system comprises an absorbent substrate having a channel, a base having a discharge mechanism for spraying within the channel of the absorbent structure, and a container in association with the base, including a pressurized fluid therein. Actuation of the discharge mechanism causes fluid from the container to be discharged at an angle that is one or more of not parallel with a longitudinal axis of the container, not parallel with a longitudinal axis of the absorbent structure, and not parallel with a longitudinal axis of the base, and wherein the angle at which the fluid is discharged is not orthogonal to the selected one or more longitudinal axes. It is also contemplated that the discharged fluid may impact a surface defining the channel between a lower end and an upper end thereof and that the fluid may be discharged through a nozzle actuator having at least four discharge orifices. It is also contemplated that the channel may have a volume of at least 400 $cm^3$ and that the channel may have a volume of at least 300 $cm^3$ to 800 $cm^3$. Further, it is contemplated the channel may have a volume of at least 200 $cm^3$ to 700 $cm^3$ when the absorbent structure is retained on the base.

According to another aspect, a dispensing system comprises a substrate having a channel, a base having a discharge mechanism for spraying within the channel of the substrate, and a container in association with the base, including a pressurized fluid therein. The channel includes a length dimension of at least 100 mm and a smallest cross-sectional width of no more than 20 mm. It is also contemplated that the cross-sectional width of the channel may be substantially uniform between a lower end and an upper end thereof. Further, it is contemplated that the sprayed fluid may be discharged within the channel and that at least a portion of the fluid impacts a surface of the substrate at least 70 mm from a lower end thereof. It is also contemplated that the substrate may have a length dimension of at least 170 mm. It is still further contemplated that the channel may have a volume of at least 300 $cm^3$. It is contemplated as well that the fluid may be discharged to impact a surface defining the channel and that the fluid may impact the surface at an angle other than orthogonal to the surface.

According to one aspect, a dispensing system includes a first audible indicator. The dispensing system also includes a first and a second visual indicator, wherein the visual indicators are not electronic.

According to still another aspect, a dispensing system includes a substrate and a mechanism for discharging a flowable medium through the substrate. The discharge of the flowable medium through the substrate results in a visible plume of the flowable medium having a droplet density of at least 15,000 droplets/$cm^2$ within the substrate. It is also contemplated that the substrate.

According to still another aspect, a dispensing system includes a substrate having a channel and a mechanism for discharging a flowable medium through the channel of the substrate. The mechanism includes at least one discharge orifice having a diameter of between about 0.1 mm to about 1.0 mm. The discharge of the flowable medium through the channel is directed at an angle of between about 30 degrees to about 70 degrees measured about a longitudinal axis of the substrate. It is also contemplated that the diameter of the discharge orifice may be about 0.5 and/or that the flowable medium through the channel may be directed at an angle of between about 50 degrees to about 70 degrees. It is further contemplated that the discharge of the flowable medium through the channel creates a visible plume.

According to another aspect, a dispensing system includes a shade and a base for retaining the shade. The shade circumscribes a portion of the base and the discharge of a pest control agent into the shade results in a visible wet spot on a surface of the shade.

BRIEF DESCRIPTION OF THE DRAWINGS

FIG. 6 is a top plan view of the lower housing of FIG. 3;

FIG. 7 is a cross-sectional view of the lower housing of FIG. 6 taken along the line A-A of FIG. 6;

FIG. 8 is a top isometric view of the upper housing of FIG. 3;

FIG. 17 is an isometric view of one embodiment of a sleeve for use in a dispenser;

FIG. 18 is a top plan view of the sleeve of FIG. 17;

FIG. 19 is side elevational view of the sleeve of FIG. 17;

FIG. 24 depicts graphs representing a combined evaporation plot for various materials;

DETAILED DESCRIPTION

The present disclosure is generally directed toward dispensers for dispensing a flowable medium. For purposes of discussion herein, a particular exemplary embodiment will be expounded upon, which utilizes an aerosol-based volatile active-containing composition. However, it should be understood that the disclosed systems, regardless of whether described in connection with an aerosol, a volatile, a composition, etc., are not so bound and may be utilized with any number of liquids or fluids, which may be discharged by one or more of an aerosol system, a compressed gas system, a pump-type sprayer system, or any other means as known to one of ordinary skill.

Figure 2:
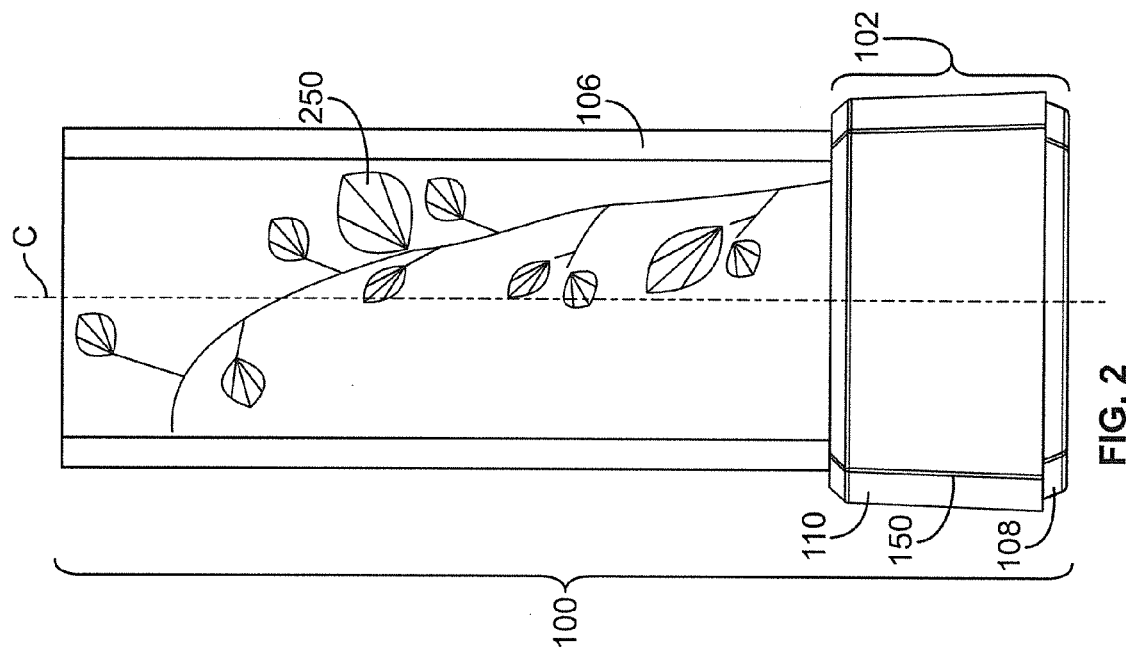
FIG. 2 is a front elevational view of the dispenser of FIG. 1, the left, right, and rear elevational views being substantially the same.
Figure 1:
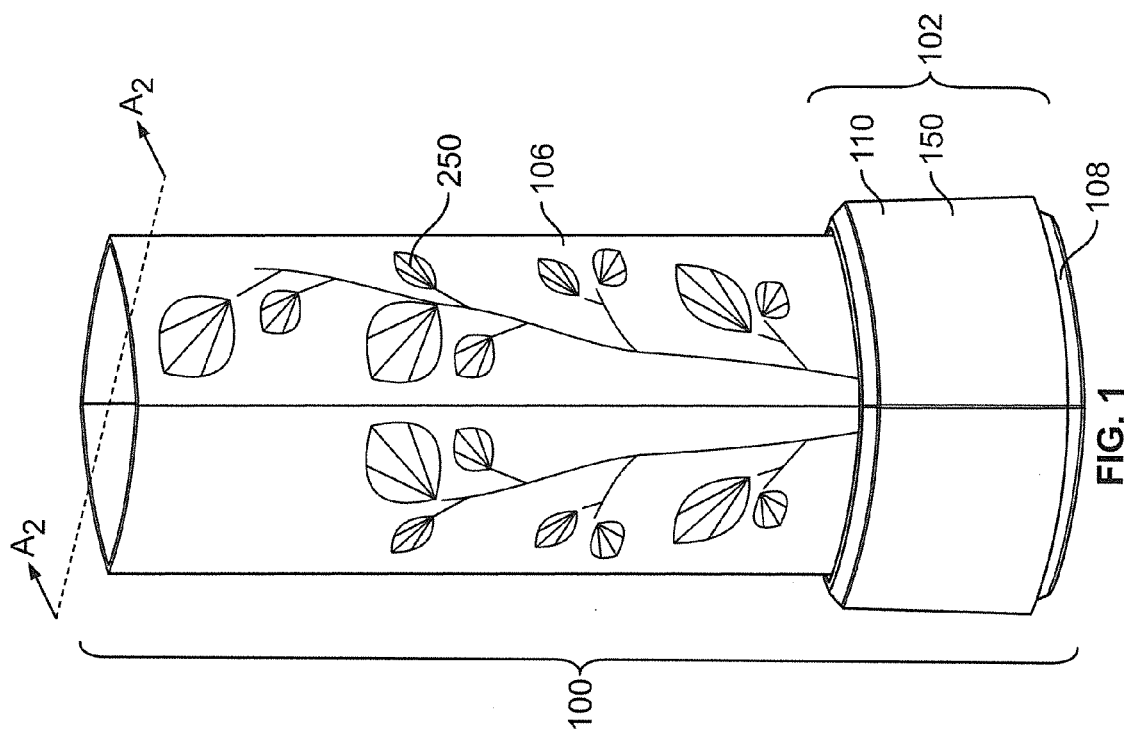
FIG. 1 is an isometric view of a dispenser according to a first embodiment.
Figure 3:
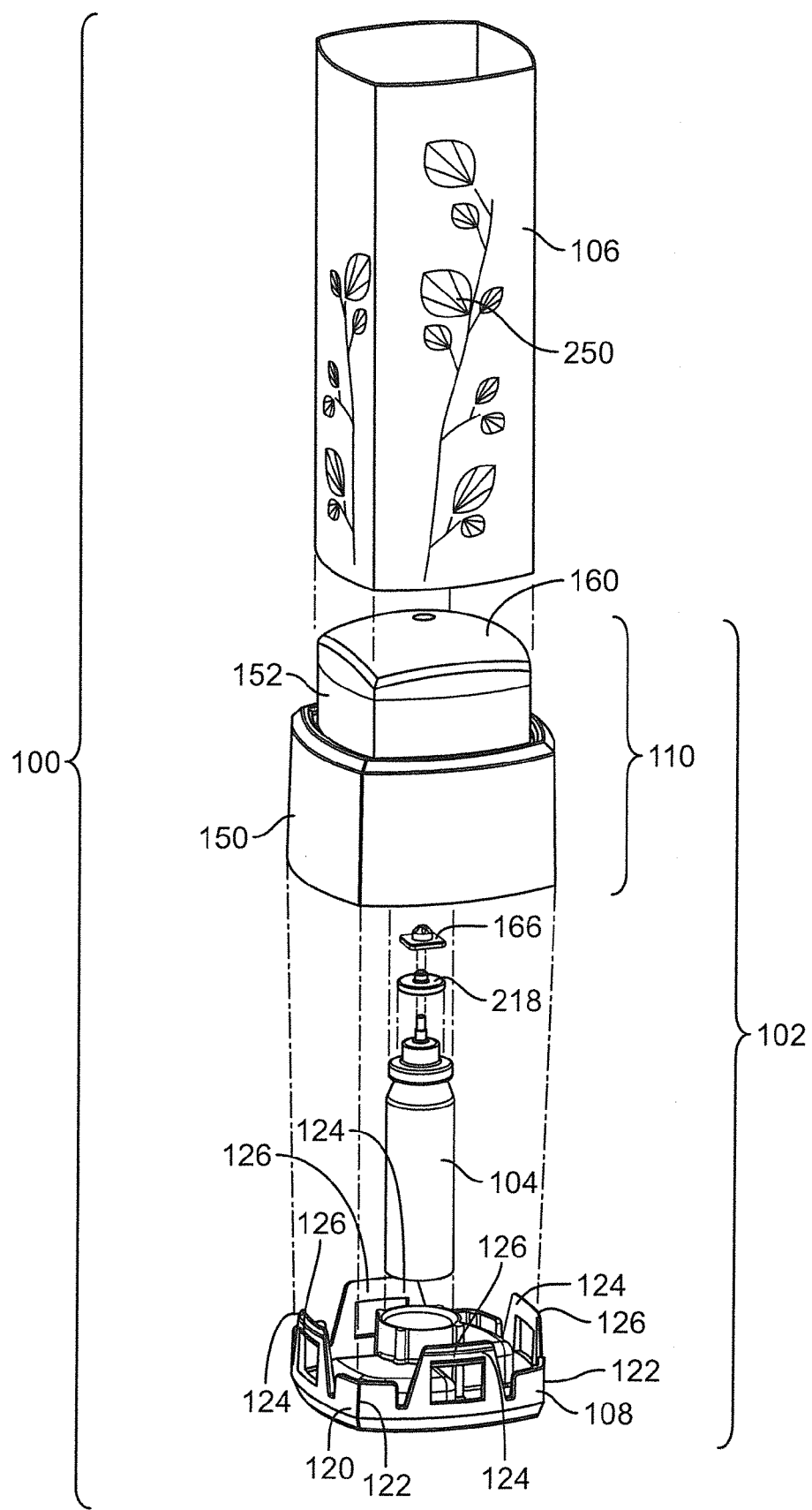
FIG. 3 is an exploded isometric view of the dispenser of FIG. 1 including a base having an upper and a lower housing, a container, and a sleeve.

The dispensers described herein may be used as stand-alone devices, which may be placed on a table, shelf, or other flat surface. Alternatively, the dispensers may be utilized as a hand-held device. With reference to FIGS. 1-3, one particular embodiment of a dispenser 100 is illustrated that generally includes a base 102 designed to accommodate a container 104 with a flowable medium (not shown). The dispenser 100 further includes a sleeve 106 that extends upwardly from the base 102.

The dispenser 100 is generally designed to be manually actuated via pressure applied to the base 102. The base 102 therefore acts as (or includes) an actuation mechanism for discharging the flowable media therethrough and may include any number of activators or actuators to effect dispensing. In particular, during actuation, the flowable medium sprays into the sleeve 106 at a specified angle, which causes a plurality of droplets to interact with the sleeve 106 to provide different functionalities to the dispenser 100, such as the active and passive emission of a composition or volatile material. More particularly, some droplets are released immediately to form a plume that is initially present within and/or above the sleeve 106 to provide an instant active emanation, and other droplets are absorbed into the sleeve 106 to provide passive emanation over an extended amount of time.

With specific reference to FIG. 3, the base 102 is defined by a lower housing 108 that is releasably attached to an upper housing 110. The lower housing 108 and upper housing 110 are in communication when the dispenser 100 is being used and are designed to be separated from each other when the container 104 is added or removed therefrom. The base 102 further acts as a manual actuation mechanism for the dispenser 100 due to the unique construction thereof, which is described in detail below.

Each of the components of the dispenser 100, including the base 102, may have a generally square shape with slightly rounded curvature imparted to each side thereof, when viewed from above or below (see, e.g., FIG. 6), but may also be circular, elliptical, triangular, or any other geometric shape consistent with the properties described herein.

The base 102 may be constructed from any suitable material, such as a plastic, a polymer, a fabric, a non-woven substrate, such as a PET non-woven substrate, a cellulosic material, a metal, glass, wood, stone, rock, or combinations thereof. Additionally, the materials may include combinations of manufactured, natural, and/or recycled or reclaimed materials. One consideration for the consumer is the appearance of the base 102, which preferably has a natural look, such as a smooth or textured rock or pebble. The curvilinear sides may also be provided with a natural looking pattern, such as a wood grain, a stone pattern with or without inclusions, a fossil pattern, etc.

As best seen in FIGS. 4-7, the lower housing 108 of the base 102 includes a substantially flat sidewall 111 defined by an exterior surface 112 and an opposing interior surface 114. The exterior surface 112 is designed to be positioned adjacent a support surface (not shown) and the interior surface 114 is enclosed via the upper housing 110 when the dispenser 100 is in use.

Figure 4:
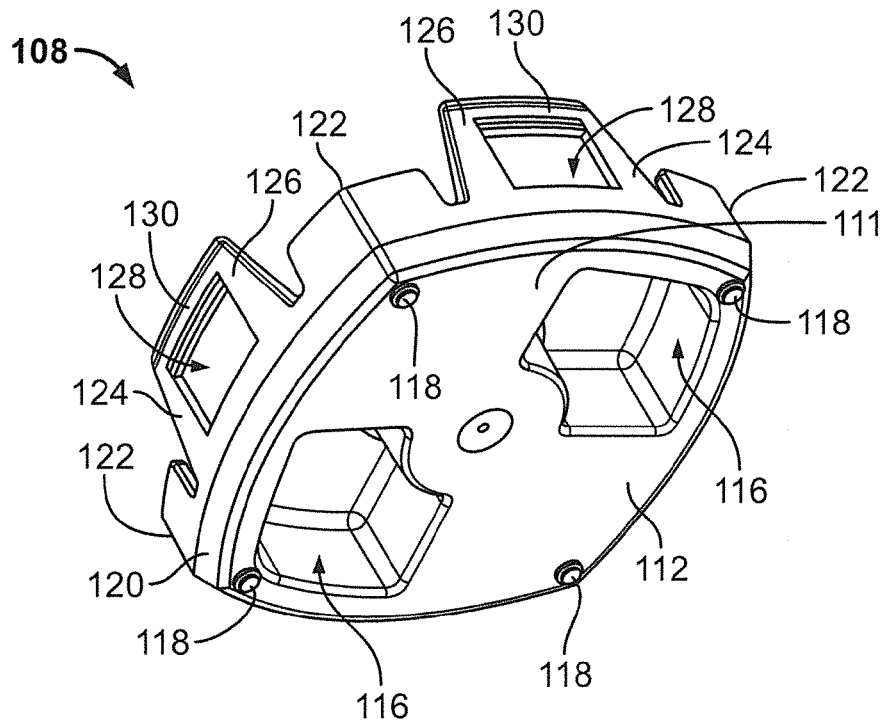
FIG. 4 is a bottom isometric view of the lower housing of FIG. 3.

Referring to FIG. 4, the exterior surface 112 of the lower housing 108 includes two opposing curved grooves 116 formed therein. The grooves 116 define finger grips to assist a user in grasping the lower housing 108 when the user separates the lower housing 108 from the upper housing 110. The curvature imparted to the grooves 116 is designed to correspond with natural placement of a user's fingers therein (e.g., a thumb disposed within one groove and an index and middle finger disposed together in the opposing groove). A plurality of feet 118 optionally extend from the exterior surface 112 to create a slight gap between the base 102 and a support surface.

Figure 5:
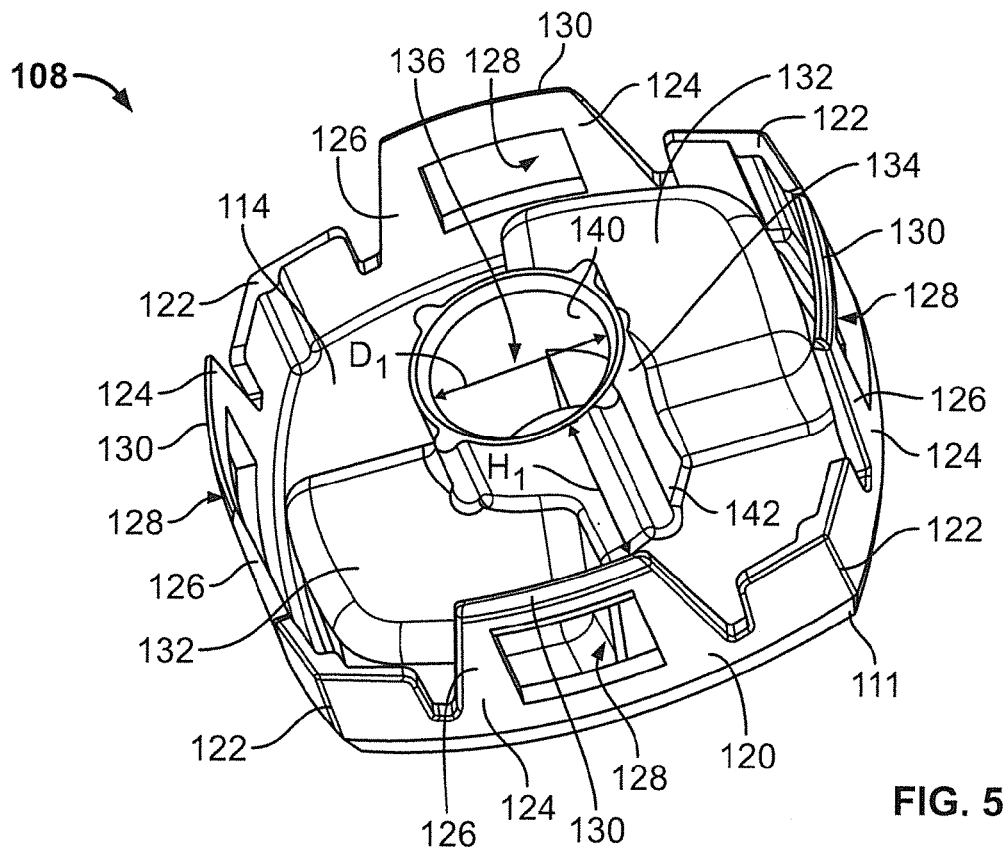
FIG. 5 is a top isometric view of the lower housing of FIG. 3.

As depicted in FIGS. 4, 5, and 7, the lower housing 108 further includes an upwardly extending sidewall 120 circumscribing the perimeter thereof. The sidewall 120 is slightly rounded and is defined by winged corners 122 and a plurality of substantially upwardly extending U-shaped flexible members 124. The winged corners 122 are slightly angled and are disposed in all four corners of the lower housing 108. The U-shaped flexible members 124 are generally centrally disposed along the sidewall 120 and are spaced inwardly from each of the corners 122. The members 124 each include a substantially U-shaped flange 126 defining a substantially square opening 128. A horizontal section 130 of the flange 126 is slightly tapered to provide a guiding function when the upper housing 110 is attached to the lower housing 108.

As seen in FIG. 5, the lower housing 108 also includes two arcuate raised protrusions 132 extending upwardly from the interior surface 114. The protrusions 132 define the boundaries of the grooves 116 formed in the exterior surface 112 of the sidewall 111. A centrally disposed pedestal 134 extends upwardly from an approximate center point of the interior surface 114. The pedestal 134 is substantially cylindrical and includes a circular opening 136 therein. Opposing sections of the protrusions 132 are in communication with the pedestal 134 forming a contiguous structure along the interior surface 114 of the lower housing 108.

One function of the pedestal 134 is to act as a receiving and a retaining mechanism for the container 104. To provide the proper support to the container 104, the pedestal 134 and corresponding opening 136 are preferably shaped to correspond to the shape of the container 104. In the embodiment shown, the pedestal 134 is substantially cylindrical and the opening 136 is circular to correspond to a cylindrical container 104. Additionally, the pedestal 134 preferably includes a suitable height dimension $H_1$ (see FIG. 5) as measured from the interior surface 114 to the upper edge of the pedestal 134 with respect to a height dimension $H_2$ (see FIG. 16) of the container 104 to provide sufficient support. In one embodiment, the ratio of $H_1$ to $H_2$ is about one to about one. In another embodiment, the ratio of $H_1$ to $H_2$ is about one to about two. In a further embodiment, the ratio of $H_1$ to $H_2$ is about one to about three. In another embodiment, the ratio of $H_1$ to $H_2$ is about one to about four. In a further embodiment, the ratio of $H_1$ to $H_2$ is greater than about one.

The pedestal 134 further includes a diameter dimension $D_1$ sufficient to accommodate the container 104. In one embodiment, the diameter is between about 10 mm to about 100 mm and in another embodiment is between about 16 mm to about 67 mm. In another embodiment, the diameter is about 20 mm. The diameter $D_1$ of the pedestal 134 is slightly larger than the diameter dimension $D_2$ of the container 104 such that a gap is formed between the container 104 and an interior surface 140 of the pedestal 134. In one embodiment, the gap is less than about 10 mm. In another embodiment, the gap is less than about 5 mm. In a further embodiment, the gap is less than about 2 mm. In other embodiments, the pedestal 134 may be omitted and other retaining mechanisms may be utilized to support the container 104 in the lower housing 108.

The pedestal 134 is provided interiorly from the perimeter of the lower housing 108. More particularly, the pedestal 134 is spaced from the sidewall 120 of the lower housing 108 a distance of between about 2 mm to about 60 mm around the circumference thereof, as measured from an exterior surface 142 of the pedestal 134 to the sidewall 120. In one embodiment, the pedestal 134 is spaced from the sidewall 120 of the lower housing 108 a distance of at least about 24 mm.

Figure 9:
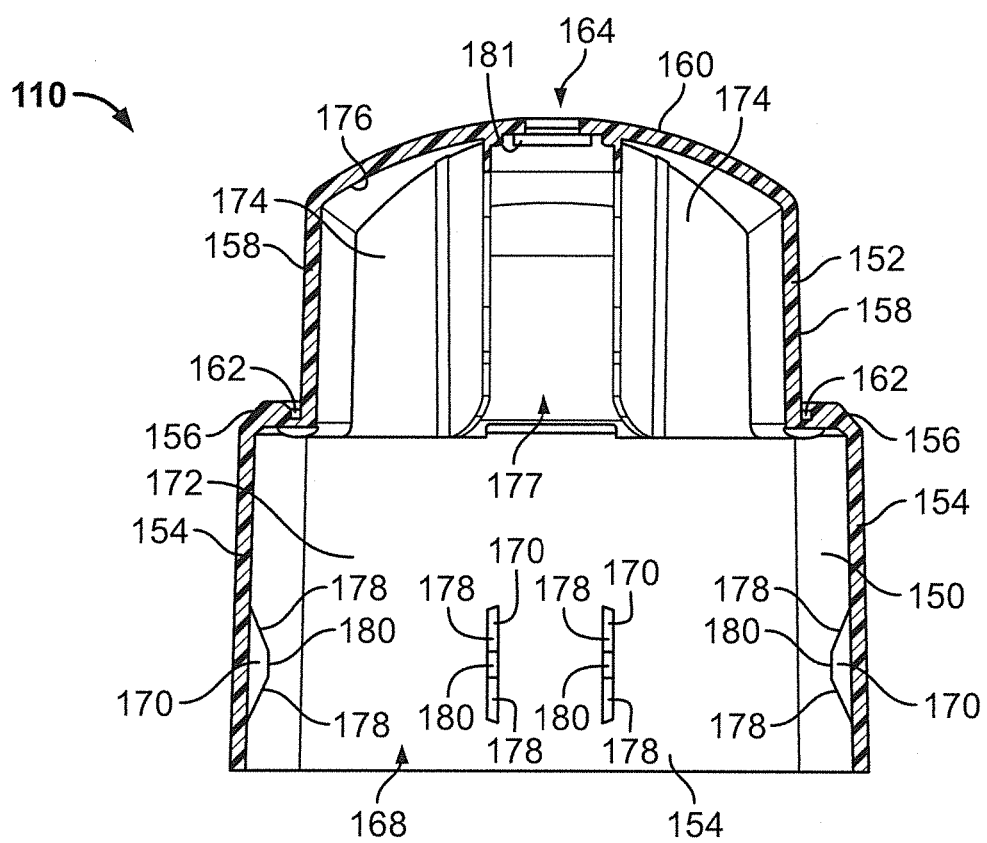
FIG. 9 is a cross-sectional view of the upper housing of FIG. 8 taken along the line $A_1$-$A_1$ of FIG. 10.
Figure 10:
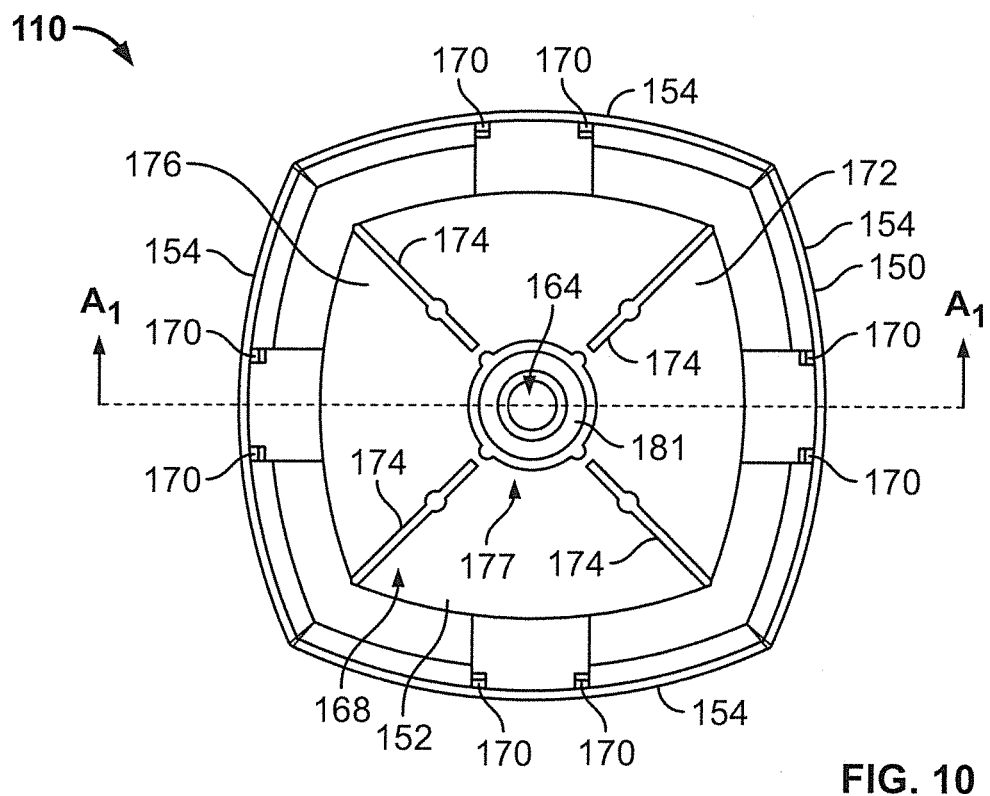
FIG. 10 is a bottom plan view of the upper housing of FIG. 8.

Now turning to FIGS. 8-10, the upper housing 110 is defined by a shroud 150 with a dome 152 integral therewith and protruding upwardly therefrom. The upper housing 110 is designed to act as a manual actuation mechanism (e.g., push button) through its interaction with the container 104 and the lower housing 108. The upper housing 110 also acts to cover internal components of the dispenser 100 such as the container 104.

The shroud 150 includes four slightly rounded lower sidewalls 154 with beveled upper edges 156. The dome 152 is inset from the edges 156 and includes four upwardly extending sidewalls 158 that terminate at a convex upper surface 160. In the embodiment depicted in FIGS. 8-10, the sidewalls 158 of the dome 152 are similar in shape to the lower sidewalls 154 of the shroud 150. The inset orientation of the sidewalls 158 of the dome 152 create a recess 162 extending therearound. In particular, the recess 162 extends between the edges 156 of the lower sidewalls 154 and the sidewalls 158 of the dome 152.

The recess 162 is preferably dimensioned to accommodate the sleeve 106, as described in more detail hereinbelow. In the embodiment depicted, the recess 162 includes a depth dimension of about 2 mm and a width dimension of about 1 mm. In other embodiments, the recess 162 includes a depth dimension of about 25 mm and a width dimension of about 1 mm. In further embodiments, the recess 162 includes a depth dimension of 0 mm and a width dimension of 0 mm, i.e., the recess is absent. However, it is anticipated that the depth of the recess 162 could be between about 0 mm to about 25 mm and the width of the recess could be about 0 mm to about 25 mm.

Still referring to FIGS. 8-10, the dome 152 further includes a circular opening 164 that extends through the upper surface 160. The opening 164 is sized to receive an actuator nozzle 166, (see FIG. 11) which provides fluid communication between the container 104 and the environment external to the base 102, as described in more detail below.

The lower sidewalls 154 of the shroud 150 define an aperture 168 (see FIG. 9) that receives the lower housing 108 when the dispenser 100 is in use. As depicted in FIG. 9, a plurality of elongate protrusions 170 extend outwardly from an internal surface 172 of the shroud 150 and four stabilizing ribs 174 protrude outwardly from an internal surface 176 of the dome 152. The protrusions 170 each include two opposing angled end portions 178 connected via a substantially flat portion 180. In the embodiment depicted, two protrusions 170 extend outwardly from the internal surface 172 of each sidewall 154, defining eight total protrusions. The protrusions 170 are spaced from each other a distance of about 0 mm (e.g., when there is only one rib) to about 60 mm.

Figure 11:
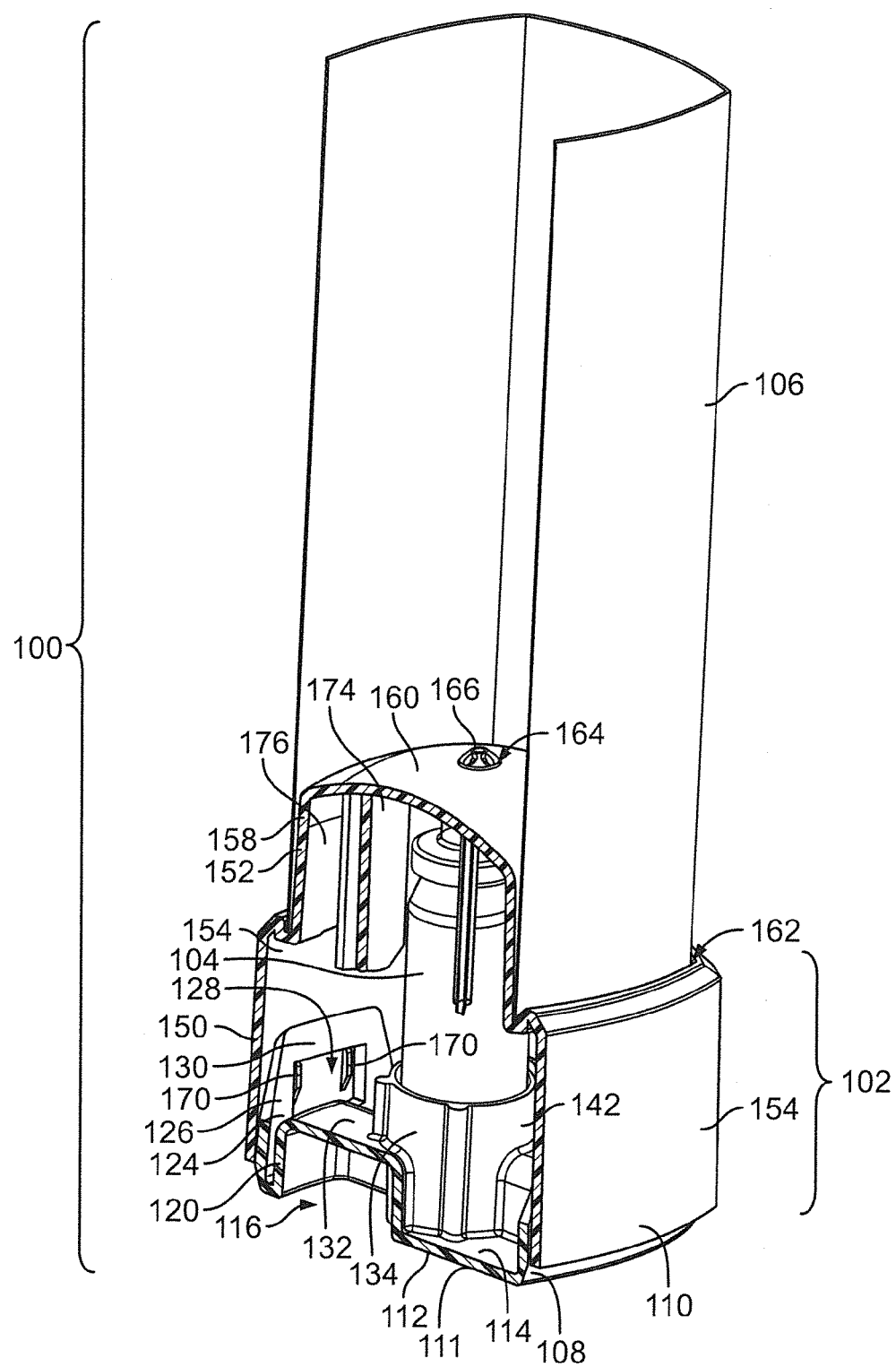
FIG. 11 is a partial cross-sectional view of the dispenser of FIG. 1 taken along the line $A_2$-$A_2$ of FIG. 1.

As shown in FIGS. 9 and 11, the protrusions 170 are centrally disposed and designed to interact with the U-shaped members 124. In particular, the interaction between the protrusions 170 and the square opening 128 of each of the U-shaped members 124 releasably mate the lower housing 108 to the upper housing 110 when the protrusions 170 are disposed within the openings 128. Although the protrusions 170 are elongate and are provided with a space therebetween, it is envisioned that protrusions 170 having other shapes and dimensions may be provided on the shroud 150 that are consistent with differently shaped openings 128 of the U-shaped members 124 to accomplish the releasable mating of the lower and upper housings 108, 110.

As best seen in FIG. 10, the four rigid ribs 174 protrude outwardly from the internal surface 176 of the dome 152. The ribs 174 extend inwardly from the corners of the dome 152 toward a central portion thereof before terminating at an area adjacent the dome 152 center. The ribs 174 provide stability to the dome 152 and extend substantially the entire length of the dome 152. The ribs 174 also act as a guiding mechanism when the lower housing 108 of the base 102 is being mated with the upper housing 110. In particular, a space 177 is formed between the ribs 174 that is provided in the outline of the container 104 such that the container 104 is able to contact the ribs 174 and slide therebetween during insertion.

Figure 12:
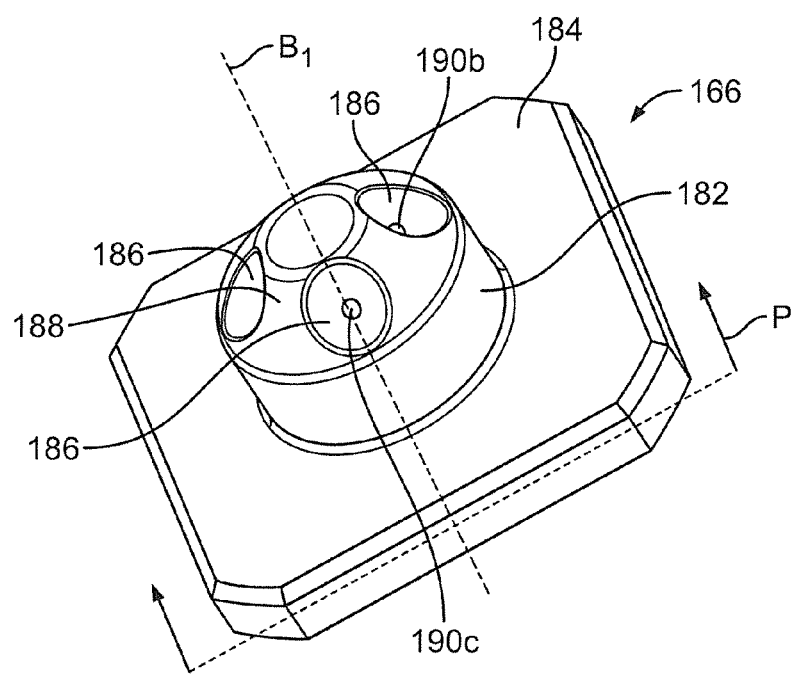
FIG. 12 is a top isometric view of an actuator nozzle for use in the dispenser of FIG. 1.

A raised circular surface 181 (see FIG. 9) protrudes inwardly into the dome 152 and circumscribes the circular opening 164 that extends therethrough. The surface 181 is flat to accommodate a portion of the container 104 as described in more detail below. As best seen in FIG. 12, the opening 164 is sized to receive a portion of the actuator nozzle 166.

Now referring to FIGS. 12-15, the actuator nozzle 166 is provided in the form a conical body 182 with a collar 184 that circumscribes the body 182 around a lower edge thereof. The nozzle 166 further includes a plurality of depressions 186 in an exterior surface 188 thereof and a plurality of outlet ports 190 disposed in and extending through the depressions 186. The outlet ports 190 each provide a fluid pathway and act as an exit orifice for a flowable medium being emitted from the dispenser 100. Each outlet port 190 is substantially circular and splits the composition as it exits from the base 102 into a plurality of streams, for example, 2, 3, 4, or 6 streams.

As depicted in FIG. 12, the outlet ports 190 are disposed equidistant from each other around a vertical axis $B_1$ defined by a centerpoint of the actuator nozzle 166 and the longitudinal axis $B_2$ of the container 104 (see FIG. 16) both radially and circumferentially. However, with reference to FIG. 16, it may be seen that the outlet ports 190 may be radially equidistant, but circumferentially non-equidistant. Indeed, any number of arrangements are contemplated based on the desired flow characteristics of the dispensed medium.

Figure 13:
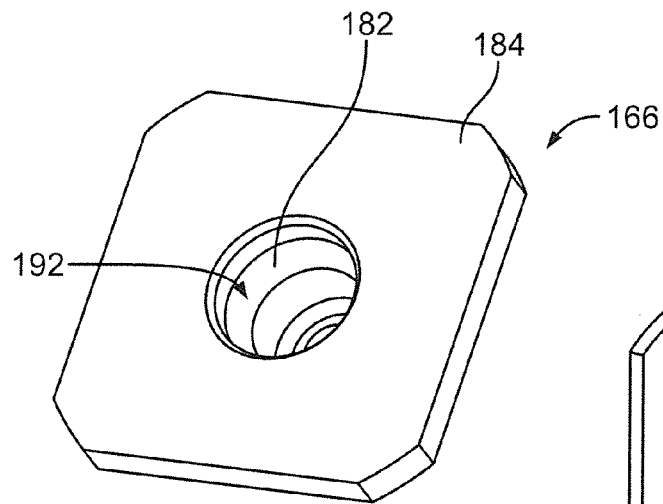
FIG. 13 is a bottom isometric view of the actuator nozzle of FIG. 12.
Figure 14:
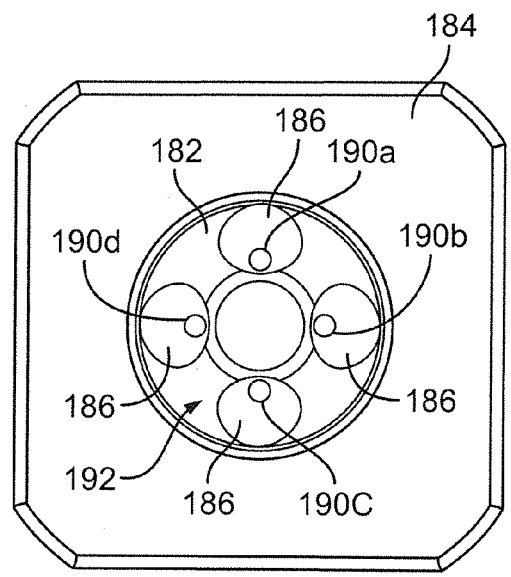
FIG. 14 is a bottom plan view of the actuator nozzle of FIG. 12.

In the embodiment shown in FIGS. 12-14, four outlet ports 190a-190d are depicted. In the embodiment shown in FIG. 15, six outlet openings 190e-190j are depicted. The outlet ports 190 are each defined by a diameter parameter of between about 0.1 mm to about 1 mm. In other embodiments, the outlet ports 190 are each defined by a diameter parameter between about 0.2 mm to about 0.7 mm. In other embodiments, the outlet ports 190 are each defined by a diameter parameter of about 0.25 mm. In further embodiments, the outlet ports 190 are each defined by a diameter parameter of about 0.4 mm. In other embodiments, the outlet ports 190 are each defined by a diameter parameter of about 0.5 mm. In further embodiments, the outlet ports 190 are each defined by a diameter parameter of about 0.6 mm. In a preferred embodiment, the outlet ports 190 have a uniform cross-section and diameter (or width) throughout the entirety thereof. In other preferred embodiments, the outlet ports may have a non-uniform cross-section and/or diameter (or width) through all or a portion thereof. Further, in other preferred embodiments, one or more of the ports may have varying cross-sectional and/or diameter (or width) parameters.

Each outlet port 190 is oriented at an angle with respect to a horizontal plane P defined by the collar 184 (see FIG. 12). Generally, the plane P may be viewed as a plane orthogonal to the vertical axis $B_1$. In particular, the outlet openings 186 are disposed at an angle such that a majority (e.g., greater than 75%) of the flowable medium sprays in a cone-shape at an angle of greater than about 30 degrees with respect to the plane P. Such a cone angle is one factor for accomplishing various indicator features of the dispenser 100 described herein. In particular, the cone angle determines the area that is initially wetted through direct contact with the spray. A small cone angle (e.g., less than about 30 degrees) results in a small area exposed to spray and a thicker layer of medium sprayed onto the sleeve 106. In contrast, a larger cone angle (e.g., greater than or equal to about 30 degrees) results in a larger spray area and a thinner layer of medium sprayed onto the sleeve 106. In some instances, the cone angle is minimized to create a deeper, more concentrated wetted area (i.e., visual indicator) on the sleeve 106. In other instances, a larger section of the sleeve 106 will be contacted using a larger cone angle.

The outlet ports 190 may each have a cone angle of between about 30 degrees to about 80 degrees. In another embodiment, the outlet ports 190 may each have a cone angle of between about 40 degrees to about 70 degrees. In a further embodiment, the outlet ports 190 may each have a cone angle between about 50 degrees to about 70 degrees. In one specific embodiment, the outlet ports 190 each have a cone angle of about 45 degrees. In another embodiment, the outlet ports 190 each have a cone angle of about 50 degrees. In a further embodiment, the outlet ports 190 each have a cone angle of about 55 degrees. In a different embodiment, the outlet ports 190 each have a cone angle of about 60 degrees. Indeed, it is envisioned that a cone angle may be anywhere between about 1 degree to about 180 degrees, more preferably about 5 degrees to about 90 degrees, more preferably about 10 degrees to about 50 degrees, and most preferably between about 10 degrees to about 20 degrees.

As shown in FIG. 13, the outlet ports 190 extend through the body 182 and are in communication with a chamber 192 formed thereby. The chamber 192 is designed to interact with and receive the flowable medium dispensed by the container 104 and directs the medium through the outlet ports 190.

To dispense the flowable medium effectively, the chamber 192 has a volumetric capacity of about 0 $mm^3$ to about 216 $mm^3$. In one embodiment, the volumetric capacity of the chamber 192 is about 27 $mm^3$. In another embodiment, the volumetric capacity of the chamber 192 is about 64 $mm^3$. In a further embodiment, the volumetric capacity of the chamber 192 is about 125 mm³. In some embodiments it is preferred to minimize the volume within the chamber 192 to approach or reach zero.

In one embodiment, the actuator nozzle 160 may have a conical opening defined by a cone angle, as discussed herein. In other embodiments, the actuator nozzle 160 may have a flat surface with an orifice. It is also contemplated that the actuator nozzle 160 may include one or more spray inserts known in the art that may impart a shaped spray pattern such as a fan shape, oval shape, square shape, donut shape, and the like. Further, depending the specific design of the actuator nozzle 160, the angle of the direction of spray being emitted from the actuator nozzle 160 may be adjusted accordingly. For example, the spray may be sprayed perpendicular to plane P (see FIG. 12). In another embodiment, the spray may be dispensed in a manner perpendicular to the sleeve upwardly and downwardly (e.g., 60 degrees upwardly and 60 degrees downwardly).

In one embodiment, one or more outlet ports 190 have a diameter of about 0.5 mm. In another embodiment, one or more of the outlet ports 190 have a diameter of about 0.25 mm. In a further embodiment, one or more of the outlet ports 190 have a diameter of about 0.75 mm. In an additional embodiment, one or more of the outlet ports 190 have a diameter of about 1 mm. It is also contemplated that an outlet port may have a diameter of between about 0.1 mm to about 2 mm. It should be appreciated that as the size of the outlet port increases, a more significant portion of the flowable product will be deposited on the sleeve 106, assuming the dispensing pressure of the container 104 has not been adjusted to accommodate the larger sized outlet ports 190. Alternatively, using smaller sized outlet ports (e.g., less than about 0.4 mm) will cause more of the flowable product to be dispensed within the plume, as opposed to on the sleeve 106. Actuator nozzles 160 having larger sized outlet ports 190 may be utilized in other embodiments. However, in these embodiments, the product medium may need to be discharged at a higher angle with respect to the longitudinal axis of the container 104 to effectively deposit the flowable medium onto the sleeve 106.

Figure 16:
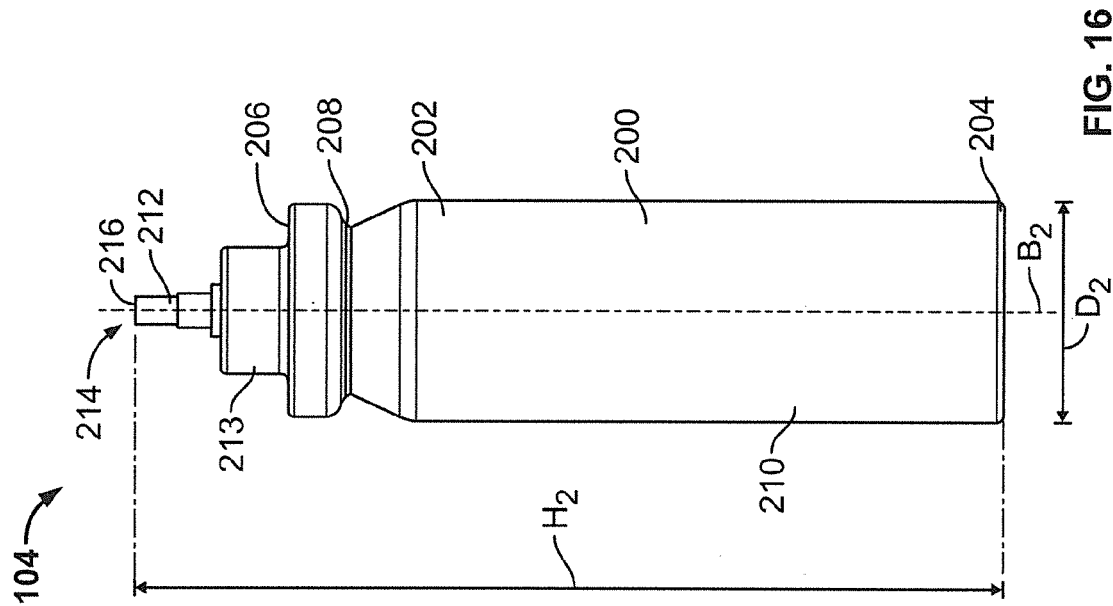
FIG. 16 is a side elevational view of the container of FIG. 3.
Figure 15:
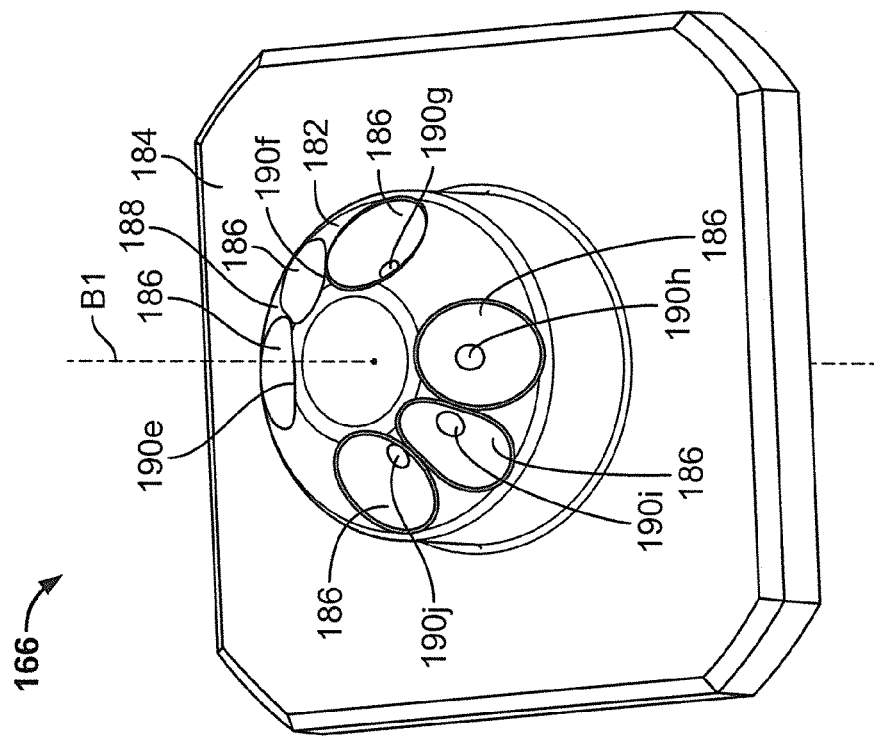
FIG. 15 is an isometric view of a different embodiment of an actuator nozzle.
Figure 20:
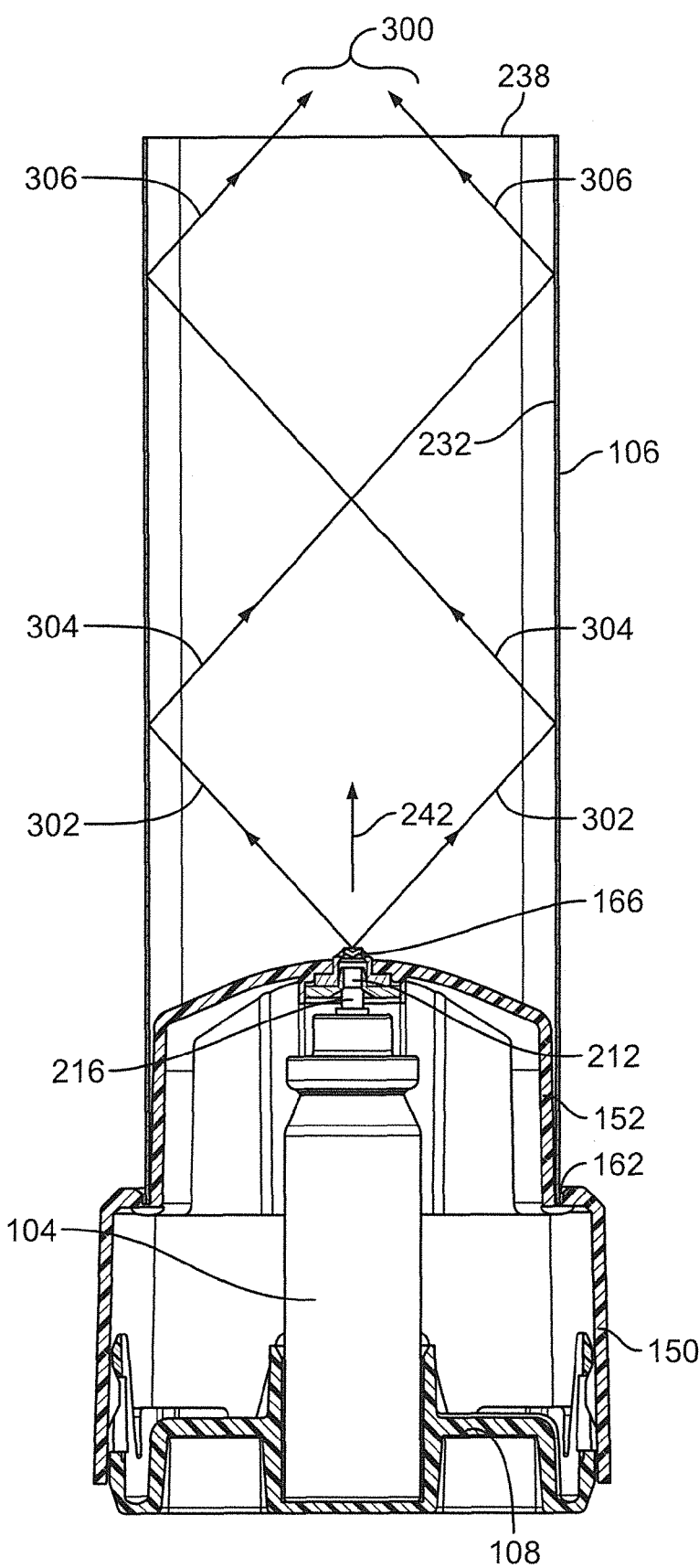
FIG. 20 is a partial cross-sectional side view of the dispenser of FIG. 1 depicting a plurality of spray paths.
Figure 21:
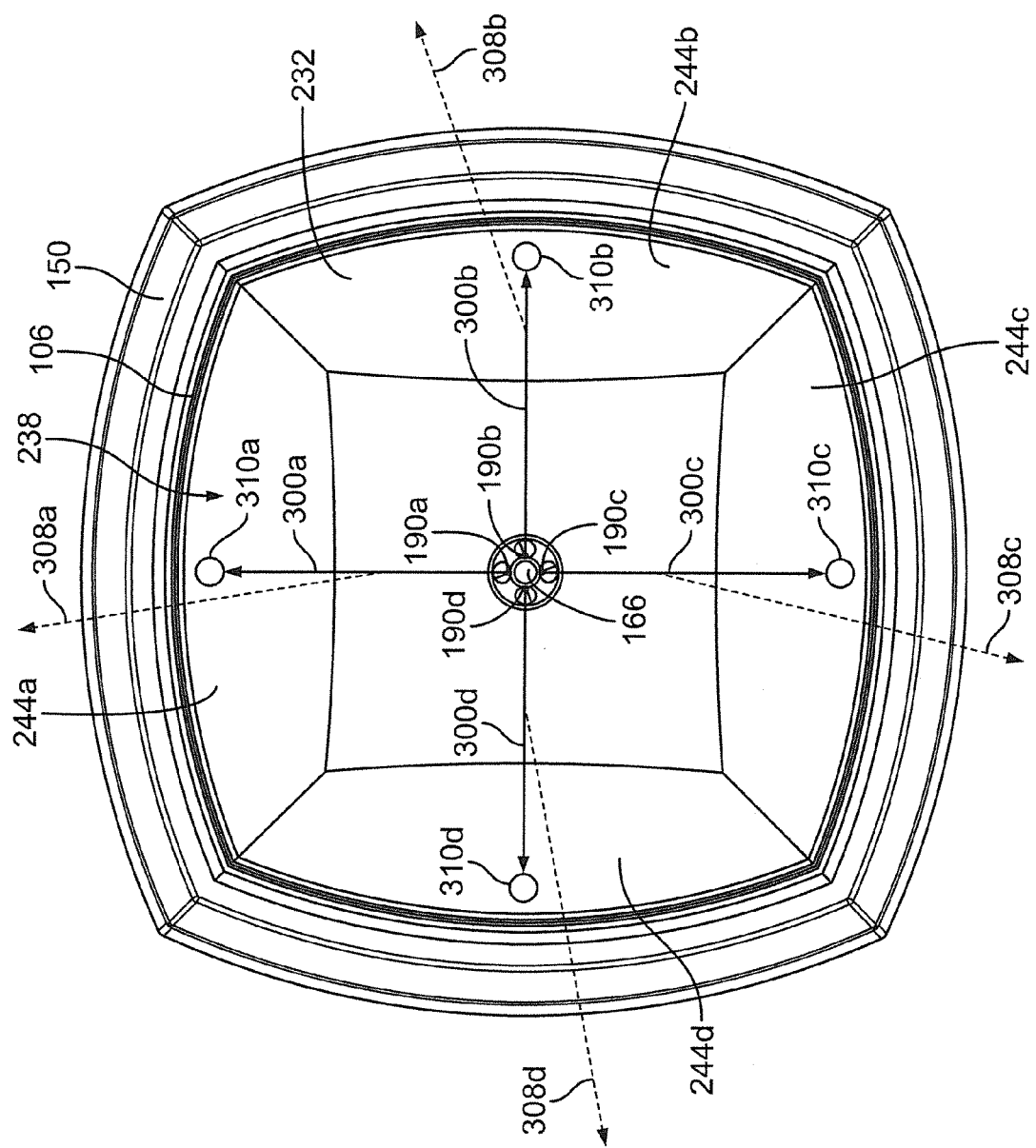
FIG. 21 is a top plan view of the dispenser of FIG. 1 depicting a wetted area on an internal surface of the sleeve.
Figure 22:
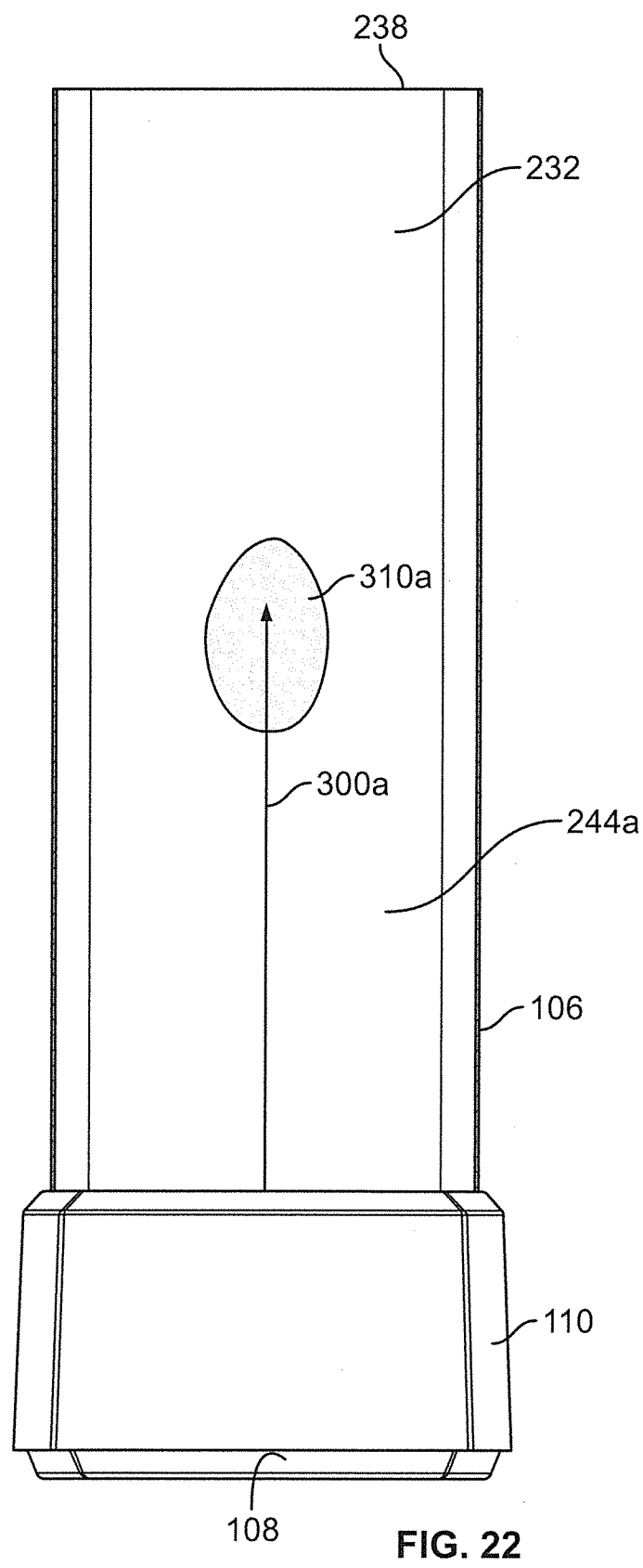
FIG. 22 is a partial cross-sectional side view of the dispenser of FIG. 1 depicting a wetted area on an internal surface of the sleeve.

Now turning to FIG. 16, the dispenser 100 is designed to hold and support a container 104 therein and release a flowable medium (not shown) during actuation. In one embodiment, the container 104 is an aerosol container. Aerosol containers are generally well known to those having skill in the art. In one embodiment, the aerosol container 104 comprises a body 200 with a top end 202 and a bottom end 204. A mounting cup 206 is disposed above a neck 208 of the aerosol container 104. The body 200 is generally cylindrical and is defined by a cylindrical wall 210. A valve assembly (not shown) disposed within an upper portion of the aerosol container 104 includes a valve stem 212 that extends through a pedestal 213 of the container 104.

One suitable valve assembly for use in the container 104 is a 185 mcl valve provided by Aptar under the model number MV002006. Another suitable valve assembly for use in the container 104 is a 300 mcl valve provided by Summit. The valve used in the container 104 preferably emits at least about 100 mcl per spray, and the container 104 preferably includes enough composition for about 65 to about 105 sprays per container.

Still referring to FIG. 16, the valve stem 212 is a cylindrical tube having a passage 214 disposed longitudinally therethrough. A distal end 216 of the valve stem 212 extends upwardly and away from the pedestal 213, and the mounting cup 206 and a proximal end (not shown) is disposed within the valve assembly.

A stem socket 218 (see FIG. 3) is optionally used in conjunction with the actuator nozzle 166 to provide an interface between the valve stem 212 of the container 104 and the chamber 192 of the actuator nozzle 166. The stem socket 218 includes a disc-shaped body with a conical sidewall protruding upwardly therefrom. The conical sidewall is disposed centrally on the body and defines a fluid passageway therein.

In one embodiment, the stem socket 218 is provided in conjunction with the actuator nozzle 166. One or more of the stem socket 218 and/or actuator nozzle 166 may be provided integral with the base 102. In use, the stem socket 218 is seated within the chamber 192 of the actuator nozzle 166. In another instance, the stem socket 218 and/or actuator nozzle 166 may be provided separately, such as, for example, in conjunction with the container 104. In a further embodiment, the stem socket 218 may be omitted. In a different embodiment, another mechanism may be used to provide an interface between the valve stem 212 of the container 104 and the actuator nozzle 166.

Axial compression, i.e., downward movement, of the valve stem 212 opens the valve assembly, which allows a pressure difference between an interior of the aerosol container 104 and the atmosphere to force the contents of the aerosol container 104 out through the distal end 216 of the valve stem 212. It is also contemplated that the aerosol container 104 could utilize a tilt activated valve stem with minimal or no modifications to the structure disclosed hereinafter. In either scenario, a metered-type valve assembly or a continuous valve assembly may be used. Further, in other embodiments, a container 104 having a conventional pump-type or trigger-type sprayer or a pre-compression pump-type or trigger-type sprayer is used in lieu of an aerosol container 104 to hold and dispense the flowable medium. Indeed, it is contemplated that any type of non-aerosol container may be used in conjunction with the dispensers disclosed herein. For example, other containers may include a differing pump-type sprayer, a compressed gas, LPG, or any other compressible or compressed fluid, as would be known to one of skill in the art. The present disclosure with respect to aerosol containers should therefore be considered inclusive of these other types of non-aerosol containers.

The container 104 includes a composition therein that is generally provided as a flowable medium, and more particularly as an aerosol composition. In one embodiment, the flowable medium is a pest control agent. In another embodiment, the flowable medium is an air fragrance agent. In a further embodiment, the flowable medium is a malodor agent.

The aerosol composition may be characterized by certain properties that enhance the composition performance. More specifically, the aerosol composition should possess one or more of the characteristics described herein to ensure that the dispenser 100 is able to provide one or more visual indicators, described in more detail below. With respect to the present embodiment, the aerosol composition provided is a stable single-phase non-aqueous liquid composition which disperses at least one active ingredient contained therein into the air and/or onto the sleeve 106.

The aerosol composition includes at least one hydrocarbon propellant, at least one active ingredient, and at least one solvent. The composition may include one or more optional components that are compatible therewith.

In order to drive the flowable medium out of the dispenser 100, a propellant may be included in the composition. The propellant may be any conventional propellant known in the art that is compatible with the solvent, active, and other ingredients of the composition.

The propellant is generally present in an amount of about 20 wt. % to about 99 wt. %. More specifically, the propellant component is included in an amount of about 30 wt. % to about 95 wt. %, preferably about 70 wt. % to about 90 wt. %, and most preferably about 50 wt. % to about 80 wt. %. In one instance, the propellant is present in an amount of about 80 wt. %.

Hydrocarbons suitable for inclusion in the composition include lower ($C_1$-$C_4$) aliphatic hydrocarbons such as propane, butane, isopropane, isobutane, and mixtures thereof. One particularly suitable propellant is B-52 propellant, which is a mixture of propane/isobutane/n-butane in a weight ratio of about 30/30/40.

Other suitable propellants include, but are not limited to, hydrocarbons, halogenated hydrocarbons, ethers, carbon dioxide, compressed air, compressed nitrogen, and the like. In one refinement, the propellant is a B-60 propellant, which is a mixture of propane, butane, and isobutane. In another refinement, the propellant is an A-60 propellant, which is a mixture of propane and isobutane.

The composition further includes at least one active ingredient. The at least one active ingredient of the aerosol composition is present in an amount of about 0.001 wt. % to about 10 wt. %, preferably about 0.5 wt. % to about 7 wt. %, and most preferably about 1 wt. % to about 5 wt. %. One or more active ingredients can be used in combination in the aerosol composition. Active ingredients suitable for inclusion are materials known and/or suitable for dispensing through spraying.

In one embodiment, the active ingredient is preferably an insecticide, an insect repellant, or an insect attractant. Alternatively, the active ingredient may be a disinfectant, sanitizer, air purifier, aromatherapy scent, antiseptic, air-freshener, and/or deodorizer. Other examples of active ingredients include fragrances (e.g., natural and synthetic oils), odor eliminators, such as triethyleneglycol and/or propylene glycol, antimicrobials, anti-bacterials, corrosion inhibitors, pH adjustors, preservatives, organic acids, and the like, or any other active ingredient(s) that are usefully dispersed into the air.

In one embodiment, the active material is an insecticide and/or insect repellent, an organic phosphorous insecticide, a lipidamide insecticide, a natural repellent such as citronella oil, a natural pyrethrin, a pyrethrum extract, or a synthetic pyrethroids. Suitable synthetic pyrethroids are acrinathrin, allethrin as D-allethrin, Pynamin®, benfluthrin, bifenthrin, bioallethrin as Pynamin Forte®, S-bioallethrin, esbiothrin, esbiol, bisoresmethrin, cycloprothrin, cyfluthrin, beta-cyfluthrin, cyhalothrin, lambda-cyhalothrin, cypermethrin, alpha-cypermethrin, beta-cypermethrin, cyphenothrin, deltamethrin, empenthrin, esfenvalerate, fenpropathrin, fenvalerate, flucythrinate, taufluvalinate, kadethrin, permethrin, phenothrin, prallethrin as Etoc®, resmethrin, tefluthrin, tetramethrin, tralomethrin, metofluthrin, transfluthrin, and/or combinations thereof. Other volatile insecticides, such as those described in U.S. Pat. No. 4,439,415, can also be employed.

In particularly preferred versions, the volatile insecticide is selected from the group consisting of transfluthrin, metofluthrin, vapothrin, permethrin, prallethrin, tefluthrin, and esbiothrin. In a particular embodiment, metofluthrin is the most preferred insecticide.

A wide variety of volatile fragrances may be used that may optionally also have insect control attributes. Alternatively, some fragrances may be selected that provide a deodorizing function (e.g. certain terpenes). For example, various natural and artificial perfumes may be used. Non-limiting examples of these perfumes include animal-based and plant-based natural perfumes, and artificial perfumes such as alcohols, phenols, aldehydes, ketones, terpenes, and esters.

The fragrance according to this disclosure may comprise one or more fragrant materials or materials that provide chemically active vapors. In one embodiment, the fragrance can comprise and/or include volatile, fragrant compounds including, but not limited to natural botanic extracts, essences, fragrance oils, and so forth. As is known in the art, many essential oils and other natural plant derivatives contain large percentages of highly volatile scents. In this regard, numerous essential oils, essences, and scented concentrates are commonly available from companies in the fragrance and food businesses.

Exemplary oils and extracts include, but are not limited to, those derived from the following plants: almond, amyris, anise, armoise, bergamot, cabreuva, calendula, canaga, cedar, chamomile, coconut, eucalyptus, fennel, jasmine, juniper, lavender, lemon, lemongrass, orange, palm, peppermint, quassia, rosemary, thyme, and so forth.

In one embodiment, the composition may be carried in a solvent such as an organic solvent, and more particularly a hydrocarbon solvent. The solvent is present in an amount of about 1 wt. % to about 30 wt. %, preferably about 5 wt. % to about 30 wt. %, and most preferably about 15 wt. % to about 25 wt. %. In one particular instance, the solvent is present in an amount of about 19 wt. %.

Types of solvents that are useful include, but are not limited to, Isopar C, Isopar E, Isopar L, heptane, methanol, acetone, ethanol, isopropyl alcohol, dodecene and tetraydrofuran. The ISOPAR® branded solvents are high purity isoparaffin fluids with narrow boiling ranges manufactured by ExxonMobil Chemical, wherein differing grades are denoted as E, G, L, M, and V.

One particularly suitable composition for use in the dispenser 100 comprises an aerosol composition having a propellant in an amount of about 80 wt. %, a solvent in an amount of about 19 wt. %, an active in an amount of about 1 wt. %, and a fragrance in an amount of less than 1 wt. %. In another embodiment, the aerosol composition comprises propellant in an amount of about 90 wt. %, an active in an amount of about 1 wt. %, and a solvent in an amount of about 9 wt. %. In a further embodiment, the aerosol composition comprises propellant in an amount of about 95 wt. %, an active in an amount of about 1 wt. %, and a solvent in an amount of about 4 wt. %. In another embodiment, the aerosol composition comprises propellant in an amount of about 85 wt. %, an active in an amount of about 2 wt. %, and a solvent in an amount of about 13 wt. %.

One particularly desirable formulation for mosquito control includes 1 wt. % metofluthrin dissolved in 18.8 wt. % Isopar L hydrocarbon and further includes eucalyptus oil in an amount of 0.15 wt. % and B-52 propellant in an amount of 80 wt. %.

Numerous characteristics of the aerosol are important to achieve the specific dispensing capabilities of the dispenser 100 described herein. For example, the particle size of the aerosol composition upon dispersion as a spray is important. In one embodiment, the average particle size of the droplets of the spray is greater than or equal to about 5 microns. In another embodiment, the average particle size of the droplets of the spray is greater than or equal to about 10 microns. In a further embodiment, the average particle size of the droplets of the spray is greater than equal to about 15 microns. In another embodiment, the average particle size of the droplets is between about 5 microns to about 200 microns. More particularly, it has been found that a Dv(50) particle size distribution of 5 microns to 100 microns may be preferable, and a Dv(50) particle size distribution of 11 microns to 74 microns even more preferable. Further, it has been found that a Dv(90) particle size distribution of 5 microns to 200 microns may be preferable, and a Dv(90) particle size distribution of 25 microns to 126 microns even more preferable. In another embodiment, the droplets may have a Dv(90) particle size distribution that is less than or equal to 30 microns.

Another important property of the aerosol composition is the spray rate during dispensing. In particular, enough aerosol composition must be discharged to provide the visual and audible indicators as described below, but too large of a spray rate may result in the aerosol composition being discharged onto and/or through the sleeve 106 in an undesirable way. It is believed that an aerosol composition having a spray rate of over about 60 grams per second at a point of impact with the sleeve 106 may result in undesirable spray characteristics, e.g., the composition may be sprayed through a wall of the sleeve as opposed to being deposited onto and subsequently absorbed by the sleeve 106.

It is further believed that an aerosol composition having a spray rate under about 5 grams per second at a point of discharge (i.e., upon leaving an outlet port 190) would be insufficient to provide one or more of the indicators described herein, e.g., a plume within or above the sleeve 106 and/or a wetted area on the sleeve. Therefore, it is desirable that the spray rate of the aerosol composition is at least about 10 grams per second at the point of discharge, but less than about 60 grams per second at a point of impact with the sleeve 106, which has the below noted physical properties. In some specific embodiments, the aerosol composition is discharged from the container 104 at a spray rate of at least about 10, about 20, or about 30 grams per second, and less than about 70, about 60, or about 50 grams per second.

Another important parameter is the density of the composition. In particular, the density impacts, among other things, the spray rate of the composition, which ultimately affects how much of the spray is retained within the sleeve 106 and how much of the spray that is formed into a plume. It is envisioned that the composition density (measured at 15° C.) is between about 0.2 g/cm$^3$ to about 1 g/cm$^3$. In one embodiment, the composition density (measured at 15° C.) is between about 0.4 g/cm$^3$ to about 0.8 g/cm$^3$. In a different embodiment, the composition density (measured at 15° C.) is between about 0.5 g/cm$^3$ to about 0.7 g/cm$^3$. In a different embodiment, the composition density (measured at 15° C.) is about 0.6 g/cm$^3$.

Now turning to FIGS. 17-19, the dispenser 100 further includes the sleeve 106, which is supported on the base 102 via the recess 162 disposed between the shroud 150 and the dome 152 (see FIG. 12). The sleeve 106 is defined by a permeable and/or absorbent substrate 230 having an interior surface 232 and an exterior surface 234. In one embodiment, the substrate 230 is folded to form an elongate conduit 236 (see FIG. 17) bounded by an upper opening 238 and a lower opening 240 with a channel 242 extending therebetween. The substrate 230 has an upper end and a lower end that correspond to the upper opening 238 and the lower opening 240, respectively. The channel 242 and the upper opening 238 are unobstructed to allow the aerosol composition to exit directly therethrough (e.g., without being impeded by a lid). Additionally, the lower opening 240 is unobstructed to allow the sleeve 106 to mate with the dome 152. In one particular embodiment, the sleeve/conduit/substrate is positioned on or adjacent to the base (e.g., the dome 152) in a manner that circumscribes or surrounds same. It is also anticipated that other embodiments may include a sleeve 106 with structures within the channel 242 and/or other portions to provide rigidity to the sleeve 106 or otherwise effect spraying and distribution of the flowable medium. Further, the sleeve 106 may be one or more of opaque, translucent, or transparent.

In one embodiment, the sleeve 106 may be provided as a tubular member, which may comprise any geometric shape. In another embodiment, the sleeve 106 may be imparted with a circular or oval shape. In a further embodiment, the sleeve 106 may be provided with a square or rectangular shape. In a different embodiment, the sleeve 106 is imparted with a shape having a non-uniform cross-section that includes at least one major axis extending between the two most distant points of the shape and/or a minor axis that extends between the two closest points of the shape. In fact, in other embodiments the sleeve 106 may be provided with other shapes that include the channel 242 providing an outlet pathway from the base 102 into the external environment outside of the sleeve 106.

In one embodiment, the conduit 236 is provided with a substantially similar cross-sectional geometry to that of the base 102. In particular, the substrate 230 has a uniform cross-sectional footprint along the length thereof and includes four distinct arcuate sides 244a-244d as viewed from a top plan view (see FIG. 18). The sides 244a-244d are joined at corners 246a-246d to form the conduit 236. One or more of the sides 244a-244d may be integral with respect to each other, or the conduit 236 may be formed by joining one of more of the sides 244a-244d to each other in manners known in the art (e.g., by an adhesive, an interlocking mechanism, stitching, and other joining mechanisms). The corners 246a-246d are the points of intersection between the sides 244a-244d and may be formed naturally due to the geometric shape of the sleeve 106, or may be defined by a seam or other point in which the angle of the side 244a changes.

Each side 244a-244d of the substrate 230 is defined by a thickness dimension of between about 0.1 mm to about 3 mm. In another embodiment, the substrate 230 is defined by a thickness dimension of between about 0.1 mm to about 0.17 mm. In a further embodiment, the substrate 230 is defined by a thickness of between about 0.17 mm to about 0.30 mm. In an additional embodiment, the substrate 230 is defined by a thickness dimension of not more than about 2 mm. In yet a different embodiment, the substrate 230 is defined by a thickness dimension of not less than about 0.1 mm. In still a different embodiment, the substrate 230 is defined by a thickness dimension of not less than about 0.08 mm and not more than about 2 mm. In an additional embodiment, the substrate 230 is defined by a thickness dimension of between about 0.07 mm to about 0.8 mm. In a different embodiment, the substrate 230 is defined by a thickness dimension of between about 0.13 mm to about 0.38 mm. In a further embodiment, the thickness may be impacted due to the inclusion of a reinforcing element in one or more of the sides 244a-244d. For example, in one embodiment, nylon may be added to the sides 244a-244d. In one particular embodiment, a scrim is added to a non-woven substrate to increase its stiffness. In a different embodiment, other, and/or additional material may be added or otherwise applied to the sides 244a-244d.

As depicted in FIG. 19, each side 244a-244d of the substrate 230 is defined by a height dimension $H_s$ measured between a top and bottom edge of each of the sides 244a-244d. In one embodiment, the height dimension $H_s$ is between about 50 mm to about 300 mm. In another embodiment, the height dimension $H_s$ is between about 100 mm to about 200 mm. In a further embodiment, the height dimension $H_s$ is between about 150 mm to about 200 mm. In an additional embodiment, the height dimension $H_s$ is not more than about 300 mm. In yet a different embodiment, the height dimension $H_s$ is not less than about 25 mm. In still a different embodiment, the height dimension $H_s$ is not less than about 250 mm and not more than about 400 mm. In another embodiment, the height of the sides 244a-244d may differ with respect to each other.

The substrate 230 of the sleeve 106 may be generally characterized as having a horizontal component and a vertical wall extending upwardly from the horizontal component. Each side 244a-244d of the substrate 230 is also defined by a horizontal length dimension $L_s$, as measured between the corners 246a-246d of the sleeve 106. For example, as shown in FIG. 19, the horizontal length dimension $L_s$ of the side 244a is defined as the length of the side 244a between corner 246a and corner 246d. In one embodiment, the horizontal length dimension $L_s$ is between about 25 mm to about 200 mm. In another embodiment, the horizontal length dimension $L_s$ is between about 40 mm to about 80 mm. In a further embodiment, a horizontal length dimension $L_t$ may be characterized as the entire linear horizontal length component of the sleeve 106, wherein $L_t$ may be between about 50 mm to about 1000 mm, and more preferably between 50 mm to about 200 mm. In another embodiment, the horizontal length dimension may be varied for one or more of the sides 244a-244d to create different geometric shapes.

In many instances, the height of each side 244a-244d of the sleeve 106 is related to numerous other properties of the dispenser 100. For example, the sleeve 106 is sized to accommodate specific spray angles, spray rates, compositions, and numerous other parameters described herein. In one particular example, it is contemplated that the height dimension $H_s$ of the sides 244a-244d of the sleeve 106 are related to the horizontal length dimension $L_s$ or $L_t$. In one embodiment, the ratio of the height $H_s$ to the horizontal length dimension $L_s$ of one side 244 of the dispenser 100 is between about 3 to about 1. In another embodiment, the height $H_s$ to horizontal length dimension $L_t$ ratio is between about 1 to about 1. In a further embodiment, the height $H_s$ to horizontal length dimension $L_s$ ratio is greater than about 2 to about 1.

The volumetric capacity of the conduit 236 or channel 242 is important to help facilitate the formation of one or more indicators, discussed in more detail below. In particular, the conduit 236 should possess a sufficiently large volumetric capacity to accommodate the spray from the container 104 to form a plume and/or a wetted area thereon. If the volumetric capacity is too large, it is believed that the plume will not form properly and that not enough spray material will be deposited on the sleeve 104 in the manner described herein to provide effective passive diffusion. In contrast, if the volumetric capacity is too small, a significant amount of spray from the container 104 will exit the sleeve 106 and not be deposited therein and/or thereon for passive diffusion. Additionally, a smaller volumetric capacity would deplete the aerosol composition material available to form the plume, which may result in deficiencies with respect to plume formation.

Therefore, the conduit 236 or channel 242 may be provided with a bounded volumetric capacity of between about 100 $cm^3$ to about 4000 $cm^3$, when the conduit 236 is free standing and not disposed on the base 102. In another embodiment, conduit 236 is defined by a bounded volumetric capacity of between 300 $cm^3$ to about 800 $cm^3$. In a further embodiment, conduit 236 is defined by a bounded volumetric capacity between 600 $cm^3$ to about 650 $cm^3$. In an additional embodiment, the conduit 236 is defined by a bounded volumetric capacity of not less than about 100 $cm^3$. In yet a different embodiment, the conduit 236 is defined by a bounded volumetric capacity of not less than about 400 $cm^3$. In still a different embodiment, the conduit 236 is defined by a bounded volumetric capacity of not less than 600 $cm^3$ and not more than about 4000 $cm^3$. In one particular embodiment, the conduit 236 is defined by a bounded volumetric capacity of about 640 $cm^3$. In a different embodiment, the channel 242 of the conduit has an interior volume of between 300 $cm^3$ to 400 $cm^3$.

The channel 242 of the substrate 230 or conduit 236 may be defined by various additional volumetric and/or design parameters of the sleeve 106. In one embodiment, the channel 242 is uninterrupted. In this instance, the interior surface 232 defining the channel 242 is contiguous along its length and/or width thereof and does not have surface interruptions beyond those exhibited by the individual fibers or constituent parts thereof. For example, the interior surface 232 of the channel 242 of FIG. 20 is uninterrupted and appears to be substantially flat along the length thereof. In another instance, the uninterrupted interior surface 232 of the channel 242 extends entirely between the upper opening 238 and the lower opening 240 of the sleeve 106. In a different embodiment, it is further contemplated that the uninterrupted channel 242 may be completely bounded such that the sleeve 106 is opaque. In a further embodiment, both the interior surface 232 and the exterior surface 234 are uninterrupted.

In a different embodiment, the channel 242 of the substrate 230 is at least partially interrupted. In this embodiment, the channel 242 may be interrupted via one or more mechanisms. For example, in one embodiment, at least one hole or other opening may be present in the sleeve 106 (apart from the upper opening 238 and lower opening 240). In one specific embodiment, the surface interruption may comprise a substrate 230 having an average pore size of greater than about 250 microns. In a further embodiment, one or more portions of the substrate 230 may be provided as a mesh and/or formed in a cross-hatched pattern to include a plurality of surface interruptions. In an additional embodiment, one or more portions of the partially interrupted substrate 230 comprises a structure that divides the interior of the sleeve 106 into two or more separate volumes.

In some instances, the surface interruptions may impact the formation of the plume and/or the amount of flowable material that extends through the sleeve 106 versus the amount of flowable material that stays on, or absorbs into, the sleeve 106. In a different embodiment, one or more portions of the substrate 230 may be provided with a notch, a cutout, and/or other surface disruption in addition to the upper and lower openings 238, 240.

In a further embodiment, the channel 242 may be defined by the contour formed by the natural boundary thereof. For example, the channel 242 may be imparted with a specific geometric shape due to structural and/or rigidity components thereof. In one embodiment, the channel 242 at least partially acts to limit free air or volatile movement.

Additionally, the conduit 236 or channel 242 may have a bounded volumetric capacity of between about 200 $cm^3$ to about 700 $cm^3$, when the conduit 236 is disposed on the base 102. In another embodiment, conduit 236 is defined by a bounded volumetric capacity of between 300 cm$^3$ to about 600 cm$^3$. In a further embodiment, conduit 236 is defined by a bounded volumetric capacity between 400 cm$^3$ to about 550 cm$^3$. In an additional embodiment, the conduit 236 is defined by a bounded volumetric capacity of not less than about 500 cm$^3$. In yet a different embodiment, the conduit 236 is defined by a bounded volumetric capacity of not less than about 400 cm$^3$. In still a different embodiment, the conduit 236 is defined by a bounded volumetric capacity of not less than 300 cm$^3$ and not more than about 600 cm$^3$. In one particular embodiment, the conduit 236 is defined by a bounded volumetric capacity of about 515 cm$^3$.

The conduit 236 may also include a minimum cross-sectional area within the bounded volume of at least about 15 cm$^2$ and a maximum cross-sectional area within the bounded volume of less than about 400 cm$^2$. In another embodiment, the conduit 236 includes a minimum cross-sectional area within the bounded volume of at least about 40 cm$^2$ and a maximum cross-sectional area within the bounded volume of less than about 100 cm$^2$. In a further embodiment, the conduit 236 also includes a minimum cross-sectional area within the bounded volume of at least about 38 cm$^2$. It is contemplated that the maximum cross-sectional area may be provided at an upper end or outlet end of the conduit or substrate, or, alternatively the minimum cross-sectional area could be provided at the upper end. Indeed, it is also contemplated that a globular shade or substrate may be provided with a maximum cross-sectional area about a medial portion thereof.

The conduit 236 may include a major axis and, in some embodiments, a minor axis, which may be perpendicular thereto. In one embodiment, the minor axis is a width of the sleeve 106. In a further embodiment, the minor axis comprises a line extending between the interior surfaces of two opposing walls. In a further embodiment, the minor axis may be a straight line measurement between two distal surfaces. In another embodiment, the minor axis may be a diameter.

Selection of the material comprising the sleeve 106 is important for numerous reasons. In particular, the sleeve 106 material impacts, among other things, the look of the sleeve 106, the wicking properties of the sleeve 106, the absorbency properties of the sleeve 106, the ability of the sleeve 106 to be retained in an upright position on the base 102, plume formation, and numerous other properties relating to the display of one or more of the visual indicators.

Accordingly, the sleeve 106 may comprise a permeable material, such as a PET non-woven material, fabric, textile, non-woven fibers, or other permeable material. In one specific example, the sleeve material comprises a nylon fabric provided by Cerex® Advanced Fabrics (Cantonment, Fla.). In one embodiment, the fabric may be non-woven, which is made by spinning and autogenously bonding continuous filaments of nylon into a flat, smooth, and strong fabric. One particular suitable fabric is a nylon substrate sold under the trade name Cerex 23200. In a different embodiment, the sleeve 106 may be woven and/or continuous. For example, the sleeve 106 may be a smooth sheet having micro-sized pores (e.g., Gore Tex® or a material similar to Gore Tex®). In a further embodiment, the sleeve 106 may comprise a laminate or other surface having a nylon interior surface.

In one embodiment, the sleeve 106 is provided as a non-woven material that is between about 5 mils to about 12 mils, and more particularly between about 7 mils to about 9 mils as determined using ASTM-D1777. In one embodiment, the air permeability of the material of the sleeve 106 is between about 15 CFM/ft$^2$ and about 325 CFM/ft$^2$, and more particularly about 170 CFM/ft$^2$, as determined by ASTM D737. The material of the sleeve 106 may also have a bursting strength of between about 2 bar to about 70 bar, and more particularly about 5 bar.

One or more properties of the sleeve 106 material impact the dispensing capabilities of the dispenser 100. A preferred sleeve 106 is rigid and self-supporting such that it can remain in an upright position without assistance (e.g., standing on end without structural collapse). At the same time, the sleeve 106 should be flexible enough to be accommodated by the recess 162 of the base 102. In some instances, depending on the shape of the sleeve 106, the sleeve 106 may need to be flexible enough to bend or otherwise deform when the sleeve 106 is being positioned on the base 102. The sleeve 106 should also have moderate wetting characteristics and moderate porosity that leads to an efficacious release profile, as compared to other materials. It may also be desirable for the sleeve 106 to have low affinity and absorbency properties with respect to the active, as compared to other materials.

The sleeve material may be characterized by one or more properties such as surface energy. The surface energy describes the excess energy at surfaces compared to material in the bulk. Generally, it is energetically preferable for the composition to be in the bulk material rather than on the surface of the sleeve 106. The surface energy gives a measure of the energy required to form surface area and controls the amount of surface that will be formed, and thus, the amount of surface the liquid will have available for evaporation to occur. To that end, the material of the sleeve 106 preferably has a surface energy of less than about 25 mN/m. In another embodiment, the material has a surface energy of less than about 20 mN/m. In a further embodiment, the material has a surface energy of less than about 18 mN/m. In a different embodiment, the material has a surface energy of between about 1 mN/m to about 30 mN/m. In another embodiment, the material has a surface energy of between about 5 mN/m to about 25 mN/m. In a further embodiment, the material has a surface energy of between about 10 mN/m to about 20 mN/m. In one specific embodiment, the material has a surface energy of about 19 mN/m.

The visual appearance of the material used for the sleeve 106 is an additional important property to accomplish the functionality of the sleeve 106 described herein. In particular, without being bound by theory, it is believed that a consumer's experience is heightened during the use of a dispenser when the consumer is able to perceive that a dispenser is working and that the dispenser possesses the characteristics to provide the appropriate functionality. For example, consumers recognize that a plastic, a solid surface, or an otherwise impermeable-appearing surface is generally not capable of providing passive emanation due to a lack of absorbency. In particular, consumers understand that the sprayed composition may bead up and may not be able to be absorbed into the surface. Further, some consumers perceive that smooth looking and/or uninterrupted surfaces may not have adequate absorbent properties, regardless of the true nature of the material, and will not have confidence that the material will absorb the composition or passively diffuse it. In contrast, consumers understand that fabric or textile materials provide a specific visual appearance and that the materials are capable of absorbing the aerosol composition, and thus, are capable of providing passive emanation. Therefore, it is desirable to provide a sleeve 106 having specific properties that aid the consumer in recognizing the absorbent nature thereof. The sleeve 106 should be provided with one or more of the following parameters to ensure that the sleeve 106 provides a sufficient visual indicator of absorbency.

The sleeve 106 material is preferably defined by a plurality of fibers having a diameter greater than about 50 microns. In one embodiment, the diameter of the fibers is between about 45 microns to about 120 microns. In another embodiment, the diameter of the fibers is between about 50 microns to about 100 microns. In a different embodiment, the diameter of the fibers is between about 60 microns to about 90 microns. In a further embodiment, the diameter of the fibers is between about 70 microns to about 80 microns. In one specific embodiment, the diameter of the fibers is about 90 microns. In another embodiment, the diameter of the fibers is about 100 microns. In a further embodiment, the diameter of the fibers is about 120 microns. In yet another embodiment, the diameter of the fibers is about 130 microns.

Coloration of the fibers in the material of the sleeve 106 is also important to provide a visual indicator to the user of the fabric-like nature thereof. In particular, the coloration of the fibers of the sleeve 106 provides contrast that assists the user in being able to visually perceive individual fibers. For example, in one instance, the fibers of the sleeve 106 are the same color, such as white. In another instance, one or more fibers may be imparted with different coloration to provide a further visual contrast therebetween.

Pore size is also important in imparting a specific visual indicator to the user. In particular, the larger the pore size of the material, the more visible the pores are, which results in a consumer understanding that the sleeve material comprises a fabric-like or otherwise-absorbent material. The pore size between the fibers should be a sufficient size to be visible and give the impression of a porous material. For the texture of the sleeve 106 material to be visible, there must be sufficient contrast between the fibers and the pores. In particular, in one embodiment, the median pore diameter by volume may be at least about 50 microns or larger, comprising either individual pores or clusters of pores in close proximity. In another embodiment, the median pore diameter by volume of the sleeve 106 is between about 50 microns to about 1000 microns. In another embodiment, the median pore diameter by volume of the sleeve 106 is between about 50 microns to about 80 microns. In one embodiment, the median pore diameter by volume is between about 50 microns to about 250 microns. In another embodiment, the median pore diameter by volume is between about 50 microns to about 100 microns. In one specific embodiment, the median pore diameter by volume is at least 50 microns. In another embodiment, the median pore diameter by volume is about 60 microns. In a further embodiment, the median pore diameter by volume is 75 microns. In yet another embodiment, the median pore diameter by volume is about 80 microns. In a different embodiment, the median pore diameter by volume is less than 80 microns. In a further embodiment, the median pore diameter may not be consistent over the entirely of the sleeve 106. For example, one portion of the sleeve 106 may be characterized by a median pore diameter of a first value (e.g., about 50 microns), whereas another portion of the sleeve 106 may be characterized by a second, different value (e.g., about 70 microns).

The substrate 230 of the sleeve 106 may be further characterized by a void volume (i.e., porosity) of at least 1.55 mL/g. In another embodiment, the substrate 230 of the sleeve 106 may be further characterized by a porosity of between about 1 mL/g to about 10 mL/g. In a different embodiment, the substrate 230 of the sleeve 106 may be further characterized by a porosity of between about 1.55 mL/g to about 7.13 mL/g. In a further embodiment, the substrate 230 of the sleeve 106 may be further characterized by a porosity of not more than about 8 mL/g.

The thickness of the sleeve 106 material is also important in providing the advantages realized through the use of the sleeve 106. For example, the sleeve 106 should be able to accommodate the spray velocity of the flowable medium discharged from the actuator nozzle 166 and have a thickness sufficient to prevent the majority of the spray from exiting directly through the sleeve 106. The thickness of the sleeve 106 is also important to the wicking and absorbency properties thereof, which impacts the formation of one or more of the visual indicators (e.g., a plume and/or a wetted area).

An additional consideration for the material of the sleeve 106 is the tactile feedback that the user can obtain from interacting with (e.g., touching) the sleeve 106. The tactile feedback is dependent on numerous material characteristics including surface roughness, material ‘stiffness’, and thermal behavior. A very smooth surface, such as a plastic film, would be expected by the user to be impermeable to a liquid based on the users experience with plastic sheets, whereas a more textured surface would be expected to allow liquids to absorb based on the users experience with fabrics.

The material of the sleeve 106 may also possess wicking properties characterized by the average wicking speed, which impact the time to form the wetted area on the sleeve 106 after actuation. The average wicking speed can be determined using gravimetric analysis. In one embodiment, the average wicking speed is between about 0.01 mm/s to 1.5 mm/s. In another embodiment, the average wicking speed is between about 0.05 mm/s to about 1 mm/s. In a different embodiment, the average wicking speed is between about 0.07 mm/s to about 0.09 mm/s. In one embodiment, the average wicking speed is between about 0.05 mm/s to about 0.1 mm/s. In one specific embodiment, the average wicking speed is about 0.09 mm/s. In another embodiment, the wicking speed is about 1 mm/s. In a further embodiment, the average wicking speed is about 0.095 mm/s. In yet another embodiment, the average wicking speed is at least about 0.05 mm/s. In another embodiment, the average wicking speed is at least about 0.05 mm/s.

The bulk density of the sleeve 106 also impacts the rigidity and tactile properties of the substrate 230 of the sleeve 106. In one embodiment, the bulk density is between about 1 $g/cm^3$ to about 2 $g/cm^3$. In another embodiment, the bulk density is less than about 1.275 $g/cm^3$. In a further embodiment, the bulk density is between about 1.142 $g/cm^3$ to about 1.273 $g/cm^3$. In a different embodiment, the bulk density is less than about 2 $g/cm^3$. In a still further embodiment, the bulk density is between about 1 $g/cm^3$ to about 3 $g/cm^3$.

The strip tensile strength of the sleeve 106 is related to the stress that the substrate 230 can handle prior to failing. In one embodiment, the strip tensile strength is at least about 3 N/mm, and more specifically about 3.03 N/mm. In another embodiment, the strip tensile strength is at least about 4 N/mm. In a further embodiment, the strip tensile strength is between about 2.5 N/mm and about 3.5 N/mm.

The material of the sleeve 106 further includes absorption properties characterized by absorption capacity, as measured through gravimetric analysis. In one embodiment, the absorption capacity is between about 1 ml/g to about 3.5 ml/g. In another embodiment, the absorption capacity is between about 1.5 ml/g to about 3 ml/g. In a different embodiment, the absorption capacity is between about 2 ml/g to about 3 ml/g. In one specific embodiment, the absorption capacity is about 2.5 ml/g. In another embodiment, the absorption capacity is about 2.6 ml/g. In a further embodiment, the absorption capacity is about 2.7 ml/g. In yet another embodiment, the absorption capacity is at least about 2.5 ml/g. The material of the sleeve 106 is also capable of absorbing about 0.015 mg/mm$^2$ of the flowable medium.

One particular sleeve 106 having the following characteristics is useful with respect to the dispenser 100 described herein. The sleeve 106 material has a nominal sheet thickness of 8.4 mils or 0.21 mm and is composed of a multitude of non-woven fibers, interspersed with pores having a median pore diameter (by volume) of about 50 microns. In this embodiment, the material has a porosity of 1.55 ml/g. The gravimetric derived density is 0.4 mg/mm$^3$ and the bulk density is 1.14 g/cm$^3$. Additionally, the sleeve 106 is defined by a strip tensile strength in the cross direction of about 3 N/mm and a strip tensile strength in the machine direction of about 5.6 N/mm.

Referring again to FIGS. 1-3, the sleeve 106 is depicted as being imparted with a pattern 250 formed thereon. The pattern 250 may be constructed of the absorbent material and/or a portion 252 of the substrate 230 surrounding the pattern may be constructed from the same or another material. The pattern 250 may also be formed by apertures through the substrate 230 in the shape of the pattern 250. In this case, the absorbent material may partially or completely span the apertures. In some instances, the pattern is defined by one or more natural appearing objects such as leaves, flowers, plants, trees, and the like. In other embodiments, the pattern may be defined by other shapes.

The component parts having been described, the use of the dispenser 100 and properties relating thereto are hereinafter discussed in greater detail. One or more components of the dispenser 100 may be provided in packaging (not shown). For example, a starter package may include the base 102, one or more containers 104, and the sleeve 106. In one embodiment, the container 104 and/or the sleeve 106 are provided as a refill kit.

In a different embodiment, the sleeve may be pre-loaded with the flowable substance. In this embodiment, it is contemplated that the flowable substance would be supplied in a non-permeable package and that the flowable medium would not start to passively diffuse until the sleeve 106 is removed from the package. In a further embodiment, a sleeve 106 with flowable medium preloaded thereon may be used in combination with a flowable medium disposed within the container 104. For example, it is contemplated that one substance (e.g., the active) may be preloaded onto the sleeve 106 and a second substance (e.g., the solvent) would be supplied in the container 104. In this instance, the solvent would contact the active during actuation to supply a synergistic effect. Alternatively, the flowable medium preloaded onto the sleeve 106 may become active and start passively diffusion only upon interaction with a second flowable medium supplied in the container 104, or otherwise sprayed onto the dispenser 100. Still further, one active may be disposed in the container 104, while a second, different active (and/or flowable medium) is preloaded onto the sleeve 106. For example, a pest control agent or active may be supplied in the container 104, whereas a fragrance may be preloaded onto the sleeve 106.

To use the dispenser 100, each of the component parts must be removed from the packaging, and the container 104 having an aerosol composition must be inserted into the base 102. To insert the container 104 into the base 102, the upper housing 110 must be removed from the lower housing 108 of the base 102 (if the components are joined). To remove the upper housing 110 from the lower housing 108, a user can grasp the grooves 116 of the lower housing 108 with one hand and use the other hand to apply upward force to the upper housing 110 in a direction away from the lower housing 108. Once the lower housing 108 is exposed, the user positions the container 104 into the opening 136 of the pedestal 134 to be retained thereby.

Once the container 104 is properly positioned, the base 102 must be reassembled. To attach the upper housing 110 to the lower housing 108, each are substantially aligned with respect to one another. The upper housing 110 is lowered onto the lower housing 108, which causes the angled end portions 178 of the protrusions 170 to contact the tapered horizontal sections 130 of the flanges 126 of the U-shaped members 124. The U-shaped members 124 flex inwardly to allow the protrusions 170 to slide into and be retained in the openings 128 of the members 124. Once the protrusions 170 are seated within the openings 128, the U-shaped members 124 flex outwardly into their original position to releasably lock the upper housing 110 to the lower housing 108 (see FIG. 11). At the same time, the container 104 is guided upwardly through the upper housing 110 via the ribs 174 until the valve stem 212 of the container 104 is snuggly positioned within the stem socket 218.

If the sleeve 106 is not pre-assembled on the dispenser 100, the sleeve 106 is positioned on the base 102 by aligning the sleeve 106 over the dome 152 and lowering the sleeve 106 downwardly thereon. The dome 152 is received into the lower opening 240 of the sleeve 106. As the sleeve 106 moves downwardly toward the dome 152, the sleeve 106 interacts with the recess 162 disposed between the shroud 150 and the dome 152. Once positioned, the sleeve 106 contacts the sidewalls 158 of the dome 152 over at least a portion thereof. The sleeve 106 may be provided in a similar shape to that of the dome 152 to facilitate a uniform look to the dispenser 100. Additionally, the sleeve 106 may be provided in a different shape, so long as the sleeve 106 is capable of being inserted into the recess 162, while at the same time possessing sufficient rigidity properties consistent with the spraying mechanisms described herein.

In the embodiment depicted, the base 102 of the dispenser 100 is imparted with a specific shape that provides a visual cue to the user during setup. In particular, the sleeve 106 includes a similar shape to that of the base 102, and in particular, to that of the recess 162 disposed between the shroud 150 and the dome 152. This orientation helps to ensure proper operation of the dispenser and precludes the use of sleeves 106 that may not be appropriate for the dispenser 100 or cause the dispenser 100 to work in an inappropriate manner.

After the dispenser 100 components are assembled, the dispenser 100 is in a rest state wherein a top end of the dome 152, i.e., the actuator nozzle 166 and stem socket 218, is in physical communication with the distal end of the container 104 (e.g., the distal end 216 of the valve stem 212) and the protrusions 170 are positioned within the openings 128 of the members 124. As illustrated in FIGS. 1 and 2, in the rest state, the lower edge of the lower housing 108 extends from the aperture 168 and is held adjacent a support surface (not shown). The container 104 is prevented from further inward movement within the base 102 through the interaction of the valve stem 212 exerting a force against the actuator nozzle 166, which itself interacts with the raised circular surface 181 on the dome 152. In this way, the weight of the upper housing 110 rests upon the actuator nozzle 166, and a spring (not shown) contained within a valve assembly (not shown) supports the upper housing 110 above the lower housing 108.

Exertion of a downward force component onto the upper housing 110 (e.g., the shroud 150 or the dome 152) causes same to move axially downward, i.e., in a direction parallel to a longitudinal axis C (see FIG. 2) in relation to the upper housing 110, thereby causing compression of the valve stem 212 and the resultant release of the contents of the aerosol container 104. Although any portion of the upper housing 110 may be axially depressed, it is contemplated that it may be more convenient for the user to grip the shroud 150 during actuation due to the sleeve 106 being disposed on the dome 152, which could obstruct a user's hand during actuation.

After manual actuation, the upper housing 110 returns to its original position upon release of the downward force by means of the spring disposed within the valve assembly of the container 104. Additional means for supporting the weight of the housing and returning same to a pre-operative position are also envisioned in a manner known in the art.

An advantage to actuating the dispenser 100 in the present embodiment is that a user may release the composition from the container 104 while minimizing direct exposure to the composition, as the user need not place their hand on the actuator nozzle 166. In addition, the combination of the relatively tall sleeve 106 further minimizes direct exposure to a user upon release of the composition by directing the composition at least partially vertically as well as restricting the amount of composition emitted directly into the immediate environment.

During actuation, the aerosol composition is released from the container 104 and exits the valve stem 212 at the distal end 216. The aerosol composition is released into the chamber 192 of the actuator nozzle 166 and is dispensed therefrom through the outlet ports 190*a*-190*d*. As shown in FIG. 20, when the aerosol composition exits the outlet ports 190*a*-190*d*, the aerosol composition disperses into one or more streams 300 that may have a spray pattern that results in, for example, primary 302, secondary 304, and tertiary 306 vectors due to deflections off of the interior surface 232 of the sleeve 106. Indeed, any number of deflections may occur.

The stream 300 is split according to the number of outlet ports 190 present in the actuator nozzle 166. In the embodiment shown in FIG. 21, four streams 300*a*, 300*b*, 300*c*, 300*d* are provided from the outlet ports 190*a*-190*d*, respectively. The streams 300*a*-300*d* are generally directed at the interior surfaces 232 of each of the sides 244*a*-244*d*. In particular, the streams 300*a*-300*d* exit the actuator nozzle 166 at a specified contact angle that balances the quantity of composition that is to be provided on the interior walls 232, and the quantity of the composition that is to be released in the plume.

The contact angle (e.g., angle of incidence) between the active present in the streams 300*a*-300*d* and the sleeve material, in part, determines the wettability thereof. The contact angle also controls spreading of the active and the size of the wetted area for a given amount of active. For a small contact angle (e.g., less than about 30 degrees), the liquid will have a relatively small spread across the sleeve material and will likely enter straight into or through a sleeve wall if comprised of an absorbent material, whereas the liquid will remain more spherical shaped and thus bead up and/or exit the sleeve 106 directly at a higher contact angle (e.g., greater than about 70 degrees). The contact angle is preferably measured relative to a longitudinal axis of one or more of the container, substrate, base, or conduit. For example, in the present embodiment, the contact angle may be measured relative to the axis C of the conduit.

Therefore, the contact angle between the streams 300*a*-300*d* and the sleeve 106 may be provided between about 30 degrees to about 80 degrees or about 30 degrees to about 70 degrees. In other embodiments, the contact angle is at least about 40 degrees. In different embodiments, the contact angle is between about 45 degrees and about 85 degrees. In a further embodiment, the contact angle is between about 50 degrees and about 90 degrees. In an additional embodiment, the contact angle is between about 55 degrees to about 66 degrees. In one specific embodiment, the contact angle is about 30 degrees. In another embodiment, the contact angle is about 40 degrees. In a different embodiment, the contact angle is about 50 degrees. In a further embodiment, the contact angle is about 60 degrees. In still a further embodiment, the contact angle is about 60 degrees. In a further embodiment, the contact angle is not less than about 30 degrees and not more than about 80 degrees.

Upon actuation, one or more streams 300*a*-300*d* of fluid travel out of the actuator nozzle 166 and into the channel 242 defining the sleeve 106, as described in detail below. The streams of composition dispensed from the actuator nozzle 166 provide different functionality according to various dispenser properties. For example, it is contemplated that one or more streams may pass directly through the sleeve 106 into the external environment to provide immediate active diffusion. In one embodiment, the amount of composition that passes directly through the sleeve 106 wall is minimized such that a majority of the composition will be retained within the sleeve 106 (e.g., either on or in the interior wall 232 of the sleeve 106 or in the plume). In another embodiment, the amount of composition passing directly through the sleeve 106 wall may be increased to provide a larger initial "burst" of composition.

One or more streams also contact the interior surface 232 of the sleeve 106 and are at least partially absorbed thereby. The streams contacting the interior surface 232 form a wetted spot, whereby the composition absorbed into the sleeve 106 is partially actively emitted, but the majority of the absorbed composition is passively emitted for a time period after the initial actuation.

Additionally, one or more streams may also form a plume, whereby at least part of the plume is retained with the sleeve 106 and at least part of the plume travels out through the upper opening 238 of the sleeve 106. In other embodiments, the plume may be characterized as exiting the sleeve 106 through an outlet or an outlet opening/orifice, discharge opening/orifice, an upper end, an exit aperture, etc., of the sleeve, conduit, or substrate. The plume also provides an initial active burst upon manual actuation and continues to actively emanate for a short time period after the formation thereof.

More particularly and with specific reference to FIG. 22, upon release, a first quantity 308*a*-308*d* of the streams 300*a*-300*d* formed of small particles of the aerosol composition may exit through the sleeve 106 directly through the sides 244*a*-244*d* to create an immediate effect on the surrounding environment. In this embodiment, the significant amount of composition traveling directly through the sleeve 106 provides a larger (e.g., active) burst of composition as compared to the other embodiments and may be desirable for certain applications.

As shown in FIGS. 21 and 22, a second quantity 310*a*-310*d* of the streams 300*a*-300*d* is deposited on the interior surfaces 232 of the sleeve 106 of each of the sides 244*a*-

244*d* and may permeate through the sleeve 106 immediately and/or over time. When the streams 300*a*-300*d* contact the sleeve 106, the material of the sleeve 106 is wetted and provides a visual contrast with the dry portions of the sleeve 106. After spraying, one or more spots 310 (shown individually as 310*a*, 310*b*, 310*c*, and 310*d*) are provided on one or more of the sides 244*a*-244*d* that comprise the wetted area.

Figure 23:
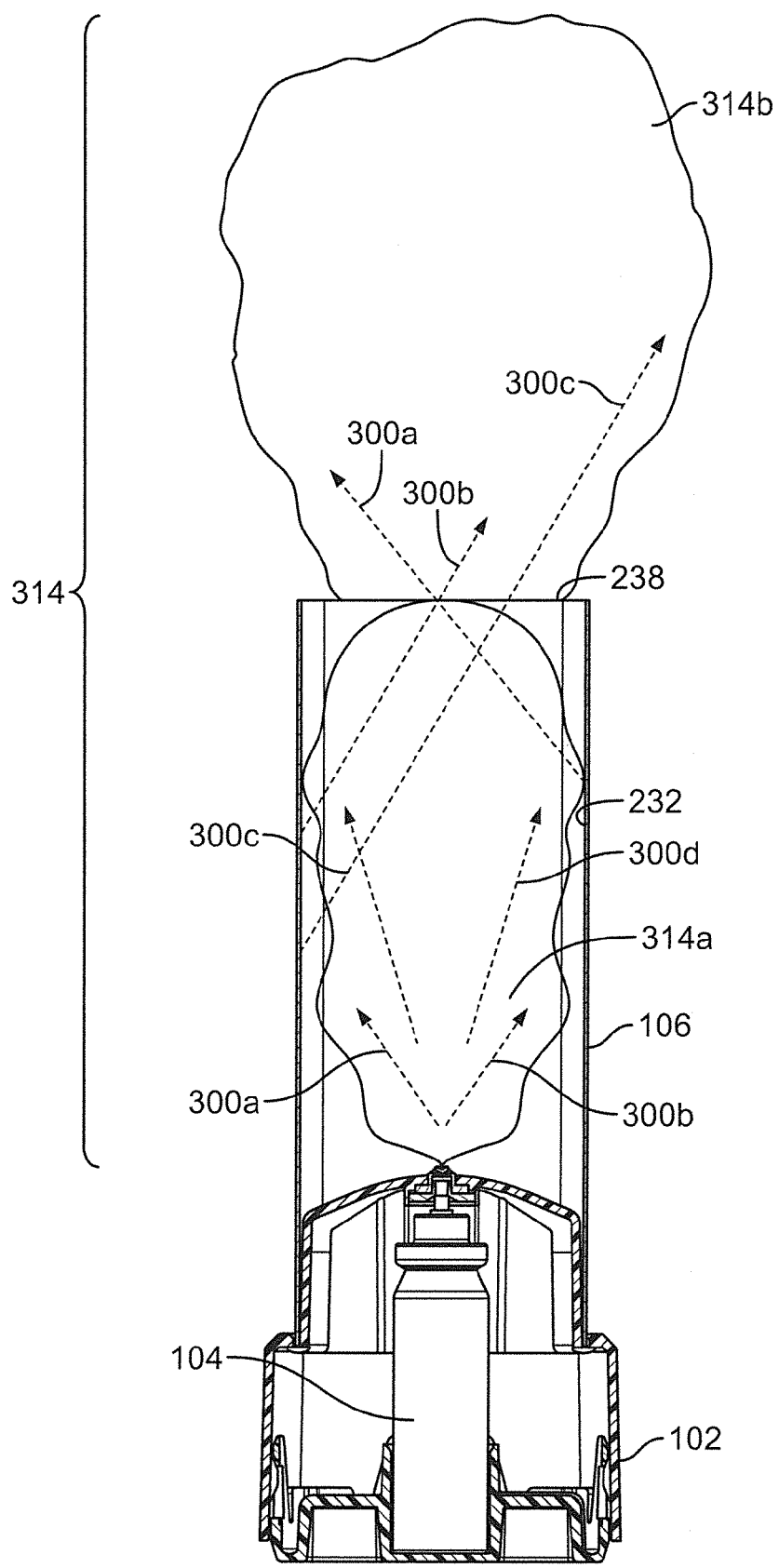
FIG. 23 is a partial cross-sectional side view of the dispenser of FIG. 1 depicting a plume.

As depicted in FIG. 23, a third quantity 312 of the streams 300*a*-300*d* is created by deflection of the streams 300*a*-300*d* off of the interior surface 232. Portions of streams 300*a*-300*d* combine to form a plume 314 having an internal component 314*a* and an external component 314*b*. In particular, a portion of the plume 314*a* stays within the sleeve 106 and a portion of the plume 314*b* exits through the upper opening 238 thereof.

In this way, the dispenser 100 creates multiple quantities of aerosol composition with different emanation rates due to the interaction with the sleeve 106. Upon manual actuation of the dispenser, one or more of the stream quantities 308*a*-308*d*, 310*a*-310*d*, 312*a*-312*d* may provide active and passive dispensing.

It is contemplated that the selection of numerous dispenser 100 parameters are important to realizing the advantages discussed herein. In particular, some important factors are those that impact the formation of the spots 310*a*-310*d* and the passive emanation created thereby, and the formation of the plume 314 and the active emanation generated thereby. Additionally, the properties of the composition prior to and during actuation are also important.

First, with respect to the formation of the spots 310, a visible presence of a wetted area on the sleeve 106 indicates to the user that the active ingredient is present on the sleeve 106 and will thereafter be released. The wetted area is created as a result of the carrier solvent contacting the sleeve 106 rather than the active. In some instances, it is also contemplated that the size of the wetted area may correlate to, and give the impression of, the amount of flowable medium dispensed. For example, two actuations of the dispenser 100 may provide a larger wetted area than a single actuation.

To provide a visible change to the sleeve 106 a number of mechanisms are useful. For example, in one instance, the composition fills the voids in the porous material of the sleeve 106. In this instance, the sleeve 106 material must include voids, the void fraction must be sufficiently large to be capable of receiving the composition, and the amount of composition deposited onto the material must be sufficient enough to fill the voids. In another instance, the composition increases the opacity of the sleeve. In this instance, the composition absorbs light such that the color of the sleeve 106 changes upon contact with the composition. In this case, the composition selectively absorbs a selection of the visible spectrum.

For the wetted area to be visible in a suitable time frame, it needs to form quickly. The formation time depends on the wicking properties of the sleeve 106 material. One important component is the presence of interconnecting pores on the material of the sleeve 106 to provide an open structure.

The size of the wetted area also depends upon the area on which the composition is deposited, which is a function of the cone angle of the actuator nozzle 166 and the spread of the deposited composition across the surface. Surface spread is a function of the surface energy, and the amount deposited (e.g., the fraction of the dose of composition from a single actuation that is deposited versus that distributed in the plume). It may be desirable to tailor the dispenser properties to ensure that the size of the wetted area correlates with the volume deposited to demonstrate that multiple actuations deposit more formulation.

The formation time of the visible wetted area depends on the wicking speed of the sleeve 106 material. Dispersion of the visible wetted area is related to the wetted area becoming too thin to be visible, which is a result of the composition spreading too widely over the surface of the sleeve 106, and/or due to evaporation removing enough liquid so that the layer of composition is too thin to be visible.

It is contemplated that in taking all of the above into consideration, the spots 310 present on the sleeve 106 after actuation may be characterized by the following parameters.

The spots 310 appear on the sleeve 106 in an approximately elliptical shape using the (conically shaped) actuator nozzle 166 described herein. The maximum height dimension and width dimensions of the spots 310 provide an absorption area on the sleeve 106. The spots 310 each include a maximum height dimension of about 30 mm to about 40 mm, and more particularly between about 32 mm to about 38 mm. In one specific embodiment, the maximum height dimension of each of the spots 310 is about 35 mm. Additionally, each of the spots 310 includes a maximum width dimension of between about 20 mm to about 30 mm, and more particularly between about 22 mm to about 28 mm. In one specific embodiment, the maximum width dimension of each of the spots 310 is about 25 mm.

In some embodiments, the maximum height dimension of each of the spots 310 is characterized as a function of the height of the sleeve 106. For instance, using a sleeve 106 having a height dimension of about 170 mm, the maximum height of each of the spots 310 is approximately ⅕ the height of the sleeve 106.

The spots 310 are further defined by an average area parameter as determined after a selected time period. In particular, the spots 310 have an area of about 2 $cm^2$ to about 14 $cm^2$, and more particularly between about 6 $cm^2$ to about 10 $cm^2$, after 10 seconds. In one specific embodiment, the spots 310 are characterized as having an area of about 8 $cm^2$ after 10 seconds.

It is also envisioned that spot 310 absorption and diffusion properties may be defined according to the time it takes for the spot 310 to visually develop most prominently after actuation. In particular, the spots 310 are most prominent after a time period of about 100 seconds to about 140 seconds, and more particularly from about 105 seconds to about 135 seconds. In one specific embodiment, the spots 310 are most prominent after a time period of about 120 seconds.

The spots 310 may also be characterized by their respective absorption and diffusion properties through the length of time that the spot is visible on the sleeve 106. More particularly, the spots 310 are visible for a discrete amount of time after actuation. In particular, in one embodiment, at least some of the spots 310 are each visible for a time between 0.1 seconds after actuation to about 420 seconds after actuation. In another embodiment, the spots 310 are each visible for a time between 0.1 seconds after actuation to about 360 seconds after actuation. In a further embodiment, the spots 310 are each visible for a time between 0.1 seconds after actuation to about 300 seconds after actuation.

The maximum absorption capacity of the sleeve 106 impacts spot 310 formation and can be determined by measuring the change in mass of the sleeve when the sleeve is fully immersed in the solvent. The change in mass of the sleeve sample can then be used to calculate the maximum solution absorbed per surface area of material (i.e., the maximum absorption capacity). It is contemplated that one embodiment of the sleeve 106 is defined by a sample area of about 408 mm$^2$, and absorbs about 58 mg of solvent, which results in a mass of solvent absorbed per surface area of about 0.14 mg/mm$^2$. In another embodiment, the sleeve 106 is defined by a sample area of about 418 mm$^2$, and absorbs about 55 mg of solvent, which results in a mass of solvent absorbed per surface area of about 0.13 mg/mm$^2$. In a further embodiment, the sleeve 106 is defined by a sample area of about 425 mm$^2$, and absorbs about 72 mg of solvent, which results in a mass of solvent absorbed per surface area of about 0.17 mg/mm$^2$.

Therefore, in addition to other parameters discussed herein, a sleeve material having the following properties is useful in conjunction with the dispenser 100 described herein. The sleeve material preferably has the capability to absorb solvent on a per surface area basis of at least about 0.1 mg/mm$^2$. In another embodiment, the sleeve material has the capability to absorb solvent on a per surface area basis of at least about 0.12 mg/mm$^2$. In another embodiment, the sleeve material has the capability to absorb solvent on a per surface area basis of at least about 0.13 mg/mm$^2$. In a further embodiment, the sleeve material preferably has the capability to absorb solvent on a per surface area basis of at least about 0.14 mg/mm$^2$. Additionally, too much absorption of the solvent on the sleeve 106 may result in a smaller plume than desired or necessary to be effective in generating a visual indicator. In one embodiment, the sleeve material preferably does not absorb solvent on a per surface area basis in an amount greater than about 0.2 mg/mm$^2$.

The sleeve 106 material may also be characterized according to one or more wicking properties associated therewith. In particular, one embodiment of sleeve 106 has an absorption height of about 100 mm, a surface area of about 3122 mm$^2$, an amount of solvent absorbed of about 201 mg, a time to complete absorption of about 18 seconds, a mass of the formula absorbed per surface area of about 0.065 mg/mm$^2$, and a wicking speed of about 0.09 mm/s. In another embodiment, the sleeve 106 has an absorption height of about 101 mm, a surface area of about 2939 mm$^2$, an amount of solvent absorbed of about 192 mg, a time to complete absorption of about 14 seconds, a mass of the formula absorbed per surface area of about 0.065 mg/mm$^2$, and a wicking speed of about 0.1 mm/s. In a further embodiment, the sleeve 106 has an absorption height of about 101 mm, a surface area of about 3073 mm$^2$, an amount of solvent absorbed of about 166 mg, a time to complete absorption of about 20 seconds, a mass of the formula absorbed per surface area of about 0.05 mg/mm$^2$, and a wicking speed of about 0.08 mm/s.

Therefore, a sleeve material having the following properties is useful in conjunction with the dispenser 100 described herein. The sleeve material has a wicking speed of at least about 0.06 mm/s. In another embodiment, the sleeve material has a wicking speed of at least about 0.07 mm/s. In a further embodiment, the sleeve material has a wicking speed of at least about 0.08 mm/s. In another embodiment, the sleeve material has a wicking speed of at least about 0.09 mm/s. In one specific embodiment, the sleeve material has a wicking speed between about 0.06 mm/s to about 0.1 mm/s.

A variety of factors impact the formation and dispersion of the plume 314. Therefore, numerous parameters are important for providing a plume that is visible above the sleeve 106 immediately after actuation. One factor that should be considered is the volume of formulation dispersed in the plume, which is a function of the amount of formulation dispensed and the relative proportion deposited on the sleeve 106 versus dispersed as droplets in the air, which in turn is related to the velocity of the spray exiting the actuator nozzle 166. Another factor that should be considered is the density of the plume of droplets. Density of the plume is a function of the distribution of the aerosolized droplets from the actuator nozzle 166, the dispersion of the aerosol composition over time, and the evaporation rate of the droplets that make up the aerosol composition.

An additional factor to be considered is the longevity of the plume of droplets. The longevity of the plume is a function of the dispersion of the aerosol composition over time and the evaporation rate of the droplets that make up the aerosol composition, in addition to the droplet size distribution, which effects how quickly the droplets sink under gravity. Another factor to be considered includes the specific location of the plume of droplets. The specific location is related to the distance traveled by the plume and the concentration effect of constraining the plume within the sleeve 106. A further factor is the visibility of the individual droplets, which is a function of the droplet size and their ability to scatter light.

Therefore, an effective plume should comprise one or more of the characteristics described herein to provide a visual indicator, as described in more detail below. One important characteristic is that the plume comprises a sufficiently large number of liquid droplets or particles of a size that can either be detected directly or that affect light by scattering in a way similar to fog to make them visible as a collective. Additionally, a proportion of the plume large enough to be visible needs to rise sufficiently high up out of the sleeve 106 to be seen and remain there for a suitable length of time to give visual confirmation of dispenser 100 activation. Accordingly, plumes having the following characteristics have been shown to meet the above criteria.

It was originally theorized that the size distribution within the plume needed to approximate that of a fog or mist, which generally requires a droplet or particle size in excess of about 50 microns (if the droplets were to be observed individually). In some instances, the droplet size may be in excess of about 40 microns. In other instances, the droplet size may be in excess of about 60 microns. In other instances, the droplet size may be in excess of about 70 microns. In other instances, the droplet size may be in excess of about 80 microns. In some instances, the droplet size is greater than about 50 microns.

Surprisingly, it has been found that although the liquid properties impact the size distribution of the plume, the make-up of the aerosol composition does not impact the size distribution within the plume because the droplets will scatter light provided that they are of a suitable size range—microns to tens of microns—irrespective of the make-up of the liquid.

For the plume to have a sufficiently large visual contrast with the ambient air so that it can be observed, the plume should have a volume of at least 800 drops/cm$^3$ (assuming water concentrations of 0.0013 g/m$^3$ of the drops), which causes reduced transparency and becomes visible. In other embodiments, the plume may have a volume of at least about 700 drops/cm$^3$. In one specific embodiment, the plume has a volume of about 820 drops/cm$^3$. In another embodiment, the plume has a volume of about 800 drops/cm$^3$. In a different embodiment, the plume has a volume of about 810 drops/cm$^3$. In a further embodiment, the plume has a volume of about 840 drops/cm$^3$. In still a further embodiment, the plume has a volume of about 850 drops/cm$^3$.

Using various parameters described herein, the droplet density within the air space enclosed by the sleeve can be estimated, assuming a homogenous distribution of monodispersed droplets. To calculate the estimated droplet density, numerous assumptions were used. In particular, it was assumed that once the flowable medium has been released from the container, the portion of the flowable medium not deposited on the sleeve material forms droplets within the sleeve volume. It was also assumed that only the volume above the actuator nozzle is filled with droplets and that no droplets have left the volume defined by the sleeve yet. It was further assumed that droplets fill the shade area homogenously and that all droplets are assumed to be of the median droplet size measured for a 0.51 mm actuator nozzle at a height of 70 mm (approximated as 20 microns). It was also assumed that all droplets are formed of Isopar L and that 20% by weight of the flowable medium discharged into the air space is Isopar L. The density of Isopar L is taken to be 767 kg/m$^3$ or 767 mg/cm$^3$. Additionally, it was assumed that the sides of the sleeve are a flat rectangular shape, the top and bottom of the air space enclosed by the sleeve are of quadratic shape, and the amount of fluid dispensed into the air space and not captured by the shade is 100 mg.

The air space enclosed by the sleeve was estimated using the width of the sleeve section as 56 mm, the total height of the shade section as 172 mm, the height of the actuator nozzle (not the impact point) as about 130 mm, and the volume of enclosed air space as 407.68 cm$^3$. The number of droplets within the air space were estimated by assuming that 20 mg of Isopar L forms droplets of a diameter of 20 microns and that droplets of a 20 micron diameter have a volume of $4.19 \times 10^{-6}$ mm$^3$. It was also assumed that each droplet weighs $3.21 \times 10^{-6}$ mg. The total number of droplets estimated that could be formed from 20 mg of Isopar L approximates to $6.23 \times 10^6$. Therefore, the droplet density in the enclosed air space was estimated by dividing that number of droplets by the air space enclosed by the sleeve. In this case, the estimated droplet density was 15,000 droplets per cm$^2$. Additionally, the number of 20 micron droplets that would result in 100% saturation of a 1 cm$^3$ volume was calculated as 125,000,000. Therefore, the saturation level within the air volume enclosed by the shade is estimated to be 0.012%.

To form a plume having the characteristics herein, a sufficient amount of composition is required. In particular, in one embodiment, at least about 100 mg of liquid composition form the plume. In another embodiment, between about 75 mg and about 125 mg of liquid composition form the plume. In a further embodiment, between about 90 mg to about 110 mg of liquid composition form the plume. In one specific embodiment, about 100 mg of liquid forms the plume.

Additionally, the amount of liquid that is available to form the plume is determined, in part, by the spray velocity. The velocity the spray leaves the actuator nozzle 166 and subsequently impacts the sleeve 106 determines the balance between the liquid that is deposited on the sleeve 106 that is to be released over time and the liquid that forms the plume above the sleeve 106 indicating immediate actuation. The amount of droplets that impact the sleeve 106 is determined by the size distribution of the droplets and their velocity. The larger droplets have greater momentum, so as the gas flow is deflected by the sleeve 106, the larger droplets continue their trajectory and impact the sleeve 106. Smaller droplets have lower momentum and are carried with the flow. The velocity of the gas flow changes the boundary between the droplets that have sufficient momentum to hit the sleeve 106, and the droplets that continue to be carried by the gas. The slower the gas flow, the greater the proportion that remains aerosolized.

The interaction between a droplet and the sleeve 106 at the time the drop impacts the sleeve 106 is influenced by the balance between the kinetic energy of the drop and the surface tension of the drop. Before the drop impacts the sleeve 106, it mainly includes kinetic energy. As the drop impacts the sleeve 106, it is deformed and its surface energy is increased. Whether the drop remains on the sleeve 106 or bounces off depends on the balance of kinetic energy and surface energy. For moderate initial energies, as influenced by the droplet material and sleeve 106 material, the drop is likely to bounce off of the sleeve 106. For large initial energies, the drop is likely to spread upon impact.

The direction of the droplets as they leave the actuator nozzle 166 and travel toward the sleeve 106 determines the angle at which the droplets impinge on the sleeve 106. However, the kinetic energy of the droplet along with its surface energy and the surface properties of the sleeve material generally determine whether the droplet will rebound or adhere to the sleeve 106, rather than the actual geometry of the dispenser 100. However, in some instances, surface morphology and geometry may be relevant to whether the droplet will be deposited or deflected from the sleeve 106.

For the plume to be visible to the user, it needs to be visible above the height of the sleeve. Therefore, the plume moves at a velocity that allows it to reach a height greater than that of the sleeve before the droplets are stopped by air friction and gravity and start descending toward the dispenser 100. Droplets having a 10 micron diameter fall at speeds of about 1 cm/s and droplets having about a 50 micron diameter fall at speeds of about 26 cm/s. In one embodiment, the flowable medium forms a plume that exits the upper end of the substrate 230 with a velocity of between about 4 m/s to about 10 m/s. In another embodiment, portions of the plume extend at least 100 mm above the upper end of the substrate. In a further embodiment, the plume has a velocity of at least 0.10 m/s at 100 mm above the upper end of the substrate.

The plume will be visible above the sleeve for a wide range of angles by the user. Within the sleeve, the plume will only be visible to a user looking downwards into the sleeve.

For the droplets to form a visible plume, it is also helpful that the evaporation rate from the droplets is low enough so that the droplets continue to scatter light while the droplets are sufficiently dense to cause a visible effect. Evaporation is a function of material volatility, temperature of the location, as well as the surface area of the droplet.

The plume generated by the dispenser 100 and disposed therein may be characterized by a hang time, which is the time the plume remains visible within or above the sleeve 106. Hang time is an important visual cue to the user that the active formula has been dispensed and is being absorbed onto the sleeve substrate or emitted into the atmosphere. To form the plume, the base acts as a mechanism for discharging the flowable medium through the substrate 230. In turn, discharge of the flowable medium through the substrate 230 and/or channel 242 results in a visible plume of the flowable medium.

After formation, at least a portion of the plume is present within the channel 242 defined by the sleeve 106, assuming a sleeve 106 is being utilized with the base 102. In one embodiment, at least a portion of the plume travels out of the channel 242 and is visible beyond a boundary of the substrate. The boundary may be an upper boundary, a lower boundary, a lateral boundary, or an imaginary boundary formed by an open surface of the sleeve 106 (e.g., outlet opening 238). In one embodiment, the plume is visible beyond the boundary of the substrate for at least 1 second. In another embodiment, the plume is visible beyond the boundary of the substrate for between 1 second to 2 seconds. In a further embodiment, the plume is visible beyond the boundary of the substrate for at least 3 seconds. In one specific embodiment, the plume of flowable medium is visible beyond the boundary formed by the outlet opening 238. In a further embodiment, the substrate 230 comprises a shade having a channel in which the flowable medium is visible as a plume for at least 3 seconds thereabove.

Dispensers without a sleeve have an immediate aerosolized spray that typically persists for less than a second, and always less than 3 seconds. By containing the plume volume within the sleeve 106, the plume remains visible for 1 second or longer. Preferably, the plume remains visible for more than 1 second, and in a preferred embodiment the plume is visible for at least 3 seconds. In another embodiment, the plume is visible for at least 8 seconds. In one preferred embodiment, the plume remains visible from about 8 seconds up to about 16 seconds depending on a variety of factors. Notably, the plume hang time is different depending on the number of outlet ports 190 used in the actuator nozzle 166 and/or the discharge volume of the flowable medium.

Therefore, the plume generated by the dispenser 100 is characterized by a hang time of between about 3 seconds to about 60 seconds, more preferably between about 5 seconds to about 30 seconds, and even more preferably between about 8 seconds to about 16 seconds in the dispenser 100. In one particular embodiment, the hang time is about 8 seconds using a dispenser 100 with an actuator nozzle 166 having four outlet ports 190. In one particular embodiment, the hang time of the plume is about 14 seconds using a dispenser 100 with an actuator nozzle 166 having six outlet ports 190. It is also contemplated that a plume may be generated with a nozzle having one or more ports, which may have a plume hang time of 3 or more seconds.

An additional surprising characteristic of the plume generated by an actuator nozzle 166 with six outlet ports 190 is the shape of the plume, which is different from the shape of the plume generated by an actuator nozzle 166 with four outlet ports 190. In particular, the shape of the plume using a four port actuator nozzle is generally characterized as a cloud or a puff. In contrast, the shape of the plume using a six port actuator nozzle is characterized as a vortex. In one embodiment, the vortex plume moves through and out of the sleeve 106 in a clockwise spiral pattern. Further, the vortex plume of the six port actuator nozzle is visible for just under twice as long as the plume of the four port actuator nozzle.

A related characteristic of the plume is the persistence time. Persistence time is an important visual cue to the user that the active formula has been dispensed. By containing the plume volume within the sleeve, the plume is observable above the sleeve for about 1 second to about 2 seconds. In one embodiment, the four outlet port actuator nozzle is characterized by a plume persistence time of between about 1.6 seconds to about 2.4 seconds. In another embodiment, the four outlet port actuator nozzle is characterized by a plume persistence time of between about 1.8 seconds to about 2.2 seconds. In a further embodiment, the four outlet port actuator nozzle is characterized by a plume persistence time of about 2 seconds. In one embodiment, the six outlet port actuator nozzle is characterized by a plume persistence time of between about 1 second to about 1.4 seconds. In a further embodiment, the six outlet port actuator nozzle is characterized by a plume persistence time of about 1.2 seconds.

Another characteristic of the dispenser 100 and associated components include the amount of composition that is absorbed into the sleeve 106 for passive diffusion, as compared to the amount of composition released into the atmosphere for active diffusion. In one embodiment, the amount of composition absorbed into the sleeve 106 is between about 0.05 g to about 0.4 g. In another embodiment, the amount of composition absorbed into the sleeve is between about 0.1 g to about 0.3 g. In a further embodiment, the amount of composition absorbed into the sleeve is between about 0.1 g to about 0.2 g. In a different embodiment, the amount of composition absorbed into the sleeve is at least about 0.1 g and not more than about 0.5 g.

In one embodiment, the amount of composition released into the atmosphere is between about 0.2 g to about 2 g. In another embodiment, the amount of composition released into the atmosphere is between about 0.2 g to about 1 g. In a further embodiment, the amount of composition released into the atmosphere is between about 0.2 g to about 0.8 g. In a different embodiment, the amount of composition released into the atmosphere is at least about 0.2 g and not more than about 1 g.

Therefore, the ratio of the amount of composition absorbed into the sleeve as compared to the amount of composition released into the atmosphere is about 1 to about 1. In another embodiment, the ratio of the amount of composition absorbed into the sleeve as compared to the amount of composition released into the atmosphere is about 1 to about 4. In some embodiments, the ratio of the amount of composition absorbed into the sleeve as compared to the amount of composition released into the atmosphere is about 1 to about 6. In a further embodiment, the ratio of the amount of composition absorbed into the sleeve as compared to the amount of composition released into the atmosphere is about 1 to about 8. In different embodiments, the ratio of the amount of composition absorbed into the sleeve as compared to the amount of composition released into the atmosphere is about 4 to about 1. Further, the ratio decreases as the sleeve 106 is reutilized through additional actuation cycles.

A number of interrelated factors contribute to the performance of the dispenser 100, including the material of the sleeve 106, any surface treatment applied thereto, the actuator nozzle 166 design, the spray pattern emitted by the actuator nozzle 166, the spray location, the dosing quantity, the concentration of active and the selection of the aerosol container 104 and the aerosol composition.

During and after actuation, a plurality of indicators are provided through various features of the dispenser 100 that allow a user to determine if the initial manual actuation was successful and in the continued efficacy of the flowable medium. One or more of the indicators are provided in the form of a visual indicator and an audible indicator. The visual indicators are provided in at least three particular forms.

A first visual indicator is provided in the form of the material selected for use as the sleeve 106, discussed previously herein. The sleeve 106 material provides an immediate cue to the user that the sleeve 106 is permeable and that an aerosol composition will be at least partially absorbed therein and thereafter passively emitted therefrom.

For the user to believe that the active material can emanate from the sleeve material, the material should provide one or more visual cues to both its fluid interaction properties and tactile properties. In particular, a material having a visible pore size and texture, and a fabric-like feel suggests to the user that the material will behave like fabric and let a liquid absorb into and emanate therefrom.

Without being bound by theory, it is believed that the user's perception of the efficacy of the passive emanation from the sleeve 106 of the dispenser 100 is based upon being told how the dispenser works, observing a plume (described in detail below), and perceiving the sleeve material to be something that appears to have the properties that would facilitate the dispenser 100 operation. Therefore, a sleeve 106 material should comprise a material that provides the visual appearance of a material that will absorb a fluid to perform the emanation function, while at the same time possess enough rigidity to form the sleeve 106.

The types of materials that users see as being absorbent are papers and other non-wovens, along with woven fabrics and other textiles. Therefore, the sleeve material should exhibit visual characteristic properties of these classes of materials such as being fibrous, having pores, having texture, and being low density.

In addition, the user is likely to assess the perceived quality of the sleeve 106 material from visual and tactile observations of the material. For example, for a material to be light and able to support itself as a sleeve 106, the material should possess a low density and sufficient stiffness to prevent bending under its own weight, which gives the perception that the material will be able to remain positioned within the base 102. Additionally, the material should be damage resistant and retain its texture and form during handling (installation) and use (coating with formulation, evaporation and emanation of the active).

A second visual indicator is provided in the form of a visible plume (see FIG. 23). In one embodiment, the second visual indicator may have a fog-like appearance. In this embodiment, the second visual indicator is visible for at least 3 seconds. In another embodiment, the visual indicator is visible for between 8 seconds and 16 seconds. In a different embodiment, the second visual indicator may have the appearance of a cloud or fog. In a further embodiment, the plume comprises a plurality of suspended particles or droplets. Activation of the dispenser 100 is immediately apparent to the user by the presence of a visible plume, either above and/or within the sleeve 106.

In many instances, the user is able to observe the plume as it exits the outlet opening 238 of the sleeve 106. Once the plume has left the sleeve 106, droplets can either sink back into the volume enclosed by the sleeve 106 or be moved away from the sleeve 106 by airflow. Once the plume is no longer constrained by the sleeve 106, it can grow through entraining air. As the plume entrains air and is dispersed, the concentration of droplets or particles per unit volume in the plume will reduce, thereby reducing the visibility of the plume until it can no longer be visually perceived by a user. In some instances, the user may be able to observe the plume within the sleeve 106 due to a favorable viewing angle.

A third visual indicator is provided in the form of a visible discoloration on the sleeve 106 formed by the depositing of the flowable medium thereon. In one embodiment, the visual indicator appears to contrast in color to a surface adjacent thereto. In a different embodiment, the visual indicator appears darker in color than a surface adjacent thereto. In a further embodiment, the third visual indicator provides a visual indication of efficacy for a time period that is greater than that of the second visual indicator (e.g., the length of time the plume is visible). In a further embodiment, the visual indicator is created by a wetted region on the absorbent structure (e.g., the sleeve, conduit, substrate, etc.).

Numerous factors discussed previously are important for the user to be able to detect a wetted area on the sleeve 106 after actuation. In particular, enough formulation must be deposited on the sleeve 106 to create a visible change. Further, the wetted area must be visible quickly after actuation so that the user is still present to see it, and the wetted area should last long enough such that the user has time to observe it. Further, the wetted area must comprise a large enough surface area such that one or more of the spots 310 is able to be seen.

Some amount of the flowable medium deposited on the internal surface 132 of the sleeve 106 is actively diffused along with the flowable medium comprising the plume. However, a significant quantity is provided on the sleeve 106, which is passively emitted thereafter. In one embodiment, a dispensing system includes a shade having an interior volume and a mechanism for discharging a flowable medium. The discharging of the flowable medium onto the shade imparts a wet spot that is visible for a time period $t_1$, which is longer than a period of time $t_2$ that the flowable medium is visible when suspended in the atmosphere as a plume.

In another embodiment, a discharge stream of the flowable medium may be discharged onto a surface defining the channel, wherein an external surface of the substrate is imparted with at least one wet spot that is most visually pronounced about 2 minutes after the discharge of the flowable medium. Also, the at least one discharge stream of the flowable medium may be discharged onto a surface defining the channel, and wherein an external surface of the substrate is imparted with at least one wet spot having an average size of greater than or equal to 8 $cm^2$ ten seconds after the discharge of the flowable medium.

In a further embodiment, a dispensing system comprises a shade and a base for retaining the shade, wherein the discharge of a flowable medium into the shade results in a visible wet spot of the flowable medium on a surface of the shade for a time period $t_1$ and a visible plume of the flowable medium within the shade for a time period $t_2$, and wherein $t_2 < t_1$. It is also contemplated that the visible plume of the flowable medium may be visible outside of the shade for a time period of $t_3$, wherein $t_3 < t_2$. Further, it is also contemplated that the shade may comprise a nylon and that the visible wet spot is substantially not visible 6 minutes after the discharge of the flowable medium.

Numerous combinations of the visual and/or audible indicators are provided. For example, in one embodiment, a dispensing system comprises an absorbent substrate and a mechanism for discharging a flowable medium through the absorbent substrate. The discharging of the flowable medium creates an audible indicator that the flowable medium has been discharged. Further, the discharging of the flowable medium through the absorbent structure also creates a first visual indicator in the form of a plume of suspended particles and a second visual indicator in the form of a wetted region of the absorbent structure, which are visible by a user during use of the dispensing system. It is contemplated that the discharge of the flowable medium may be through or otherwise into a channel or conduit of the substrate.

In addition to the visual indicators, one or more audible indicators are contemplated. For example, a first audible indicator is provided in the form of any audible cue that is generally discernible by a user. One audible indicator is a "hiss" sound associated with aerosol dispensing systems.

Other exemplary audible indicators include snaps, beeps, pops, chimes, a voice, music, and sound effects. In general, any audible cue capable of notifying a user of the dispensing and/or a change in the dispensing is appropriate for use herein. In one embodiment, the audible indicator is provided prior to the second and/or third visual indicators. In a different embodiment, the audible indicator is provided at substantially the same time as the second visual indicator. In another embodiment, the audible indicator is provided at a time period when the dispenser 100 has stopped passively emanating the flowable medium. In a different embodiment, the audible indicator alerts the user that one of the second and/or third visual indicators have terminated.

It is envisioned that one or more of the indicators are used in combination to effectively communicate the active and continued passive emanation of the dispenser 100.

Data and Examples

Numerous non-limiting examples of dispensing systems have been contemplated to demonstrate the properties discussed herein. More particularly, tests were conducted to demonstrate the impact that the selection of the properties relating to the container, the composition within the container, the base, and the sleeve, have on the dispensing capabilities of the dispenser. The examples are given solely for the purpose of illustration and are not to be construed as limitations of the present invention, as many variations thereof are possible without departing from the spirit and scope of the invention, which would be recognized by one of ordinary skill in the art.

In the examples, all concentrations are listed as weight percent, unless otherwise specified. Numerous examples below utilize materials considered for the sleeve, which are listed in Table 1 below. The materials referenced in the following examples are the materials listed in Table 1 unless otherwise noted.

TABLE 1

| Material | Supplier | Specific Detail |
| --- | --- | --- |
| Nylon | Cerex Advanced Fabrics | Cerex ® 23200 |
| Fiberglass | Crane Nonwovens | Craneglass ® 230 |
| PET Film | DuPont Teijin Films | Mylar 850 |
| Coffee Filter Paper | Purico Group | Purico 235 mm PT LFF |
| Polyester | Crane Nonwovens | Cranemat ® RS |

The composition used in the following examples is the composition listed in Table 2 unless otherwise noted. In some examples as noted, 100% of Isopar L is used, which is a high purity isoparaffin fluid manufactured by ExxonMobil Chemical.

TABLE 2

| Ingredient | Wt. % | Role |
| --- | --- | --- |
| B-52 | 80 | Propellant |
| Isopar L | 20 | Solvent |

A system having a dispenser with either a four-port actuator nozzle or a six-port actuator nozzle is considered. The dispenser emits a plume upon actuation. The hang time of the plume of mist from a dispensed composition enclosed within a Nylon sleeve volume is considered for both types of actuator nozzles. With the sleeve disposed on the dispenser, a stop watch was started as the base was manually depressed. The watch was stopped when the plume was no longer clearly visible within the sleeve, as observed from directly above. This test was repeated two additional times, each time replacing the sleeve with an unused, fresh sleeve. The test was also repeated using the six-port actuator nozzle. Table 3 illustrates the results of the three tests for each actuator nozzle.

TABLE 3

| Outlet Ports | 1st Run | 2nd Run | 3rd Run | Average |
|---|---|---|---|---|
| 4 hole | 8 sec | 9 sec | 8 sec | 81 ± 1 sec |
| 6 hole | 16 sec | 15 sec | 12 sec | 14 ± 2 sec |

Thus, as was previously noted, dispensers without a sleeve have an immediate aerosolized spray that persists for less than a second. By containing the flowable medium discharge within a sleeve, a plume remains visible from 8 to up to 16 seconds, depending on the number of outlet ports in the actuator nozzle. It was further observed that the six-outlet port actuator nozzle produced a plume that appeared to move in a clockwise spiral pattern while it persisted. The plume produced with the six-outlet port actuator nozzle also lasted just under twice as long as the plume produced with the four-outlet port actuator nozzle.

A system comparing the weight of formulation absorbed by the Nylon sleeve to the weight of formulation released into the atmosphere when the dispenser is activated multiple times is considered. The test was conducted by measuring the change in mass of the sleeve and container after activation. This test was only conducted on the Nylon sleeve and separate sleeves were used for each test. Equipment utilized during the test included weighing scales +−0.001 gr., sleeve samples, and a formulation comprising 100% Isopar L.

The sleeve, container, and base were all weighed separately and the results were recorded. The dispenser was reassembled and activated (i.e., actuated) twice in quick succession. The sleeve was removed and the weight of the sleeve was recorded. The container and base were weighed and the results were recorded. The steps were repeated, each time increasing the number of actuations by two on each repeat.

Table 4 illustrates the weight of the sleeve and container both before and after activation. Table 4 also illustrates the mass of Isopar L absorbed on the sleeve versus the mass of Isopar L released into the atmosphere.

TABLE 4

| Number | Before Activation | | After Activation | | Mass | Mass released |
|---|---|---|---|---|---|---|
| of sprays | Sleeve Weight (g) | Container Weight (g) | Sleeve Weight (g) | Container Weight (g) | Absorbed on Sleeve (g) | into atmosphere (g) |
| 2 | 2.914 | 15.046 | 2.960 | 14.758 | 0.046 | 0.242 |
| 4 | 2.773 | 14.758 | 2.889 | 14.204 | 0.116 | 0.439 |

TABLE 4-continued

| Number of sprays | Before Activation Sleeve Weight (g) | Before Activation Container Weight (g) | After Activation Sleeve Weight (g) | After Activation Container Weight (g) | Mass Absorbed on Sleeve (g) | Mass released into atmosphere (g) |
|---|---|---|---|---|---|---|
| 6 | 2.753 | 13.365 | 2.933 | 12.510 | 0.18 | 0.675 |
| 8 | 2.770 | 12.510 | 3.033 | 11.328 | 0.263 | 0.920 |
| 10 | 2.909 | 11.328 | 3.242 | 9.973 | 0.333 | 1.0218 |

The results of Table 4 show that for up to ten activations of the device, the amount of formulation absorbed by the sleeve and released into the atmosphere increases in a linear fashion, wherein 0.046 grams are absorbed on the sleeve at two activations and 0.333 grams are absorbed within the sleeve if the dispenser is activated ten times. Similarly, the mass of spray formulation released after two sprays is 0.242 grams, whereas if the device were to be activated ten times, 1.0218 grams would be released into the surrounding atmosphere.

These results suggest that the Nylon sleeve material absorbs the formulation mass linearly with the number of activation doses up to at least ten user activations. Therefore, the user has a degree of control over the loading mass of formulation onto the sleeve and subsequent release into the environment when operating the dispenser.

A further system is considered that quantifies and compares the persistence time of the plume observed above the sleeve material. Measurements were performed for both the four and six outlet port actuator nozzles. To conduct this test, two dispensers were used, one having an actuator nozzle with four outlet ports and the other having an actuator nozzle with six outlet ports. Nylon sleeves were used, in addition to a high-speed camera, fiber optic lights, high powered halogen lights, and a tripod.

To conduct the testing, the dispenser having the formulation of Table 2 was positioned on a laboratory bench and illuminated by two high intensity halogen flood lights. The lights were only turned on directly before making measurements and extinguished after each measurement in order to prevent undue heating of the device. In addition, the vapor plume was highlighted using a dual fiber-optic light source. The lighting allowed the plume to be further illuminated without extra heating and the steerable nature of the fiber optics allowed the lighting to be optimized.

The cameras were set to 500 frames per second and recorded for 3.3 seconds. To conduct the test, the sleeve was placed on the dispenser having the four outlet port actuator nozzle. The halogen lights were turned on, the recording was started, and the dispenser base was depressed. The test was repeated using a dispenser having the six outlet port actuator nozzle. The frames of the high-speed camera were time-stamped and reviewed to determine the persistence time of the plume.

Table 5 illustrates the persistence time for the dispenser with the four outlet port actuator nozzle and the dispenser with the six outlet port actuator nozzle.

TABLE 5

| Actuator Nozzle (holes) | Persistence time (ms) | Frame rate | Image x | Image y | Gain setting |
|---|---|---|---|---|---|
| 6 | 1019 | 500 | 1280 | 1024 | 2 |
| 6 | 1365 | 500 | 1280 | 1024 | 2 |
| 6 | 1000 | 500 | 1280 | 1024 | 2 |
| 6 | 1400 | 500 | 1280 | 1024 | 2 |
| 4 | 2000 | 500 | 1280 | 1024 | 2 |
| 4 | 2000 | 500 | 1280 | 1024 | 4 |
| 4 | 1900 | 500 | 1280 | 1024 | 4 |

Thus, it can be seen from Table 5 that the dispenser with the four outlet port actuator nozzle has an average plume persistence time of around 2 seconds, while the dispenser with the six outlet port actuator nozzle has an average plume persistence time of about 1.2 seconds.

Another system is considered to determine the maximum absorption capacity of various sleeve materials. In particular, the test considered the maximum absorption capacity of Isopar M in a variety of different sleeve materials.

The determination of the maximum absorption capacity of various sleeve materials was achieved by measuring the change in mass when the sleeve was fully immersed in the Isopar formulation for a set period of time. The change in mass of the sleeve sample was used to calculate the maximum solution absorbed per surface area of material. Samples of each of a variety of sleeve materials (Nylon, PET Film, Coffee Filter Paper, Polyester, and Fiber Glass) were prepared by cutting a square of approximately 20 $mm^2$. Three samples were tested for each sleeve material type.

The length and width of the sleeve sample over at least three points was measured and the average was used. The surface area was calculated, the weight of the sample was measured, and the steps repeated for all of the samples. 4 mL of prepared formulation comprising Isopar were added to a beaker. The sleeve sample was positioned in the formulation, ensuring complete immersion while a stopwatch was started simultaneously. The sleeve sample was removed after 30 seconds to ensure no excess Isopar M. The mass of the saturated sleeve was recorded and these steps were repeated for each sample. The mass of solution absorbed per surface area of the sample was calculated. Table 6 illustrates the mass maximum absorption capability of various types of sleeve materials.

TABLE 6

| Material Sample | # | Sample Area ($mm^2$) | Mass Absorbed (mg) | Mass Absorbed per Surface Area ($mg/mm^2$) |
|---|---|---|---|---|
| Nylon | 1 | 407.91 | 57.67 | 0.141 |
| | 2 | 418.12 | 54.67 | 0.131 |
| | 3 | 425.11 | 72.2 | 0.170 |
| Fiber Glass | 1 | 425.91 | 85.75 | 0.201 |
| | 2 | 401.32 | 63.6 | 0.158 |
| | 3 | 403.79 | 70.6 | 0.175 |

TABLE 6-continued

| Material Sample | # | Sample Area (mm$^2$) | Mass Absorbed (mg) | Mass Absorbed per Surface Area (mg/mm$^2$) |
|---|---|---|---|---|
| PET Film | 1 | 414.90 | 34.04 | 0.082 |
|  | 2 | 418.34 | 37.55 | 0.090 |
|  | 3 | 420.52 | 30.89 | 0.073 |
| Coffee Filter | 1 | 406.90 | 84.82 | 0.208 |
| Paper | 2 | 391.34 | 62.01 | 0.158 |
|  | 3 | 418.41 | 67.9 | 0.162 |
| Polyester | 1 | 411.98 | 47.84 | 0.116 |
|  | 2 | 395.47 | 46.77 | 0.118 |
|  | 3 | 413.47 | 40.98 | 0.099 |

Table 7 illustrates the averaged results of the mass maximum absorption capability of various types of materials.

TABLE 7

| Material | Average Sample Area (mm$^2$) | Average Mass Absorbed (mg) | Average Mass Absorbed per Surface Area (mg/mm$^2$) |
|---|---|---|---|
| Fiber Glass | 410.34 | 73.32 | 0.18 |
| Coffee Filter Paper | 405.55 | 71.58 | 0.18 |
| Nylon | 417.04 | 61.51 | 0.15 |
| Polyester | 406.97 | 45.20 | 0.11 |
| PET Film | 417.92 | 34.16 | 0.08 |

Thus, the fiber glass and coffee filter paper had the highest maximum absorption capacity at 0.18 mg/mm$^2$. The Nylon showed a relatively high maximum absorption capacity especially in comparison with the PET Film. The Nylon reading shows that the Nylon will act as an especially good reservoir for the formulation as it will accommodate a large amount of formulation without becoming too water logged.

Referring to Table 8, a system with various sleeve materials was tested to assist in determining the size of the wetted area that is formed on the sleeve after actuation. A controlled volume of 30 µL of Isopar L was used and samples of each of the five sleeve materials (Nylon, PET Film, Coffee Filter Paper, Polyester, and Fiber Glass) were prepared using a sample size of at least 20 mm by 20 mm.

The sheet to be tested was placed on a glass plane, and Isopar L was drawn into a pipette. 30 µL drops of the Isopar L were released onto the sleeve sample from a height of 50 mm. The wetted area was marked and photographed at the 10 second mark. The dimensions of the square were recorded and the test was repeated for each sample.

Table 8 shows the average size of the wetted area (spot) for various types of materials.

TABLE 8

| Sleeve Material | Approximate Area Occupied by Wetted Area (spot) | | | Average Wet Spot Size (cm$^2$) |
|---|---|---|---|---|
|  | Sample 1 | Sample 2 | Sample 3 |  |
| Nylon | 3.5 cm × 2.5 cm | 3 cm × 3 cm | 3 cm × 4 cm | 8 |
| PET film | 2.5 cm × 2 cm | 2.5 cm × 2 cm | 3 cm × 2.5 cm | 5 |
| Coffee filter paper | 3 cm × 3 cm | 3.5 cm × 2.5 cm | 3 cm × 3 cm | 7 |
| Polyester | 3 cm × 2 cm | 3 cm × 2 cm | 3.5 cm × 2 cm | 5 |
| Fiber glass | 2 cm × 2.5 cm | 1.5 cm × 2 cm | 3 cm × 2.5 cm | 4 |

Thus, as shown by the Table 8, the Nylon showed the largest average (8.00 cm$^2$) wetted area (spot) size and therefore possesses the highest wettability with respect to Isopar L as compared to the other materials tested. The fiber glass showed the smallest average wetted area (spot) size (4 cm$^2$) and therefore possesses the lowest wettability. These results suggest that the Nylon sleeve possesses better absorbency characteristics with respect to the other materials. It is also thought that a greater amount of the composition is available for passive diffusion as a result of the absorbency characteristics of Nylon, as opposed to the composition being released into the atmosphere, either through the plume, or otherwise. Further, Nylon has the added benefit of not swelling in the Isopar solvent and/or absorbing the active into the polymer itself, unlike polyester, and therefore the active can more efficiently be stored in or on the shade 106 for more uniform emanation.

Another system is considered in Tables 9 and 10 that illustrate wicking time, percentage porosity, and the porosity of several sleeve materials. These tests show the effects that material properties have on the interaction of the composition with the sleeve material, which results in the capability to calculate pore size values. The porosity level (or Void Volume ratio) is the percentage of the sleeve that is air, i.e. the percentage of the sleeve that comprises pores.

The flow rate of an Isopar-based formulation comprising 100% Isopar M through a variety of different sleeve materials was the focus of this experiment. The absorption capacity of the sleeves was calculated, which was used to calculate the porosity ratio of the material. The calculation was achieved by measuring the change in mass when the sleeve was saturated with the Isopar formulation. The percentage change in mass was theorized to be the percentage of the porosity of the sleeve.

Samples of each of the five sleeve materials (Nylon, PET Film, Coffee Filter Paper, Polyester, and Fiber Glass) were prepared by cutting a strip approximately 3 cm wide and 10 cm high from the sleeve. The weight, height, length, and width of each of the sleeve samples was measured. The sample was measured along at least three different points and the average of the measurement was used. The density of the sleeve was calculated. These steps were repeated for each of the samples. 4 mL of Isopar was added to a beaker and the mass of the beaker with the Isopar was recorded. A tip of the sleeve sample was inserted into the beaker while simultaneously starting a stopwatch. A piece of paper towel was placed onto the tip of the sleeve. The paper towel was monitored until the formulation started soaking into it, or until the Isopar reached the top of the sleeve. The stopwatch was stopped and the time for saturation to occur was recorded. The sleeve was removed from the beaker and there was no excess Isopar M. The mass of the saturated sleeve was recorded and the previous steps were repeated for each sheet sample.

Table 9 shows the wicking speed for Isopar M to absorb through 100 mm test samples, as well as the mass of formula absorbed per surface area of the sample.

TABLE 9

| Sleeve Material | # | Absorption Height (mm) | Surface Area (mm$^2$) | Mass Absorbed (mg) | Time to Complete Absorption (hr/min/sec) | Mass of Formula absorbed per surface area (mg/mm$^2$) | Wicking Speed (mm/s) |
|---|---|---|---|---|---|---|---|
| Nylon | 1 | 100.42 | 3122.39 | 201.88 | 00:18:09 | 0.065 | 0.092 |
|  | 2 | 100.91 | 2939.40 | 191.92 | 00:14:37 | 0.065 | 0.115 |
|  | 3 | 101 | 3072.76 | 166.49 | 00:20:47 | 0.054 | 0.081 |
| Fiber Glass | 1 | 40.74 | 3956.85 | 144.50 | 3:00:00 | 40.74 | 0.023 |
|  | 2 | 24 | 3110.98 | 98.66 | 3:00:00 | 24 | 0.013 |
|  | 3 | 38.4 | 3045.11 | 106.36 | 3:00:00 | 38.4 | 0.021 |
| PET Film |  |  |  | Unable to measure |  |  |  |
| Coffee Filter Paper | 1 | 98.78 | 3010.56 | 117.04 | 00:07:32 | 0.039 | 0.219 |
|  | 2 | 101.20 | 3080.29 | 241.78 | 00:08:40 | 0.078 | 0.195 |
| Polyester | 1 | 99.96 | 3068.00 | 121.25 | 00:53:00 | 0.040 | 0.031 |
|  | 2 | 100.83 | 336.05 | 88.28 | 00:44:30 | 0.028 | 0.038 |
|  | 3 | 100.36 | 3094.77 | 71.77 | 00:28:05 | 0.023 | 0.060 |

Table 10 shows the averages of the test data in Table 9 for each material.

TABLE 10

| Material | Average Absorption Height (mm) | Average Surface Area (mm$^2$) | Average Mass Absorbed (mg) | Average Time To Complete Absorption | Mass of Formula absorbed per surface area (mg/mm$^2$) | Average Wicking Speed (mm/s) |
|---|---|---|---|---|---|---|
| Coffee Filter Paper | 99.99 | 3045.8 | 179.41 | 00:08:06 | 0.059 | 0.207 |
| Nylon | 100.78 | 3044.52 | 186.76 | 00:17:51 | 0.061 | 0.096 |
| Polyester | 100.38 | 3099.61 | 93.77 | 00:41:52 | 0.030 | 0.043 |
| Fiber Glass | 34.38 | 3044.52 | 116.51 | 03:00:00 | 0.039 | 0.019 |

As shown, the coffee filter paper and the Nylon both had relatively high absorption per surface area values. The wicking speed of the coffee filter paper was over double that of the Nylon. The test resulted in a large, but sparse wetted area (spot) on the coffee filter paper due to its increased wettability that yielded a faster and more inconsistent evaporation rate as compared to the Nylon. The Nylon had a more localized and concentrated wetted area (spot) as compared to the coffee filter paper. Therefore, the results suggest that Nylon has a lower, but more steady evaporation rate.

A different system is considered relating to the dosage per each dispense and the evaporation rates from various sleeve materials. This set of experiments used dispensers consisting of a sleeve, a container, and a base. The container included a flowable medium having B-52 in an amount of 80 wt. %, Isopar L in an amount of 18.964 wt. %, and metofluthrin active in an amount of 1.036 wt. %. The density of the metofluthrin was shown to be 1.21 g/ml, the density of the Isopar L was shown to be 18.96 g/ml, and the density of B-52 was shown to be 0.56 g/ml. Further, the Summit 300 mcl valve was tested, in addition to the Aptar 185 mcl valve. The Summit valve was found to dispense 137 mg per spray and 1.37 mg of active per spray, 2.74 mg of active after two sprays, and 4.11 mg of active after 2 sprays. The Aptar valve released 99.7 mg per spray and 0.997 mg of active per spray, 1.994 of active per two sprays, and 2.991 mg of active per 3 sprays.

The mass of formula dispensed in each dose was calculated. As this is a very small mass, its mass was calculated numerous times to increase the confidence in results. The experiment was undertaken using one sleeve made of aluminum foil that acted as a non-absorptive control, a sleeve made of the other materials to be tested (Nylon, fiber glass, PET film, coffee filter paper, and polyester), one container of composition, one dispenser having an actuator nozzle with four outlet ports, a stopwatch, and a calibrated scale.

The scale was correctly aligned on a flat and level surface to calibrate same prior to conducting any measurements. The dispenser was disassembled and the individual components were weighed and recorded. The container was weighed while in the base and the container was depressed while resting in the base. The dispenser was weighed and recorded. The weighing and depressions were repeated approximately 10 times. The depressions happened in quick succession to avoid evaporation of any dribbles on the base. Residue was wiped off the top of the base and the base was reweighed.

Using a dispenser with the control aluminum sleeve, the individual components (base, container, and sleeve) were weighed. The stop-watch was simultaneously started and the base was depressed to release a dose. The sleeve was removed and weighed, while the time was being recorded. The sleeve was kept on the balance and the mass was recorded at appropriate intervals (approximately every 30 seconds) until the difference between the dry and fully saturated sleeve returned to within 10% of the original value. The used sleeve was removed and replaced with a fresh sleeve of a different material. All steps were repeated until every material was tested.

Table 11 illustrates the weight of the container, the amount of material, and the amount of active and solvent dispensed in each of the tests.

TABLE 11

| n | mass container + base (g) | mass dispensed (mg) | active and solvent (mg) |
|---|---|---|---|
| 0 | 88.641 | | |
| 1 | 88.5033 | 137.7 | 27.54 |
| 2 | 88.3618 | 141.5 | 28.3 |
| 3 | 88.2206 | 141.2 | 28.24 |
| 4 | 88.0893 | 131.3 | 26.26 |
| 5 | 87.9575 | 131.8 | 26.36 |
| 6 | 87.8249 | 132.6 | 26.52 |
| 7 | 87.6919 | 133 | 26.6 |
| 8 | 87.5598 | 132.1 | 26.42 |
| 9 | 87.427 | 132.8 | 26.56 |
| 10 | 87.2934 | 133.6 | 26.72 |

The base was then wiped and reweighed (87.2922 g) illustrating that less than 1.2 mg of the dispensed composition remained on the base. The average mass of composition dispensed with each press was 135 mg, with 27 mg comprising the active and solvent.

From the chemical data given for the container, the amount of active in each dose was found to be 20%. Table 12 depicts the mass of the sleeve over a selected time period after coating with the composition.

TABLE 12

| Sleeve Material | Dry mass of sleeve (g) | 1st mass (10 s) (g) | Mass after 20 min (g) | Mass after 30 minutes (g) |
|---|---|---|---|---|
| Nylon | 2.9188 | 2.9488 | 2.9242 | 2.922 |
| Fiber Glass | 1.2253 | 1.2506 | 1.233 | 1.2303 |
| Aluminum | 1.6044 | 1.631 | 1.617175 | 1.6148 |
| PET film | 4.321 | 4.3413 | 4.3241 | 4.3221 |
| Coffee filter paper | 1.7113 | 1.7401 | 1.717 | 1.7144 |
| Polyester | 2.5352 | 2.56 | 2.5378 | 2.5348 |

The mass was calculated for each of the samples and the results appear in Table 13.

TABLE 13

| Material | Formula on sleeve at 10 s (mg) | Equivalent wt. % on sleeve (wt. %) | % Formula on sleeve at 20 mins (%) | % Formula on sleeve at 30 mins (%) | Time to 20% of formula left (min.) |
|---|---|---|---|---|---|
| Nylon | 30 | 22.2% | 18.00 | 10.67 | 19 |
| Fiber Glass | 25.3 | 18.7% | 30.43 | 19.76 | 30 |
| Aluminum | 26.6 | 19.7% | 48.03 | 39.10 | >30 |
| PET film | 20.3 | 15.0% | 15 | 0 | 13 |
| Coffee Filter paper | 28.8 | 21.3% | 19.79 | 10.76 | 20 |
| Polyester | 24.8 | 18.4% | 10.48 | depleted | 14 |

In addition to the results presented in Table 13, FIG. 24 shows the combined evaporation plot for all of the materials.

Thus, the calculated mass of formula that adheres or is otherwise absorbed to each sleeve is consistently between 25 mg to 30 mg. For all samples, this is estimated to be above 90% of the solvent and active dispensed in each dose. Also, the time for 80% of the formula to evaporate can significantly differ depending on the material. For example, the time can take from as little as 14 minutes for the polyester to greater than 30 min for the aluminum foil. The fiber glass and Nylon samples showed steady release rate profiles of deposited formulation over a suitably long period of 30 minutes as compared to other materials tested. The steady release rate profiles suggest that these materials may be more consistent with respect to controlling the composition release from the dispenser.

Figure 25:
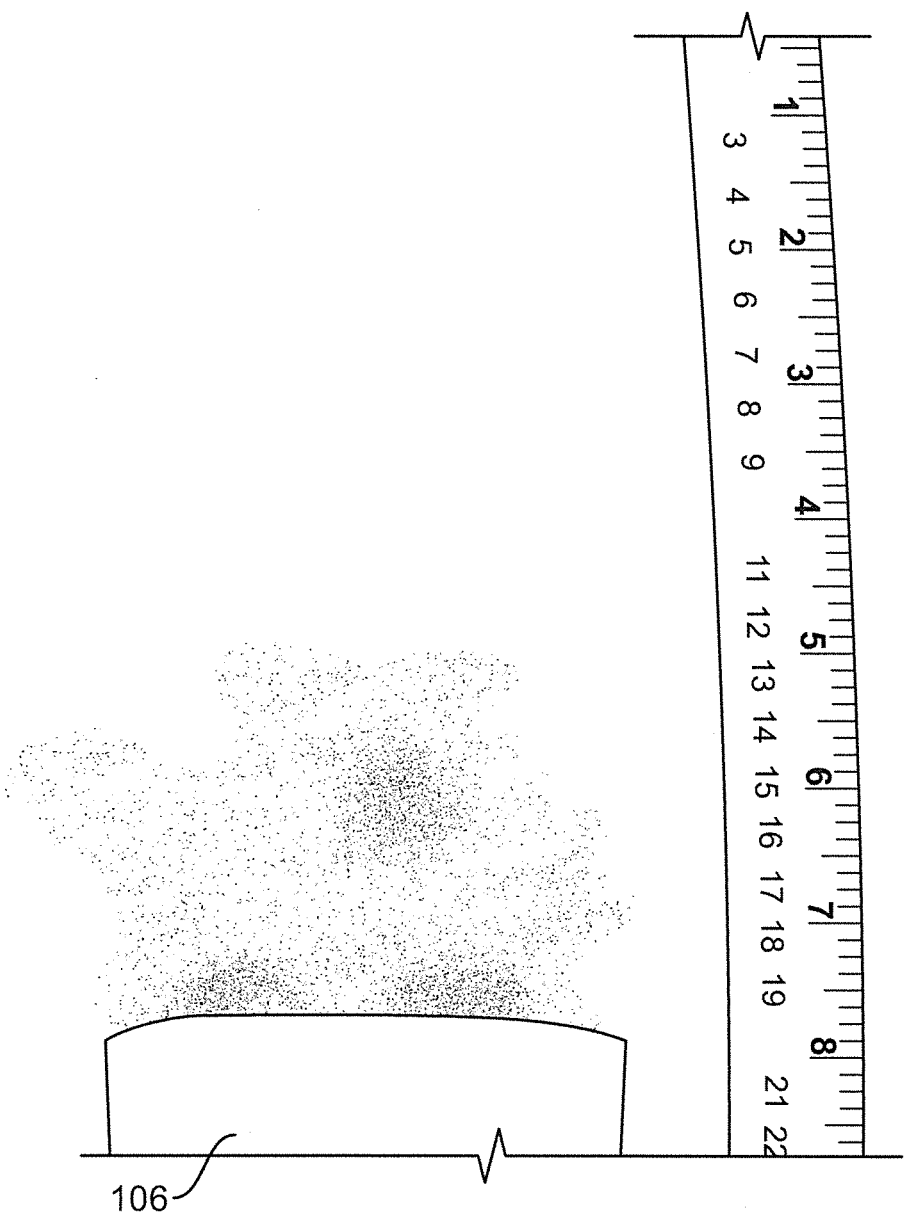
FIG. 25 shows a single frame from a high speed video showing an aerosol spray being emitted as a plume from a dispenser with a sleeve.
Figure 26:
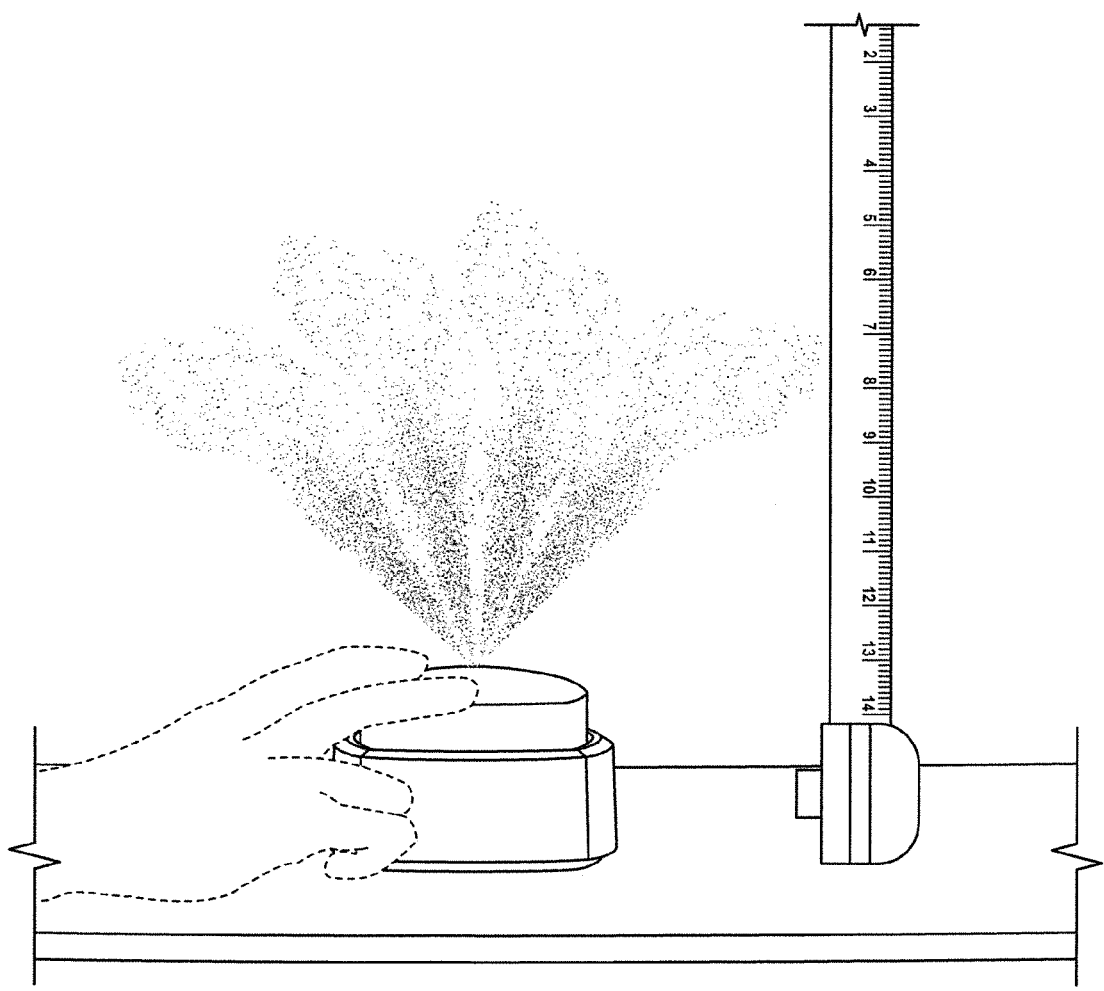
FIG. 26 depicts a single frame from a high speed video showing an aerosolized spray being emitted from a dispenser.

Referring generally to FIGS. 25 and 26, a dispenser having a nylon sleeve was used in conjunction with a container having a composition comprising the B-52 propellant in an amount of 80 wt. %, the Isopar-L solvent in an amount of 18.81 wt. %, the metofluthrin active in an amount of 1.04 wt. %, and a Eucalyptus oil in an amount of 0.15 wt. %.

Various properties of the dispenser were measured after actuation. To conduct the testing, the dispenser was positioned on a laboratory bench and illuminated by two high intensity halogen flood lights. The lights were only turned on directly before making measurements and extinguished after each measurement in order to prevent undue heating of the device. In addition, the vapor plume was highlighted using a dual fiber-optic light source. This allowed the plume to be further illuminated without extra heating and the steerable nature of the fiber optics allowed the lighting to be optimized.

The properties of the actuation and resultant plume were measured using a high speed camera, the MotionBLITZ Cube 2, provided by Mikrotron GmBH. The camera was operated at a maximum resolution of 1280×1024 pixels and a maximum frame rate of 500 fps. The camera was mounted on a professional grade tripod to provide sufficient stability and was controlled by software that allowed control of the gain and video acquisition. The data was saved in a raw binary format and then converted to .avi format with no compression. The frame and timing data was saved embedded in the frame images. A scale ruler was included in the images to provide a reference for later analysis.

The measurements were made in an air-conditioned laboratory where the temperature was about 21° C.±1.5° C. and the humidity was about 71%.

The high speed camera was used to record the visible plume emanating from the top of the device after actuating. A number of videos were recorded using different lighting and exposure settings to optimize the visibility of the ejected plume. The absorbent sleeve was then removed and more videos were recorded to image the jets from the four actuator nozzles. Again, videos were recorded for a number of lighting and exposure settings.

FIG. 25 depicts a single frame from one of the high speed videos. The image was taken 146 ms after actuation. The bright rectangular area is the absorbent sleeve 106, which is overexposed due to the need to brightly illuminate the plume. The two probes apparent in the picture are the ends of the fiber-optic lighting. The plume of vapor leaving the device at about 146 ms after actuation is clearly visible. By analyzing the video it was possible to measure the velocity of the plume front.

The velocity of the plume front was measured using the video methods described above. Table 14 shows the estimated speed of the plume measured up through the channel of the sleeve and then measured over 25 mm segments above the exit from the sleeve.

TABLE 14

| | Velocity (m/s) | | | |
|---|---|---|---|---|
| Distance (mm) | Run 1 | Run 2 | Run 3 | Run 4 |
| Nozzle to top of sleeve | 10.63 | 4.05 | 5.31 | 9.44 |
| 0-25 | 0.83 | 0.39 | 0.54 | 0.96 |

TABLE 14-continued

| | Velocity (m/s) | | | |
|---|---|---|---|---|
| Distance (mm) | Run 1 | Run 2 | Run 3 | Run 4 |
| 25-50 | 0.42 | 0.27 | 0.39 | 0.66 |
| 50-75 | 0.22 | 0.17 | 0.27 | 0.23 |
| 75-100 | 0.14 | 0.11 | 0.16 | 0.17 |

Thus, the turbulent nature of the flow gives a wide range in the estimated values, but it can be seen that the flow slows down by a factor of 10 in the first 25 mm above the screen.

In an additional test, the sleeve was removed from the base of the dispenser and the above test was repeated with further videos recorded. An aerosolized spray was released from the dispenser. A single frame from one of the videos is shown in FIG. 26. A frame from the high speed video of the device is depicted without the absorbent sleeve after actuation of the device. By analyzing the videos, estimates of the aerosolized spray velocity were obtained.

Table 15 shows the aerosolized spray velocity using a dispenser without a sleeve.

TABLE 15

| | Velocity (m/s) | |
|---|---|---|
| Distance (mm) | Run 1 | Run 2 |
| 0-25 | 8.33 | 8.33 |
| 25-50 | 8.33 | 8.33 |
| 50-75 | 4.17 | 6.25 |
| 75-100 | 5.00 | 4.17 |
| 100-125 | 5.00 | 3.13 |
| 125-150 | 2.50 | 3.57 |
| 150-175 | 2.08 | 5.00 |
| 175-200 | 2.08 | 3.13 |
| 200-225 | 0.89 | 2.08 |
| 225-250 | 1.79 | 1.79 |
| 250-275 | 4.17 | 1.25 |
| 275-300 | 0.83 | 0.78 |

Table 15 shows that the flow of the aerosolized spray is very turbulent, but the velocity slows from about 8 m/s at the actuator nozzle to around 2 m/s at 250 mm from the actuator nozzle.

Additionally, the wetting operation of the sleeve via the spray was also measured. The dispenser was positioned on the laboratory bench and illuminated by a dual fiber-optic light source. The position, intensity, and color temperature of the light was adjusted by eye to maximize the visibility of the wetted spot on the absorbent sleeve. Two series of measurements were performed, both looking down from above at a grazing angle of about 30°. The digital camera used was a Canon PowerShot SX150 IS (PC1677). The camera was mounted on a professional grade tripod to provide high stability.

The measurements were made in an air-conditioned laboratory where the temperature was about 21° C.±1.5° C. and the humidity was about 73%.

Two series of photographs were taken. In both cases, an image was taken of the un-wetted sleeve. Additional images were taken just after the spray was activated and then at subsequent intervals afterwards until the wetted spot became difficult to discern. The first series of images were taken at 1 minute intervals up to 6 minutes after activation. It was clear that most of the initial spreading of the wetting took place in the first minute, so a second series of photographs were taken at 15 second intervals up to 1 minute, then at 2 minutes, and then 3 minutes. Finally, a new sleeve was inserted, the spray actuated, and the size of the wetted spot on the outside of the sleeve was measured 2 minutes after actuation, where the spot had achieved maximum size while still being reasonably defined. After 2 minutes, the spot became less clear as it was absorbed into the sleeve.

The images were taken at intervals up to 6 minutes after actuation and it was found that the wetted spot slightly increased in size from around 15 mm to about 25 mm at 2 minutes, and then becomes less defined and visible as the liquid is absorbed.

The second sequence of images were taken at intervals up to 2 minutes after actuation and it was found that there was little variation from actuation up to 2 minutes as the wetting seemed to be instantaneous with the actuation.

Additionally, the sleeve was visually inspected to confirm the results of the photographs. The results of the visual inspection of the wetted spot on the outside of the absorbent sleeve substantially matched those photographed on the inside. The visual inspection allowed the wetted spot size to be readily measured. The wetted spot was approximately elliptical, being about 25 mm wide and about 35 mm high. The elliptical shape confirms that the spray from the actuator nozzle is conical.

Turning to Table 16 below, a system is considered that illustrates bulk density, porosity, and surface area of various sleeve materials. The sleeve materials that were tested include Nylon, Coffee Filter Paper, Polyester, and Fiber Glass.

A BET surface area analysis was conducted on each of the sleeve samples. BET surface analysis uses the physical adsorption of gas molecules on a degassed solid surface. It assumes monolayer adsorption (i.e., Krypton is used) and the results are an inverse relation plot of the volume of adsorbed gas against the relative pressure. From the relation plot, the c value shows how strongly the Krypton sticks to the substrate. The BET surface area in $m^2/g$ of material was also calculated.

A Mercury Intrusion Porosimetry (MIP) analysis was also conducted on each of the samples. MIP provides measurements relating to pore size distribution, pore volume, pore area, and the porosity of materials. Measurements were conducted using a Micromeritics AutoPore IV porosimeter, which is capable of measuring pore size distributions in the range 0.003 μm to 600 μm (depending on the nature of the sample).

Helium density of the samples were also measured via helium pycnometry, which is used to measure the absolute density of a material. The helium density was measured using a Micromeritics Accupyc 1330 instrument.

Table 16 shows the surface area, median pore diameter, total intrusion volume, porosity, and helium density for Nylon, Coffee Filter Paper, Polyester, and Fiber Glass.

TABLE 16

| Material | BET-surface area ($m^2/g$) | Median Pore Diameter (μm) | Total Intrusion Volume (mL/g) | Porosity (%) | Helium density ($g/cm^3$) |
|---|---|---|---|---|---|
| Nylon | 0.113 | 74.7 | 1.5509 | 57.5 | 1.142 |
| Fiber Glass | 0.191 | 80.6 | 7.1288 | 83.5 | 2.289 |
| Coffee filter paper | 0.460 | 50.6 | 3.7196 | 77.7 | 1.273 |
| Polyester | 0.126 | 451.1 | 2.9570 | 75.6 | 1.379 |

The results of Table 16 suggest that pores larger than 600 μm for the Nylon sample may be present. Table 16 also suggests smaller pores for the coffee filter paper as compared to the Nylon sample, which is most likely due to the larger surface area of the coffee filter paper. Additionally, Table 16 suggests the polyester sample comprises very large pores, which may explain the variances between absorbency and release rates of the formulation applied to the polyester sample as compared to Fiber Glass and Nylon samples.

Referring to Tables 17-23, numerous dispenser systems were tested to determine particle size measurements of the flowable medium after being dispensed from various actuator nozzles. In particular, the particle size distribution of the aerosol spray and the sleeve generated plume from the four outlet port actuator nozzle was measured using a Spraytec laser diffraction system provided by Malvern Instruments using a 300 mm lens that allows measurement of spray particle and spray droplet size distributions in real-time from 0.1-900 microns (Dv50: between 0.5-600 microns).

The four outlet port actuation nozzle from the dispenser was fitted to a refill formulation metered dose aerosol container without the presence of the device sleeve and was mounted centrally below the measurement window of the Malvern Spraytec laser diffraction system, which ensured that the resulting spray would pass through the measurement zone. The measurement capture program was run and the aerosol container was then activated using the Malvern Spraytec Nasal Spray Accessory, thereby spraying the aerosol through the incident beam of collimated laser light. The measurement was recorded and particle size distribution calculated.

Each experimental sample measured for its aerosol droplet size distribution was measured at distances of 70 mm from the device actuator nozzle to the incident beam of collimated laser light, and again at 170 mm from the device actuator nozzle to the incident beam collimated laser light using the setup as described above.

The distance of 70 mm is representative of the distance above the actuator nozzle to which the aerosol spray would intersect with the sleeve surface in the fully assembled dispensing device. The distance of 170 mm is representative of the distance above the actuator nozzle to the upper edge of the sleeve in the fully assembled device.

Three samples of four outlet port actuator nozzles with varying nozzle orifice sizes, listed below, were tested for their effects on particles size distribution using the above method.

The three actuator nozzles tested included an actuator nozzle from a molded prototype device with an outlet port diameter of 0.51 mm, an additional actuator nozzle with an outlet port diameter of 0.51 mm, and an actuator nozzle with an outlet port diameter of 1.2 mm.

A four outlet port actuator nozzle from the dispenser was fitted to a refill formulation metered dose aerosol container without the presence of the device sleeve and was mounted below the measurement window of the Malvern Spraytec laser diffraction system, thereby ensuring that the aerosol jet from only one out of the four outlet ports of the actuator nozzles would pass through the measurement zone during actuation. The measurement capture program was run and the aerosol container was then activated using the Malvern Spraytec Nasal Spray Accessory, thereby spraying the aerosol through the incident beam collimated laser light. The measurement was recorded and particle size distribution calculated.

Each experimental sample measured for its aerosol droplet size distribution was measured at distances of 70 mm from the device actuator nozzle to the incident beam and again at a distance of 120 mm, 150 mm, or 170 mm from the actuator nozzle to the incident beam for the actuator nozzle samples (0.51 mm, 1.2 mm, and the additional 0.51 mm sample) using the setup as described above.

Three samples of actuator nozzles having four outlet ports with varying outlet port sizes, listed below, were tested for their effects on particles size distribution using the above method.

The actuator nozzles tested included an actuator nozzle from a molded prototype device with an outlet port diameter of 0.51 mm, an additional actuator nozzle with an outlet port diameter of 0.51 mm, and an actuator nozzle with an outlet port diameter of 1.2 mm.

The actuator nozzle having four outlet ports was fitted with a refill formulation metered dose aerosol container and sleeve, and was mounted centrally 150 mm below the measurement window of the Malvern Spraytec laser diffraction system, thereby ensuring the resulting spray plume exiting the volume of the sleeve would pass through the measurement zone. The measurement capture program was run and the dispenser was then actuated, thereby spraying the aerosol within the sleeve volume of which the resulting plume exited the volume of the sleeve and passed through the incident beam. The measurement was recorded and particle size distribution calculated.

Three samples of sleeve materials, listed below, were tested in combination with the base and actuator nozzle having an outlet port diameter of 0.51 mm for their effects on particles size distribution on the plume exiting the volume of the sleeve using the above method. The sleeve materials tested included Nylon, Fiber glass, and Polyester.

Table 17 shows the particle size distribution of the flowable product emitted from a first actuator nozzle having a diameter size of about 0.5 mm that emitted spray through four outlet ports.

TABLE 17

| Distance | Dv10 | Dv50 | Dv90 | % < 10 μm | Shot Weight (mg) |
| --- | --- | --- | --- | --- | --- |
| 70 mm | 6.775 μm | 17.58 μm | 40.58 μm | 21.95 | 140.44 |
| 170 mm | 7.546 μm | 17.4 μm | 38.68 μm | 19.9 | 138.91 |

Table 18 shows the particle size distribution of the flowable product emitted from a second actuator nozzle having a diameter size of 1.2 mm that emitted spray through four outlet ports.

TABLE 18

| Distance | Dv10 | Dv50 | Dv90 | % < 10 μm | Shot Weight (mg) |
| --- | --- | --- | --- | --- | --- |
| 70 mm | 22.95 μm | 73.33 μm | 249.8 μm | 1.037 | 145.27 |
| 170 mm | No data | No data | No data | No data | No data |

Table 19 shows the particle size distribution of flowable product emitted from a third actuator nozzle having a diameter size of 0.5 mm that emitted spray through four outlet ports.

TABLE 19

| Distance | Dv10 | Dv50 | Dv90 | % < 10 μm | Shot Weight (mg) |
|---|---|---|---|---|---|
| 70 mm | 6.601 μm | 18.94 μm | 125.7 μm | 22.07 | 140.02 |
| 170 mm | 6.754 μm | 16.16 μm | 38.14 μm | 24.04 | 141.94 |

Table 20 shows the particle size distribution of flowable product emitted from the first actuator nozzle having a diameter size of about 0.5 mm that emitted spray through one outlet port.

TABLE 20

| Distance | Dv10 | Dv50 | Dv90 | % < 10 μm | Shot Weight (mg) |
|---|---|---|---|---|---|
| 70 mm | 16.22 μm | 34.18 μm | 66.53 μm | 2.517 | 141.45 |
| 170 mm | 10.17 μm | 26.56 μm | 68.76 μm | 9.555 | 146.67 |

Table 21 shows the particle size distribution of flowable product emitted from the second actuator nozzle having a diameter size of 1.2 mm that emitted spray through one outlet port.

TABLE 21

| Distance | Dv10 | Dv50 | Dv90 | % < 10 μm | Shot Weight (mg) |
|---|---|---|---|---|---|
| 70 mm | 17.08 μm | 41.93 μm | 121.1 μm | 2.473 | 140.16 |
| 170 mm | 14.87 μm | 36.5 μm | 92.12 μm | 3.639 | 143.40 |

Table 22 shows the particle size distribution of flowable product emitted from the third actuator nozzle having a diameter size of 0.5 mm that emitted spray through one outlet port.

TABLE 22

| Distance | Dv10 | Dv50 | Dv90 | % < 10 μm | Shot Weight (mg) |
|---|---|---|---|---|---|
| 70 mm | 16.8 μm | 37.67 μm | 76.82 μm | 2.347 | 143.42 |
| 170 mm | 8.492 μm | 28.27 μm | 74.12 μm | 13.65 | 143.52 |

Table 23 shows the particle size distribution of flowable product emitted from the third actuator nozzle and measured after the particles exited a sleeve through an upper opening thereof. The test was repeated for various sleeves.

TABLE 23

| Sleeve Type | Dv10 | Dv50 | Dv90 | % < 10 μm | Shot Weight (mg) |
|---|---|---|---|---|---|
| Nylon | 5.493 μm | 12.66 μm | 28.95 μm | 35.99 | 152.64 |
| Fiber Glass | 5.081 μm | 11.25 μm | 24.51 μm | 42.59 | 148.59 |
| Polyester | 5.883 μm | 15.56 μm | 42.79 μm | 28.29 | 153.6 |

Interestingly, utilizing a shade resulted in a significant decrease in the particle size distribution as compared to all nozzle types. All of the nozzles were sprayed without a shade to determine the particle size distribution at 70 mm and 170 mm. It was theorized that a measurement at 70 mm without a shade (see Tables 18-22) would be commensurate with a distance that needed to be traveled for the aerosolized spray to impact an inner surface of the shades that were tested, the results of which are shown in Table 23. It was found that all of the nozzles that were tested without a shade had significantly higher particle size distributions, e.g., Dv(90) distributions of between about 41 μm to about 250 μm for 4 sprays and about 67 μm to about 121 μm for a single spray, than found with the particle distribution measured at an outlet of the nylon and glass fiber shades that had Dv(90) distributions of about 29 μm and 25 μm, respectively. The polyester shade resulted in a Dv(90) distribution of about 43 μm.

Further, it was also theorized that a measurement of 170 mm without a shade (see Tables 18-22) would be commensurate with a distance that needed to be traveled for the aerosolized spray to exit the shades that were tested, the results of which are shown in Table 23. It was found that all of the nozzles that were tested without a shade had significantly higher particle size distributions, e.g., Dv(90) distributions of between about 38 μm to about 39 μm for 4 sprays (the second nozzle did not generate a detectable spray because the particles did not travel that high) and about 69 μm to about 92 μm for a single spray, than found with the particle distribution measured at an outlet of the nylon and glass fiber shades that had Dv(90) distributions of about 29 μm and 25 μm, respectively. As previously noted, the polyester shade resulted in a Dv(90) distribution of about 43 μm.

Still further, testing provided insight into the percentage of particles that were less than 10 μm. Regardless of whether a single spray or four sprays were performed from any of the nozzles, the percentage range of particles having a size less than 10 μm was from about 1% to about 22% as measured at 70 mm and was from about 20% to about 24% as measured at 170 mm (the second nozzle did not generate a detectable spray because the particles did not travel that high). In contrast, all of the shades tested resulted in a percentage of total particles that were less than 10 μm of at least 28% and up to 43%.

It is therefore contemplated that the inclusion of a shade, substrate or channel has a significant impact on the particle size distribution that exits the upper end, outlet, or aperture thereof. Indeed, it is contemplated that a substrate having a conduit with a flowable medium discharged therein comprises a particle size distribution that is less than or equal to 30 μm for a Dv(90) particle size distribution at an outlet of the channel, less than or equal to 15 μm for a Dv(50) particle size distribution at an outlet of the channel, and/or less than or equal to 6 μm for a Dv(10) particle size distribution at an outlet of the channel. Further, it is also contemplated that a substrate having a conduit with a flowable medium discharged therein comprises a particle size distribution in which at least 15% of the particles are less than 10 μm in size, at least 25% of the particles are less than 10 μm in size, at least 30% of the particles are less than 10 μm in size, at least 35% of the particles are less than 10 μm in size, at least 40% of the particles are less than 10 μm in size, and/or at least 45% of the particles are less than 10 μm in size.

It is also contemplated that other types of housings, e.g., telescopic housings or housings utilizing electronic elements, can similarly encompass the above-noted characteristics. For example, the electro-mechanical dispensing systems disclosed in U.S. patent application Ser. Nos. 11/725,402 and 11/893,532, may be modified to include a natural look to give the impression that the dispenser does not fully or partially include any man-made features as noted above. For example, the dispenser could be fully or partially imparted with a natural looking pattern, mimic the shape of a naturally occurring object, or be formed from a naturally occurring object. However, it is also contemplated that other bases could be made from different materials such as pebbles, stones, fossilized articles, etc.

In some cases, the materials are selected from, or include manufactured materials configured to approximate, naturally occurring substances, such as wood, stone, paper, or rock, or combinations thereof. Any such materials can be selected based upon their having a natural looking appearance and/or a natural feeling to the touch. By incorporating natural materials, or analogs of natural materials, the dispenser 100 can be made to look more appropriate for placement in an outdoors location, such as in a sun room or on a porch, balcony, or patio, or can complement the look and feel of existing natural objects within the home.

In some embodiments, a lid (not shown) may be included to at least partially cover the dispenser 100. In one embodiment, the lid is imparted with a grid-like configuration containing apertures therethrough. In other embodiments, the lid may have a mesh, screen, or woven configuration that approximates the porosity of a grid-like configuration. In one embodiment, the sleeve 106 and lid are formed of a rigid material to enable a user to grasp the dispenser 100 by the sleeve 106 without causing its collapse.

Further, the interior surface of the sleeve 106 may have various textures and/or surface patterns, such as a rough surface, a smooth surface, a channeled surface, and combinations thereof that may affect deflection angles that, in turn, may impact the amount of deposition on the interior surface of the sleeve as well as the amount of composition deflected therefrom. Further, increasing or decreasing the velocity of the stream(s) and/or providing some type of metering device may assist in varying the amounts of composition distributed into the first, second, and third quantities, respectively.

In other embodiments, it is contemplated that other surface markings, interruptions, and/or surface irregularities may be provided on the sleeve, either integral with or as a separate component, to affect the dispensing properties of the dispenser. For instance, it is envisioned that baffles, ribs, or other components could be added to the interior surface of the sleeve to assist in the dispensing and/or direct a certain amount of the composition to either the plume or onto the interior surface of the sleeve. Additionally, other elements may be provided on the dispenser that assists in the formation of the plume.

In further embodiments, the dispenser may incorporate more complex components that assist in the operation of the dispenser. For instance, additional and/or alternate mechanisms may be used to release the aerosol composition from the container. In this embodiment, a mechanical and/or electromechanical system may be used that activates the dispenser in response to an elapsed time interval determined by a timer (not shown) and/or a signal from a sensor (not shown), such as a motion sensor or other type of sensor.

In one implementation, a sensor may be a light-sensing element, such as a photodetector, or may be a sound detecting element, such as a microphone. In this embodiment, the dispenser may be activated, for example, by entry of the user into a room where the dispenser has been placed. In this case, the sensor detects the entry of the user, which then triggers activation of the dispenser to release a metered dose of the composition from the container. In one embodiment, the dispenser may incorporate a solenoid (not shown) powered by batteries (not shown) that releases the metered dose of the composition.

In additional embodiments, the use of one or more lights in the dispenser is contemplated. For example, a light may be provided in a portion of the dispenser. In one embodiment, the light may correspond to the efficacy of the flowable medium being emitted. For example, the light may be illuminated while the flowable medium is present on the sleeve and/or is being passively diffused. The light may fade or otherwise dissipate as the flowable medium is passively diffused. The light may extinguish when passive diffusion is complete or substantially complete. It is further contemplated that a light may be provided to illuminate the wetted area on the sleeve and/or to assist in illuminating individual fibers of the sleeve. The dispenser may also operate as a stand-alone light.

In a different embodiment, the dispenser may be utilized in an inverted manner such that the dispenser could be hung or otherwise suspended. In this embodiment, a cord or other mechanism may need to be provided to actuate the dispenser.

In other embodiments, the dispenser may be operated in a manner that allows a user to manually spray the dispenser. For example, a container having a composition and a suitable sprayer may be provided to the user separately. The user may spray one or more portions of the internal and/or external surface of the sleeve to provide passive diffusion capabilities. In this instance, the user may want to spray a top portion of the sleeve such that a portion of the composition is released actively and a portion of the composition is directed onto the sleeve for passive diffusion. In this way, the sleeve may be dosed with the composition through user intervention. In a different embodiment, the sleeve may have the capability of being dosed through a container disposed within the base of the dispenser, as well as through manual spraying on the exterior of the sleeve.

In a different embodiment, the amount of flowable product dispensed in an actuation cycle may be dependent upon numerous factors. For example, one amount of flowable medium may be discharged at a specific velocity and a second amount of flowable medium may be discharged at a different velocity. The amount and velocity of flowable medium discharged may be related to how often the dispenser is actuated (e.g., in sequential actuations, within a certain time frame with respect to the last actuation, etc.).

The container 104 may be an aerosol container, pump-type sprayer, and the like. Additional examples of reservoirs, activation mechanisms, compositions, substrates, and the like that may be used herein include those disclosed in U.S. Pat. Nos. 7,837,065, 8,061,562, and U.S. patent application Ser. Nos. 11/801,554, 11/893,456, 11/893,489, 11/893,476, 11/805,976, 11/898,456, and 11/893,532.

Any of the terms "flowable medium," "composition," "formulation," and the like, are used interchangeably and are not intended to be limiting. Rather, the terms are intended to be inclusive of any substance in any form (e.g., liquid, gas, solid, etc.) that is capable of being dispensed or otherwise emitted.

The term "through" as used herein, generally means a path taken by the flowable medium from the base 102 along or into the channel 242 or conduit to the upper opening 238 or outlet thereof. In contrast, when discussing the flowable medium being directed "through" a wall of the sleeve 106, it means that the flowable medium is discharged directly all the way through fibers of the sleeve 106 by overcoming the fiber strength of the sleeve 106, as opposed to absorbing into the fibers of the sleeve 106 and being passively emitted therefrom.

Additional features contemplated herein include use-up indicators or use cues. For example, in one embodiment where the volatile active is dispensed onto the interior surface 232 of the sleeve 106, an ink is provided within the sleeve 106 that may appear or disappear to indicate when the volatile active has completely evaporated therefrom. Combinations of appearing and disappearing inks are contemplated to create more complex features upon the application and gradual emanation of the volatile active from the dispenser 100. Other use-up cues could be employed, including, for example, a liquid/gel vessel that is peeled to activate, inks that use capillary action or absorption that activate upon peeling or pressing them together with an absorbent layer, a dial to set a date, or an area to write the date when activated, etc.

In another embodiment, the dispenser 100 may incorporate a mechanism to augment emanation rates such as a heater and/or a fan or other means as are known in the art.

All documents cited in the Detailed Description of the Invention are, in relevant part, incorporated herein by reference; the citation of any document is not to be construed as an admission that it is prior art with respect to the present invention.

INDUSTRIAL APPLICABILITY

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A dispensing system, comprising:
   a substrate having a channel;
   a base having an upper housing and a lower housing, wherein a container for discharging a flowable medium into the channel is completely accommodated within the base and is partially exterior to the substrate,
   wherein the channel comprises:
      an uninterrupted volume of at least 300 $cm^3$, and
   wherein the substrate comprises:
      an average wicking speed of at least 0.05 mm/s.

2. The dispensing system of claim 1, wherein the average wicking speed is between 0.05 mm/s to 0.1 mm/s.

3. The dispensing system of claim 2, wherein the substrate is capable of absorbing about 0.015 mg/$mm^2$ of the flowable medium.

4. The dispensing system of claim 1, wherein a discharge stream of the flowable medium is discharged onto a surface defining the channel, and wherein an external surface of the substrate is imparted with at least one wet spot that is most visually pronounced about 2 minutes after the discharge of the flowable medium.

5. The dispensing system of claim 1, wherein at least one discharge stream of the flowable medium is discharged onto a surface defining the channel, and wherein an external surface of the substrate is imparted with at least one wet spot having an average size of greater than or equal to 8 $cm^2$ ten seconds after the discharge of the flowable medium.

6. The dispensing system of claim 1, wherein the substrate comprises:
   a plurality of non-woven fibers.

7. A dispensing system, comprising:
   a substrate having a channel; and
   a mechanism for discharging a flowable medium into the channel being partially exterior to the substrate, wherein the mechanism includes an upper housing and a lower housing and the upper housing is movable with respect to the lower housing;
   wherein the channel comprises an uninterrupted volume of at least 300 $cm^3$, and
   wherein the substrate allows the flowable medium to wick therethrough.

8. A dispensing system, comprising:
   a substrate having a channel; and
   a base having an upper housing and a lower housing, wherein a container for discharging a flowable medium into the channel is completely accommodated within the base and is partially exterior to the substrate;
   wherein the channel comprises an uninterrupted volume of at least 300 $cm^3$, and
   wherein the substrate allows the flowable medium to wick therethrough.

9. The dispensing system of claim 1, wherein the container is an aerosol container.

10. The dispensing system of claim 1, wherein the container is a pump-type container.

11. The dispensing system of claim 1, wherein the container partially extends through a lower opening of the channel.

12. The dispensing system of claim 7, wherein the substrate comprises an average wicking speed of at least 0.05 mm/s.

13. The dispensing system of claim 8, wherein the container is an aerosol container.

14. The dispensing system of claim 8, wherein the container is a pump-type container.

15. The dispensing system of claim 8, wherein the substrate comprises an average wicking speed of at least 0.05 mm/s.

16. The dispending system of claim 8, wherein the container partially extends through a lower opening of the channel.

* * * * *